US008183224B2

(12) United States Patent
Jagtap et al.

(10) Patent No.: US 8,183,224 B2
(45) Date of Patent: May 22, 2012

(54) PURINE DERIVATIVES AS ADENOSINE A₁ RECEPTOR AGONISTS AND METHODS OF USE THEREOF

(75) Inventors: Prakash Jagtap, N. Andover, MA (US); Csaba Szabo, Gloucester, MA (US); Andrew L. Salzman, Herzliya (IL)

(73) Assignee: Inotek Pharmaceuticals Corporation, Lexington, MA (US)

( * ) Notice: Subject to any disclaimer, the term of this patent is extended or adjusted under 35 U.S.C. 154(b) by 267 days.

(21) Appl. No.: 12/221,539

(22) Filed: Aug. 4, 2008

(65) Prior Publication Data

US 2009/0062314 A1 Mar. 5, 2009

Related U.S. Application Data

(62) Division of application No. 11/137,632, filed on May 25, 2005, now Pat. No. 7,423,144.

(60) Provisional application No. 60/574,805, filed on May 26, 2004, provisional application No. 60/588,263, filed on Jul. 15, 2004.

(51) Int. Cl.
*A61K 31/7076* (2006.01)
*C07H 19/167* (2006.01)

(52) U.S. Cl. ........................ 514/46; 536/27.3; 536/27.22

(58) Field of Classification Search .................. None
See application file for complete search history.

(56) References Cited

U.S. PATENT DOCUMENTS

| 3,819,613 | A |   | 6/1974  | Kawazoe et al. |
|-----------|---|---|---------|----------------|
| 3,832,341 | A |   | 8/1974  | Duschinsky |
| 4,242,505 | A |   | 12/1980 | Kawahara et al. |
| 4,968,697 | A |   | 11/1990 | Hutchison |
| 5,140,015 | A |   | 8/1992  | Olsson et al. |
| 5,206,222 | A |   | 4/1993  | Forman et al. |
| 5,219,840 | A |   | 6/1993  | Gadient et al. |
| 5,278,150 | A |   | 1/1994  | Olsson et al. |
| 5,280,015 | A |   | 1/1994  | Jacobson et al. |
| 5,304,277 | A |   | 4/1994  | Ohara et al. |
| 5,407,793 | A |   | 4/1995  | Del Nido et al. |
| 5,443,836 | A |   | 8/1995  | Downey et al. |
| 5,589,467 | A |   | 12/1996 | Lau et al. |
| 5,604,210 | A | * | 2/1997  | Nagaoka et al. ............. 514/46 |
| 5,789,416 | A |   | 8/1998  | Lum et al. |
| 5,801,159 | A | * | 9/1998  | Miller et al. ............... 514/45 |
| 6,180,615 | B1 |  | 1/2001  | Zablocki et al. |
| 6,214,807 | B1 |  | 4/2001  | Zablocki et al. |
| 6,326,359 | B1 |  | 12/2001 | Monaghan et al. |
| 6,358,536 | B1 * | | 3/2002  | Thomas ..................... 424/608 |
| 6,368,573 | B1 |  | 4/2002  | Leung |
| 6,403,567 | B1 |  | 6/2002  | Zablocki et al. |
| 6,426,337 | B1 |  | 7/2002  | Cox et al. |
| 6,440,948 | B1 |  | 8/2002  | Zablocki et al. |
| 6,448,236 | B1 |  | 9/2002  | Monaghan et al. |
| 6,525,032 | B2 |  | 2/2003  | Mantell et al. |
| 6,528,494 | B2 |  | 3/2003  | Cox et al. |
| 6,531,457 | B2 |  | 3/2003  | Linden et al. |
| 6,534,486 | B1 |  | 3/2003  | Allen et al. |
| 6,638,914 | B1 |  | 10/2003 | Fishman et al. |
| 6,753,322 | B2 |  | 6/2004  | Mantell et al. |
| 6,903,079 | B2 * | | 6/2005  | Jagtap et al. ................. 514/45 |
| 6,921,753 | B2 |  | 7/2005  | Mantell et al. |
| 2001/0051612 | A1 | | 12/2001 | Cristalli |
| 2003/0013675 | A1 | | 1/2003  | Yeadon et al. |
| 2003/0055021 | A1 | | 3/2003  | DeNinno et al. |
| 2006/0034941 | A1 * | | 2/2006 | Dobson ..................... 424/608 |
| 2007/0238694 | A1 * | | 10/2007 | Salzman et al. ............. 514/47 |

FOREIGN PATENT DOCUMENTS

| CN | 1164122      | 11/1997 |
|----|--------------|---------|
| DE | 2342479 A1   | 3/1975  |
| FR | 2186470      | 1/1974  |
| KR | 20030005241  | 1/2003  |
| WO | 94/02497 A1  | 2/1994  |
| WO | 95/02604 A1  | 1/1995  |
| WO | 95/11681 A1  | 5/1995  |
| WO | 96/02553 A2  | 2/1996  |
| WO | 97/33590 A1  | 9/1997  |
| WO | 97/33879 A1  | 9/1997  |
| WO | 98/08855 A2  | 3/1998  |
| WO | 98/50047 A1  | 11/1998 |
| WO | 99/20284 A1  | 4/1999  |
| WO | 01/19360 A2  | 3/2001  |
| WO | 01/40245 A1  | 6/2001  |
| WO | 01/45715 A2  | 6/2001  |
| WO | 02/055085 A2 | 7/2002  |
| WO | 02/083152 A1 | 10/2002 |
| WO | 03/029264 A2 | 4/2003  |

OTHER PUBLICATIONS

Soulere et al., "Synthesis and Uptake of Nitric Oxide-Releasing Drugs by the P2 Nucleoside Transporter in *Trypanosoma equiperdu*" Bioorganic and medicinal chemistry letters (2000) vol. 10 pp. 1347-1350.* Witte et al., "Nitric oxide enhances experimental wound healing in diabetes" British Journal of Surgery (2002) vol. 89 pp. 1594-1601.*
Machine translation of foreign patent application DE2342479, (Mar. 13, 1975) downloaded from Google Translate (http://translate.google.com/?hl=en&tab=TT#).*
Al-Mughales, J. et al., "The chemoattractant activity of rheumatoid synovial fluid for human lymphocytes is due to multiple cytokines," Clin. Exp. Immunol., vol. 106:230-236 (1996).
Baraldi, Pier Giovanni et al., "Synthesis and Biological Activity of a New Series of N6-Arylcarbamoyl, 2-(Ar)alkynyl-N6-arylcarbamoyl, and N6-Carboxamido Derivatives of Adenosine-5'-N-ethyluronamide as A1 and A3 Adenosine Receptor Agonists," J. Med. Chem., vol. 41:3174-3185 (1998).

(Continued)

*Primary Examiner* — Eric S Olson
(74) *Attorney, Agent, or Firm* — Nelson Mullins Riley & Scarborough LLP; Jane E. Remillard, Esq.; Pankaj N. Desai

(57) ABSTRACT

The invention relates to Purine Derivatives; compositions comprising an effective amount of a Purine Derivative; and methods for reducing an animal's rate of metabolism, protecting an animal's heart against myocardial damage during cardioplegia; or for treating or preventing a cardiovascular disease, a neurological disorder, an ischemic condition, a reperfusion injury, obesity, a wasting disease, or diabetes, comprising administering an effective amount of a Purine Derivative to an animal in need thereof.

18 Claims, 5 Drawing Sheets

OTHER PUBLICATIONS

Beukers, Margot W. et al., "N6-Cyclopentyl-2-(3-phenylaminocarbonyltriazene-1-yl)adenosine (TCPA), a Very Selective Agonist with High Affinity for the Human Adenosine A1 Receptor," J. Med. Chem., vol. 46:1492-1503 (2003).

Beukers, Margot W. et al., "New, Non-Adenosine, High-Potency Agonists for the Human Adenosine A2B Receptor with an Improved Selectivity Profile Compared to the Reference Agonists N-Ethylcarboxamidoadenosine," Journal of Medicinal Chemistry, vol. 47(15):3707-3709 (2004).

Bouma, Maarten G. et al., "Differential Regulatory Effects of Adenosine on Cytokine Release by Activated Human Monocytes," The Journal of Immunology, vol. 153:4159-4168 (1994).

Bradley, Karri K. et al., "Purine Nucleoside-Dependent Inhibition of Cellular Proliferation in 1321N1 Human Astrocytoma Cells," The Journal of Pharmacology and Experimental Therapeutics, vol. 299(2):748-752 (2001).

Broadley, Kenneth J. et al., "Drugs modulating adenosine receptors as potential therapeutic agents for cardiovascular diseases," Exp. Opin. Ther. Patents, vol. 10(11):1669-1692 (2000).

Bruns, Robert F., "Adenosine receptor activation in human fibroblasts: nucleoside agonists and antagonists," Can. J. Physiol. Pharmacol., vol. 58:673-691 (1980).

Bruns, Robert F. et al., "Characterization of the A2 Adenosine Receptor Labeled by [3H]NECA in Rat Striatal Membranes," Biological Pharmacology, vol. 89:331-346 (1986).

Camaioni, Emidio et al., "Adenosine Receptor Agonists: Synthesis and Biological Evaluation of the Diastereoisomers of 2-(3-Hydroxy-3-phenyl-1-propyn-1-yl)NECA," Bioorganic & Medicinal Chemistry, vol. 5(12):2267-2275 (1997).

Cristalli, Gloria et al., "2-Alkynyl Derivatives of Adenosine-5'-N-ethyluronamide: Selective A2 Adenosine Receptor Agonists with Potent Inhibitory Activity on Platelet Aggregation," J. Med. Chem., vol. 37:1720-1726 (1994).

Cristalli, Gloria et al., "2-Alkynyl Derivatives of Adenosine and Adenosine-5'-N-ethyluronamide as Selective Agonists at A2 Adenosine Receptors," J. Med. Chem., vol. 35:2363-2368 (1992).

Cristalli, Gloria et al., "2-Aralkynyl and 2-Heteroalkynyl Derivatives of Adenosine-5'-N-ethyluronamide as Selective A2a Adenosine Receptor Agonists," J. Med. Chem., vol. 38:1462-1472 (1995).

Dalpiaz, Alessandro et al., "Synthesis and Study of 5'-Ester Prodrugs of N6-Cyclopentyladenosine, a Selective A1 Receptor Agonist," Pharmaceutical Research, vol. 18(4):531-536 (2001).

De Lean, Andre et al., "Validation and Statistical Analysis of a Computer Modeling Method for Quantitative Analysis of Radioligand Binding Data for Mixtures of Pharmacological Receptor Subtypes," Molecular Pharmacology, vol. 21:5-16 (1982).

Deninno, Michael P. et al., "3'-Aminoadenosine-5'-uronamides: Discovery of the First Highly Selective Agonist at the Human Adenosine A3 Receptor," J. Med. Chem., vol. 46:353-355 (2003).

Fisher, Charles J. Jr. et al., "Treatment of Septic Shock with the Tumor Necrosis Factor Receptor: Fc Fusion Protein," N. Engl. J. Med., vol. 334(26):1697-1702 (1996).

Follmann, Hartmut et al., "Adenine Nucleosides in Solution: Circular Dichroism Studies and Base Conformation," Eur. J. Biochem., vol. 58:31-41 (1975).

Francis, John E. et al., "Highly Selective Adenosine A2 Receptor Agonists in a Series of N-Alkylated 2-Aminoadenosines," J. Med. Chem., vol. 34:2570-2579 (1991).

Hasko, Gyoergy et al., "Adenosine Receptor Agonists Differentially Regulate IL-10, TNF-a, and Nitric Oxide Production in RAW 264.7 Macrophages and in Endotoxemic Mice," The Journal of Immunology, vol. 157:4634-4640 (1996).

Homma, Hiroshi et al., "Nucleosides and Nucleotides. 112. 2-(1Hexyn-1-yl)adenosine-5'-uronamides: A New Entry of Selective A2 Adenosine Receptor Agonists with Potent Antihypertensive Activity," J. Med. Chem., vol. 35:2881-2890 (1992).

Hutchison, Alan J. et al., "2-(Arylalkylamino)adenosin-5'-uronamides: A New Class of Highly Selective Adenosine A2 Receptor Ligands," J. Med. Chem., vol. 33:1919-1924 (1990).

Klotz, K.-N. et al., "Comparative pharmacology of human adenosine receptor subtypes—characterization of stably transfected receptors in CHO cells," Naunyn-Schmiedeberg's Arch. Pharmacol., vol. 357:1-9 (1998).

Klotz, Karl-Norbert et al., "Photoaffinity Labeling of A1-adenosine Receptors," The Journal of Biological Chemistry, vol. 260(27):14659-14664 (1985).

Knutsen, Lars J.S. et al., "N-Substituted Adenosines as Novel Neuroprotective A1 Agonists with Diminshed Hypotensive Effects," J. Med. Chem., vol. 42:3463-3477 (1999).

Kunkel, Steven L. et al., "The role of chemokines in inflammatory joint disease," Journal of Leukocyte Biology, vol. 59:6-12 (1996).

Lichtenthaler, F.W. et al., "Nucleosides, XVIII1. Improved Preparation of Nucleoside 5'-Nitrates," Synthesis, vol. 27:199-201 (1973).

Lohse, Martin J. et al., "8-Cyclopentyl-1,3-dipropylxanthine (DPCPX)—a selective high affinity antagonist radioligand for A1 adenosine receptors," Naunyn-Schmiedeberg's Arch. Pharmacol., vol. 336:204-210 (1987).

Mager, P.P. et al., "Molecular simulation applied to 2-(N'-alkylidenehydrazino)- and 2-(N'-aralkylidenehydrazino) adenosine A2 agonists," Eur. J. Med. Chem., vol. 30:15-25 (1995).

Matsuda, Akira et al., "Nucleosides and Nucleotides. 103. 2-Alkynyladenosines: A Novel Class of Selective Adenosine A2 Receptor Agonists with Potent Antihypertensive Effects," J. Med. Chem., vol. 35:241-252 (1992).

McKenzie, Sheila G. et al., "Effects of Adenosine and Related Compounds on Adenylate Cyclase and Cyclic AMP Levels in Smooth Muscle," European Journal of Pharmacology, vol. 41:193-203 (1977).

McWhinney, Charlene D. et al., "Activation of adenosine A3 receptors on macrophages inhibits tumor necrosis factor-a," European Journal of Pharmacology, vol. 310:209-216 (1996).

Missiaen, Ludwig et al., "Effect of adenine nucleosides on myo-inositol-1,4,5-trisphosphate-induced calcium release," Biochem. J., vol. 325:661-666 (1997).

Moos, Walter H. et al., "N6-Cycloalkyladenosines. Potent A1-Selective Adenosine Agonists," Journal of Medicinal Chemistry, vol. 28(10):1383-1384 (1985).

Mueller, C.E. et al., "Adenosine Receptor Ligands—Recent Developments Part I. Agonists," Current Medicinal Chemistry, vol. 7:1269-1288 (2000).

Nair, Vasu et al., "Novel, Stable Congeners of the Antiretroviral Compound 2',3'-Dideoxyadenosine," J. Am. Chem. Soc. vol. 111:8502-8504 (1989).

Niiya, Kazunori et al., "2-(N'-Alkylidenehydrazino)adenosines: Potent and Selective Coronary Vasodilators," J. Med. Chem., vol. 35:4557-4561 (1992).

Ohno, Michihiro et al., "Modulation of adenosine receptor affinity and intrinsic efficacy in adenine nucleosides substituted at the 2-position," Bioorganic & Medicinal Chemistry, vol. 12:2995-3007 (2004).

Ongini, Ennio et al., "Pharmacology of adenosine A2A receptors," TiPS, vol. 17:364-372 (1996).

Parmely, Michael J. et al., "Adenosine and a Related Carbocyclic Nucleoside Analogue Selectively Inhibit Tumor Necrosis Factor-a Production and Protect Mice against Endotoxin Challenge," The Journal of Immunology, vol. 151 (1):389-396 (1993).

Pitcher, Graham M. et al., "Paw withdrawal threshold in the von Frey hair test is influenced by the surface on which the rat stands," Journal of Neuroscience Methods, vol. 87:185-193 (1999).

Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care Med., vol. 24(5):733-742 (1996).

Reinstein, Leon J. et al., "Suppression of Lipopolysaccharide-stimulated Release of Tumor Necrosis Factor by Adenosine: Evidence for A2 Receptors on Rat Kupffer Cells," Hepatology, vol. 19:1445-1452 (1994).

Riche, Florence et al., "High tumor necrosis factor serum level is associated with increased survival in patients with abdominal septic shock: A prospective study in 59 patients," Surgery, vol. 120(5):801-807 (1996).

Rieger, Jayson M. et al., "Design, Synthesis, and Evaluation of Novel A2A Adenosine Receptor Agonists," J. Med. Chem., vol. 44:531-539 (2001).

Roelen, Harlof et al., "N6,C8-Disubstituted Adenosine Derivatives as Partial Agonists for Adenosine A1 Receptors," J. Med. Chem., vol. 39:1463-1471 (1996).

Sajjadi, Fereydoun G. et al., "Inhibition of TNF-a Expression by Adenosine," The Journal of Immunology, vol. 156:3435-3442 (1996).

Schleef, Raymond R. et al., "The Effect of Fibrin on Endothelial Cell Migration in Vitro," Tissue & Cell, vol. 14 (4):629-636 (1982).

Shuman, Dennis A. et al., "The Synthesis of Nucleoside Sulfamates Related to Nucleocidin," Journal of the American Chemical Society, vol. 92(11):3434-3440 (1970).

Thompson, Robert D. et al., "Activity of N6-Substituted 2-Chloroadenosines at A1 and A2 Adenosine Receptors," J. Med. Chem., vol. 34:3388-3390 (1991).

Van Der Wenden, Eleonora M. et al., "5'Substituted Adenosine Analogs as New High-Affinity Partial Agonists for the Adenosine A1 Receptor," J. Med. Chem., vol. 41:102-108 (1998).

Van Tilburg, Erica W. et al., "2,5'-Disubstituted Adenosine Derivatives: Evaluation of Selectivity and Efficacy for the Adenosine A1, A2A and A3 Receptor," J. Med. Chem., vol. 45:420-429 (2002).

Virag, Laszlo et al., "Effects of poly(ADP-ribose) polymerase inhibition on inflammatory cell migration in a murine model of asthma," Med. Sci. Monit., vol. 10(3):BR77-83 (2004).

Vitrori, Sauro et al., "2-Alkenyl and 2-Alkyl Derivatives of Adenosine and Adenosine-5'-N-Ethyluronamide: Different Affinity and Selectivity of E- and Z-Diastereomers at A2A Adenosine Receptors," J. Med. Chem., vol. 39:4211-4217 (1996).

Vitrori, Sauro et al., "N-Cycloalkyl Derivatives of Adenosine and 1-Deazaadenosine as Agonists and Partial Agonists of the A1 Adenosine Receptor," J. Med. Chem., vol. 43:250-260 (2000).

Viziano, Monica et al., "2-[N'-(3-Arylallylidene)hydrazino]adenosines Showing A2a Adenosine Agonist Properties and Vasodilation Activity," J. Med. Chem., vol. 38:3581-3585 (1995).

Supplementary European Search Report for Application No. 05757108, dated Jun. 4, 2007.

* cited by examiner

PURINE DERIVATIVES AS ADENOSINE $A_1$ RECEPTOR AGONISTS AND METHODS OF USE THEREOF

This application is a divisional application of U.S. patent application Ser. No. 11/137,632, filed May 25, 2005, issuing, which claims the benefit of U.S. provisional application No. 60/574,805, filed May 26, 2004, and of U.S. provisional application No. 60/588,263, filed Jul. 15, 2004, the disclosure of each of which is incorporated by reference herein in its entirety.

1. FIELD OF THE INVENTION

The invention relates to Purine Derivatives; compositions comprising an effective amount of a Purine Derivative; and methods for reducing an animal's rate of metabolism, protecting an animal's heart against myocardial damage during cardioplegia; or for treating or preventing a cardiovascular disease, a neurological disorder, an ischemic condition, a reperfusion injury, obesity, a wasting disease, or diabetes, comprising administering an effective amount of a Purine Derivative to an animal in need thereof.

2. BACKGROUND OF THE INVENTION

Adenosine is a naturally occurring purine nucleoside that is ubiquitous in mammalian cell types. Adenosine exerts its biological effects by interacting with $A_1$, $A_2$ (further subclassified as $A_{2A}$ and $A_{2B}$) and $A_3$ cell surface receptors, which modulate important physiological processes.

The $A_1$ and $A_{2A}$ receptor subtypes are believed to play complementary roles in adenosine's regulation of a cell's energy supply. Adenosine, which is a metabolic product of ATP, diffuses from the cell and locally activates the $A_1$ receptor to decrease the oxygen demand or activates the $A_{2A}$ receptor to increase the oxygen supply, thereby reinstating the balance of energy supply and demand within the tissue. The combined action of $A_1$ and $A_2$ subtypes increases the amount of available oxygen to tissue and protects cells against damage caused by a short-term imbalance of oxygen. One of the important functions of endogenous adenosine is to prevent tissue damage during traumas such as hypoxia, an ischemic condition, hypotension and seizure activity.

In addition, modulation of $A_1$ receptors slows conduction velocity in the heart's atrioventricular node, resulting in the normalization of supraventricular tachycardias and control of ventricular rate during atrial fibrillation and flutter. Modulation of $A_{2A}$ receptors also regulates coronary vasodilation.

Adenosine is also a neuromodulator, which modulates molecular mechanisms underlying many aspects of physiological brain function by mediating central inhibitory effects. An increase in neurotransmitter release follows traumas such as hypoxia, ischemia and seizures. Neurotransmitters are ultimately responsible for neural degeneration and neural death, which can cause brain damage or death. Adenosine is thought to be an endogenous anticonvulsant agent that inhibits glutamate release from excitory neurons and neuronal firing. Adenosine agonists, therefore, are useful as antiepileptic agents.

Adenosine plays an important role as a cardioprotective agent. Levels of endogenous adenosine increase in response to ischemia and hypoxia and protect cardiac tissue during and after trauma (preconditioning). Adenosine agonists thus are useful as cardioprotective agents.

The preparation and use of a number of adenosine $A_1$ receptor agonists have been described (Moos et al., J. Med. Chem. 28:1383-1384 (1985); Thompson et al., J. Med. Chem. 34:3388-3390 (1991); Vittori et al., J. Med. Chem. 43:250-260 (2000); Roelen et al., J. Med. Chem., 39:1463-1471 (1996); van der Wenden et al., J. Med. Chem. 41102-108 (1998); Dalpiaz et al., Pharm. Res. 18:531-536 (2001), Beakers et al., J. Med. Chem. 46, 1492-1503 (2003); U.S. Pat. No. 5,589,467 to Lau et al.; U.S. Pat. No. 5,789,416, to Lum et al.; and C. E. Muller, Current Medicinal Chemistry 2000, 7, 1269-1288).

Nucleoside 5'-nitrate esters are reported in Lichtenthaler et al., Synthesis, 199-201 (1974), and U.S. Pat. No. 3,832,341 to Duchinsky et al.

The citation of any reference in Section 2 of this application is not an admission that the reference is prior art to this application.

3. SUMMARY OF THE INVENTION

In one embodiment, the invention provides compounds having the Formula (Ia):

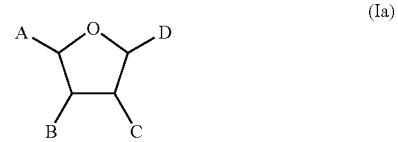

and pharmaceutically acceptable salts thereof,
wherein
A is —CH$_2$OSO$_2$NH$_2$;
B and C are —OH;
D is:

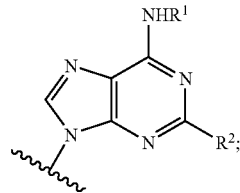

A and B are trans with respect to each other;
B and C are cis with respect to each other;
C and D are cis or trans with respect to each other;
R$^1$ is —C$_3$-C$_8$ monocyclic cycloalkyl, —C$_3$-C$_8$ monocyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —C$_8$-C$_{12}$ bicyclic cycloalkyl, or —C$_8$-C$_{12}$ bicyclic cycloalkenyl;
R$^2$ is -halo, —CN, —NHR$^8$, —OR$^8$, —SR$^8$, —NHC(O) OR$^8$, —NHC(O)R$^4$, —NHC(O)NHR$^8$, —NHNHC(O)R$^4$, —NHNHC(O)OR$^8$, —NHNHC(O)NHR$^8$, or —NH—N═C (R$^6$)R$^7$;
R$^4$ is —H, —C$_1$-C$_{15}$ alkyl, -aryl, —(CH$_2$)$_n$-aryl, —(CH$_2$)$_n$- (3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_9$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^6$ is —C$_1$-C$_{10}$ alkyl, -aryl, —(CH$_2$)$_n$-aryl, —(CH$_2$)$_n$— (C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);

R$^7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), or —(CH$_2$)$_n$-(8- to 12-membered bicyclic heterocycle);

R$^8$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl; and each n is independently an integer ranging from 1 to 5.

In another embodiment, the invention provides compounds having the Formula (Ib):

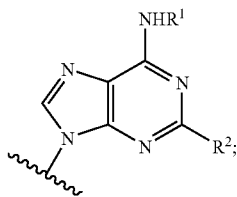

(Ib)

and pharmaceutically acceptable salts thereof, wherein

A is —CH$_2$ONO$_2$;
B and C are —OH;
D is

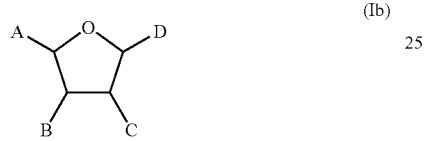

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

R$^2$ is —CN, —NHR$^4$, —NHC(O)R$^4$, —NHC(O)OR$^4$, —NHC(O)NHR$^4$, —NHNHC(O)R$^4$, —NHNHC(O)OR$^4$, —NHNHC(O)NHR$^4$, or —NH—N=C(R$^6$)R$^7$;

R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkenyl), -phenylene-(CH$_2$)$_n$COOH, or -phenylene-(CH$_2$)$_n$COO—(C$_1$-C$_{10}$ alkyl);

R$^7$ is —H, —C$_1$-C$_{10}$ alkyl, -aryl, —(CH$_2$)$_n$-aryl, —(CH$_2$)$_n$ -(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkenyl) or —(CH$_2$)$_n$—(C$_8$-C$_{12}$ bicyclic cycloalkyl); and each n is independently an integer ranging from 1 to 5.

In still another embodiment, the invention provides compounds having the Formula (Ic):

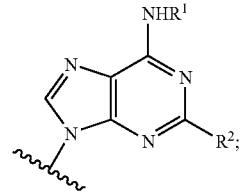

(Ic)

and pharmaceutically acceptable salts thereof, wherein

A is —CH$_2$NHR$^5$;
B and C are —OH;
D is

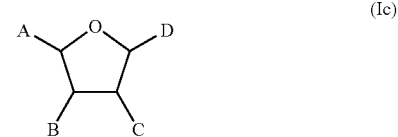

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

R$^2$ is —NHR$^4$, —OR$^4$, —SR$^4$, —NHC(O)R$^4$, —NHC(O)OR$^4$, —NHC(O)NHR$^4$, —NHNHC(O)R$^4$, —NHNHC(O)NHR$^4$, or —NHNHC(O)OR$^4$;

R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^5$ is —C(O)O(C$_1$-C$_{10}$ alkyl), —C(O)NH(C$_1$-C$_{10}$ alkyl), —C(O)N(C$_1$-C$_{10}$ alkyl)$_2$, —C(O)NH-aryl, —CH(NH$_2$)NH$_2$ or —CH(NH$_2$)NH(C$_1$-C$_{10}$ alkyl); and each n is independently an integer ranging from 1 to 5.

In a further embodiment, the invention provides compounds having the Formula (Id):

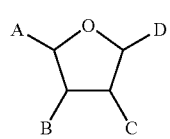
(Id)

and pharmaceutically acceptable salts thereof,
wherein
A is —$R^3$;
B and C are —OH;
D is

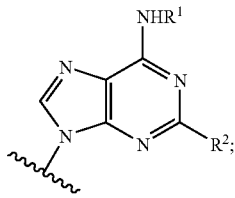

A and B are trans with respect to each other;
B and C are cis with respect to each other;
C and D are cis or trans with respect to each other;
$R^1$ is —H, —$C_1$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_3$-$C_8$ monocyclic cycloalkenyl, —$C_8$-$C_{12}$ bicyclic cycloalkyl, —$C_8$-$C_{12}$ bicyclic cycloalkenyl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
$R^2$ is —H, -halo, —CN, —$NHR^4$, —$OR^4$, —$SR^4$, —NHC(O)$R^4$, —NHC(O)O$R^4$, —NHC(O)NH$R^4$, NHNHC(O)$R^4$, —NHNHC(O)NH$R^4$, —NHNHC(O)O$R^4$ or —NH—N=C($R^6$)$R^7$;
$R^3$ is —$CH_2ONO$ or —$CH_2OSO_3H$;
$R^4$ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;
$R^6$ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), —$(CH_2)_n$-(8- to 12-membered bicyclic heterocycle), -phenylene-$(CH_2)_n$COOH, or -phenylene-$(CH_2)_n$COO—($C_1$-$C_{10}$ alkyl);
$R^7$ is —H, —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), or —$(CH_2)_n$-(8- to 12-membered bicyclic heterocycle); and
each n is independently an integer ranging from 1 to 5.

In a further embodiment, the invention provides compounds having the Formula (Ie):

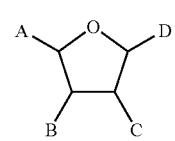
(Ie)

and pharmaceutically acceptable salts thereof,
wherein
A is —$CH_2R^3$;
B and C are —OH;
D is

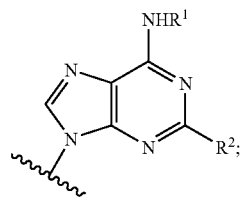

A and B are trans with respect to each other;
B and C are cis with respect to each other;
C and D are cis or trans with respect to each other;
$R^1$ is -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
$R^2$ is -halo, —CN, —$NHR^4$, —$OR^4$, —$SR^4$, —NHC(O)$R^4$, —NHC(O)O$R^4$, —NHC(O)NH$R^4$, NHNHC(O)$R^4$, —NHNHC(O)O$R^4$, —NHNHC(O)NH$R^4$, or —NH—N=C($R^6$)$R^7$;
$R^3$ is —$OSO_2NH(C_1$-$C_{10}$ alkyl), —$OSO_2N(C_1$-$C_{10}$ alkyl)$_2$, or —$OSO_2NH$-aryl, where each $C_1$-$C_{10}$ alkyl is independent;
$R^4$ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;
$R^6$ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), —$(CH_2)_n$-(8- to 12-membered bicyclic heterocycle), -phenylene-$(CH_2)_n$COOH, or -phenylene-$(CH_2)_n$COO—($C_1$-$C_{10}$ alkyl);
$R^7$ is —H, —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), or —$(CH_2)_n$-(8- to 12-membered bicyclic heterocycle); and
each n is independently an integer ranging from 1 to 5.

In another embodiment, the invention provides compounds having the Formula (If):

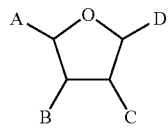
(If)

and pharmaceutically acceptable salts thereof,
wherein
A is —CH$_2$ONO$_2$;
B and C are —OH;
D is

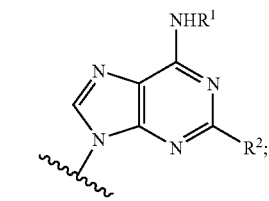

A and B are trans with respect to each other;
B and C are cis with respect to each other;
C and D are cis or trans with respect to each other;
R$^1$ is —C$_3$-C$_8$ monocyclic cycloalkyl; and
R$^2$ is —H or -halo.

In another embodiment, the invention provides compounds having the Formula (Ig):

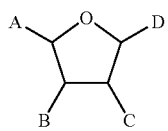
(Ig)

and pharmaceutically acceptable salts thereof,
wherein
A is —CH$_2$ONO$_2$;
B and C are —OH;
D is

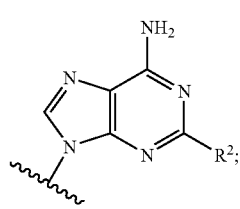

A and B are trans with respect to each other;
B and C are cis with respect to each other;
C and D are cis or trans with respect to each other; and
R$^2$ is —H or -halo.

In another embodiment, the invention provides compounds having the Formula (Ih):

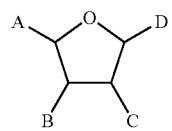
(Ih)

and pharmaceutically acceptable salts thereof,
wherein
A is —CH$_2$ONO$_2$;
B and C are —OH;
D is

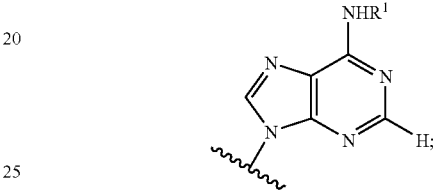

A and B are trans with respect to each other;
B and C are cis with respect to each other; and
C and D are cis or trans with respect to each other; and
R$^1$ is cyclopent-1-ol-2-yl, or cyclopent-1-ol-3-yl.

In another embodiment, the invention provides compounds having the Formula (II):

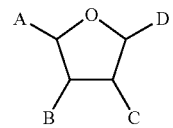
(II)

and pharmaceutically acceptable salts thereof,
wherein
A is —CH$_2$OH;
B and C are —H;
D is

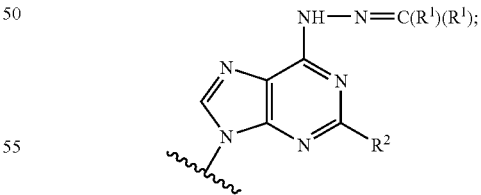

A and B are trans with respect to each other;
B and C are cis with respect to each other;
C and D are cis or trans with respect to each other;
each R$^1$ is independently —H, —C$_1$-C$_{10}$ alkyl, —(CH$_2$)$_m$-(3- to 7-membered monocyclic heterocycle), —(CH$_2$)$_m$-(8- to 12-membered bicyclic heterocycle), —(CH$_2$)$_m$—(C$_8$-C$_{12}$ bicyclic cycloalkyl), —(CH$_2$)$_m$—(C$_8$-C$_{12}$ bicyclic cycloalkenyl), or —(CH$_2$)$_n$-aryl, or both R$^1$ groups together with the carbon atom to which they are attached form a —C$_3$-C$_8$ monocyclic cycloalkyl, a —$C_3$-$C_8$ monocyclic cycloalkenyl, a —$C_8$-$C_{12}$ bicyclic cycloalkyl, or a —$C_8$-$C_{12}$ bicyclic cycloalkenyl;

$R^2$ is —$OR^4$, —$SR^4$, —$NHNHC(O)R^3$, —$NHNHC(O)NHR^3$, —$NHC(O)OR^7$, or —NH—N=$C(R^5)R^6$;

$R^3$ is —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, —O—$(CH_2)_n$—($C_8$-$C_{12}$ bicyclic cycloalkyl), —O—$(CH_2)_n$—($C_3$-$C_8$ monocyclic cycloalkyl), O—$(CH_2)_n$—($C_3$-$C_8$ monocyclic cycloalkenyl), —C≡C—($C_1$-$C_{10}$ alkyl) or —C≡C-aryl;

$R^4$ is —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_9$-$C_{12}$ bicyclic cycloalkyl), —$(CH_2)_n$-aryl, or —C≡C-aryl;

$R^5$ and $R^6$ are each independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, -phenylene-$(CH_2)_n$COOH, or -phenylene-$(CH_2)_n$COO—($C_1$-$C_{10}$ alkyl), or $R^5$ and $R^6$ together with the carbon atom to which they are attached form a $C_3$-$C_8$ monocyclic cycloalkyl or a $C_8$-$C_{12}$ bicyclic cycloalkyl;

$R^7$ is —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, —C≡C—($C_1$-$C_{10}$ alkyl) or —C≡C-aryl;

m is an integer ranging from 0 to 3; and each n is independently an integer ranging from 0 to 5.

In still another embodiment, the invention provides compounds having the Formula (III):

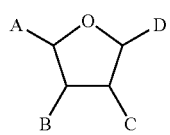

(III)

and pharmaceutically acceptable salts thereof, wherein

A is —$CH_2R^3$;

B and C are —OH;

D is

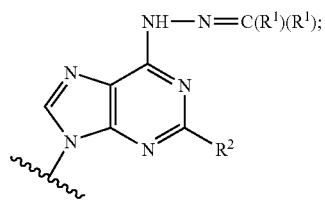

A and B are trans with respect to each other;

B and C are cis with respect to each other;

C and D are cis or trans with respect to each other;

each $R^1$ is independently —H, —$C_1$-$C_{10}$ alkyl, —$(CH_2)_m$-(3- to 7-membered monocyclic heterocycle), —$(CH_2)_m$-(8- to 12-membered bicyclic heterocycle), —$(CH_2)_m$—($C_3$-$C_8$ monocyclic cycloalkyl), —$(CH_2)_m$—($C_3$-$C_8$ monocyclic cycloalkenyl), —$(CH_2)_m$—($C_8$-$C_{12}$ bicyclic cycloalkyl), —$(CH_2)_n$—($C_8$-$C_{12}$ bicyclic cycloalkenyl), or —$(CH_2)_m$-aryl, or two $R^1$ groups, together with the carbon atom to which they are attached, form a —$C_3$-$C_8$ monocyclic cycloalkyl, a —$C_3$-$C_8$ monocyclic cycloalkenyl, a —$C_8$-$C_{12}$ bicyclic cycloalkyl, or a —$C_8$-$C_{12}$ bicyclic cycloalkenyl;

$R^2$ is —H, —CN, -halo, —$N(R^4)_2$, —$OR^4$, —$SR^4$, —NHC(O)$R^4$, —NHC(O)O$R^4$, —NHC(O)NH$R^4$, —NHNHC(O)$R^4$, —NHNHC(O)NH$R^4$, —NHNHC(O)O$R^4$, or —NH—N=$C(R^6)R^7$;

$R^3$ is —$ONO_2$, —ONO, —$OSO_3H$, —$OSO_2NH_2$, —$OSO_2NH(C_1$-$C_{10}$ alkyl), —$OSO_2N(C_1$-$C_{10}$ alkyl)$_2$, —$OSO_2NH$-aryl or —$N(R^5)_2$;

each $R^4$ is independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, —C(O)O($C_1$-$C_{10}$ alkyl), —C(O)NH($C_1$-$C_{10}$ alkyl), —C(O)N($C_1$-$C_{10}$ alkyl)$_2$, —C(O)NH-aryl, —C(O)N($C_1$-$C_{10}$ alkyl)$_2$, —CH($NH_2$)$NH_2$ or —CH($NH_2$)NH($C_1$-$C_{10}$ alkyl);

each $R^5$ is independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl) or —$(CH_2)_n$-aryl;

$R^6$ and $R^7$ are each independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, -phenylene-$(CH_2)_n$COOH, or -phenylene-$(CH_2)_n$COO—($C_1$-$C_{10}$ alkyl), or $R^6$ and $R^7$, together with the carbon atom to which they are attached, form a —$C_3$-$C_8$ monocyclic cycloalkyl, —$C_3$-$C_8$ monocyclic cycloalkenyl, or a $C_8$-$C_{12}$ bicyclic cycloalkenyl;

m is an integer ranging from 0 to 3; and each n is independently an integer ranging from 0 to 5.

In a further embodiment, the invention provides compounds having the Formula (IV):

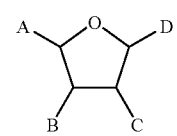

(IV)

and pharmaceutically acceptable salts thereof, wherein

A is —CH$_2$OH;

B and C are —OH;

D is

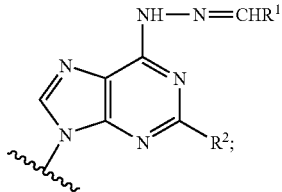

A and B are trans with respect to each other;

B and C are cis with respect to each other;

C and D are cis or trans with respect to each other;

R$^1$ is —C$_3$-C$_8$ monocyclic cycloalkyl or —C$_3$-C$_8$ monocyclic cycloalkenyl;

R$^2$ is —H, -halo, —CN, —OR$^3$, —SR$^3$, —N(R$^3$)$_2$, —NHNHC(O)R$^3$, —NHNHC(O)NHR$^3$, —NHNHC(O)OR$^3$, or —NH—N=C(R$^4$)R$^5$;

each R$^3$ is independently —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, —C≡C—(C$_1$-C$_{10}$ alkyl) or —C≡C-aryl;

R$^4$ and R$^5$ are each independently —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, -phenylene-(CH$_2$)$_n$COOH, or -phenylene-(CH$_2$)$_n$COO—(C$_1$-C$_{10}$ alkyl), or R$^4$ and R$^5$ together with the carbon atom to which they are attached form a C$_3$-C$_8$ monocyclic cycloalkyl, a C$_3$-C$_8$ monocyclic cycloalkenyl, a —C$_8$-C$_{12}$ bicyclic cycloalkyl, or a —C$_8$-C$_{12}$ bicyclic cycloalkenyl; and each n is independently an integer ranging from 0 to 5.

In another embodiment, the invention provides compounds having the Formula (V):

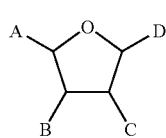

(V)

and pharmaceutically acceptable salts thereof, wherein

A is —CH$_2$OH;

B and C are —OH;

D is

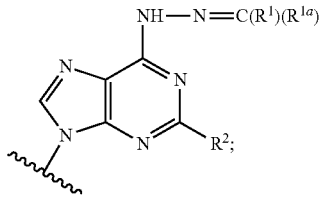

A and B are trans with respect to each other;

B and C are cis with respect to each other;

C and D are cis or trans with respect to each other;

R$^1$ is —C$_1$-C$_{10}$ alkyl, —(CH$_2$)$_m$-(3- to 7-membered monocyclic heterocycle), —(CH$_2$)$_m$-(8- to 12-membered bicyclic heterocycle), —(CH$_2$)$_m$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkyl), —(CH$_2$)$_m$—(C$_3$-C$_8$ monocyclic cycloalkenyl) or —(CH$_2$)$_m$-aryl, or R$^1$ and R$^{1a}$ together with the carbon atom to which they are attached form a —C$_3$-C$_8$ monocyclic cycloalkyl, a —C$_3$-C$_8$ monocyclic cycloalkenyl, a —C$_8$-C$_{12}$ bicyclic cycloalkyl, or a —C$_8$-C$_{12}$ bicyclic cycloalkenyl;

R$^{1a}$ is —C$_3$-C$_8$ monocyclic cycloalkyl or —C$_3$-C$_8$ monocyclic cycloalkenyl;

R$^2$ is —OR$^4$, —SR$^4$, —NHNHC(O)R$^3$, —NHNHC(O)NHR$^3$, —NHNHC(O)OR$^3$, or —NH—N=C(R$^5$)R$^6$;

R$^3$ is —H, —C$_1$-C$_{10}$ alkyl, —(CH$_2$)$_n$-(3- to 7-membered monocyclic heterocycle), —(CH$_2$)$_n$-(8- to 12-membered bicyclic-heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, —C≡C—(C$_1$-C$_{10}$ alkyl) or —C≡C-aryl;

R$^4$ is —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$-aryl, —C≡C—(C$_1$-C$_{10}$ alkyl) or —C≡C-aryl;

R$^5$ and R$^6$ are each independently —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, -phenylene-(CH$_2$)$_n$COOH, or -phenylene-(CH$_2$)$_n$COO—(C$_1$-C$_{10}$ alkyl), or R$^5$ and R$^6$ together with the carbon atom to which they are attached form a C$_3$-C$_8$ monocyclic cycloalkyl, a C$_3$-C$_8$ monocyclic cycloalkenyl, a —C$_8$-C$_{12}$ bicyclic cycloalkyl, or a —C$_8$-C$_{12}$ bicyclic cycloalkenyl;

m is an integer ranging from 0 to 3; and each n is independently an integer ranging from 0 to 5.

A compound of Formula (Ia), (Ib), (Ic), (Id), (Ie), (If), (Ig), (Ih), (II), (III), (IV) or (V) or a pharmaceutically acceptable salt thereof, (a "Purine Derivative") is useful for: (i) treating or preventing a cardiovascular disease, a neurological disorder, an ischemic condition, a reperfusion injury, obesity, a wasting disease, or diabetes (each being a "Condition"); (ii) reducing an animal's rate of metabolism; or (iii) protecting an animal's heart against myocardial damage during cardioplegia The invention also provides compositions comprising an effective amount of a Purine Derivative and a physiologically acceptable carrier or vehicle. The compositions are useful for: (i) treating or preventing a Condition; (ii) reducing an animal's rate of metabolism; or (iii) protecting an animal's heart against myocardial damage during cardioplegia.

The invention further provides methods for: (i) treating or preventing a Condition; (ii) reducing an animal's rate of metabolism; or (iii) protecting an animal's heart against myocardial damage during cardioplegia, comprising administering an effective amount of a Purine Derivative to an animal in need thereof.

The details of the invention are set forth in the accompanying description below. Other features, objects, and advantages of the invention will be apparent from the description and from the claims. All patents, patent applications and publications cited in this specification are incorporated herein by reference for all purposes.

4. BRIEF DESCRIPTION OF THE DRAWINGS

FIG. 1 shows the effect of Compound 17 on lipopolysaccharide induced plasma TNF and MIP production in male BALB/c mice. The unshaded bars represent LPS, administered i.p. at a dose of 1 mg/kg and the shaded bars represent Compound 17, administered orally at a dose of 0.03 mg/kg, followed 30 minutes later by LPS, administered i.p. at a dose of 1 mg/kg. TNF and MIP levels were measured 90 minutes after LPS administration.

Figure 4:
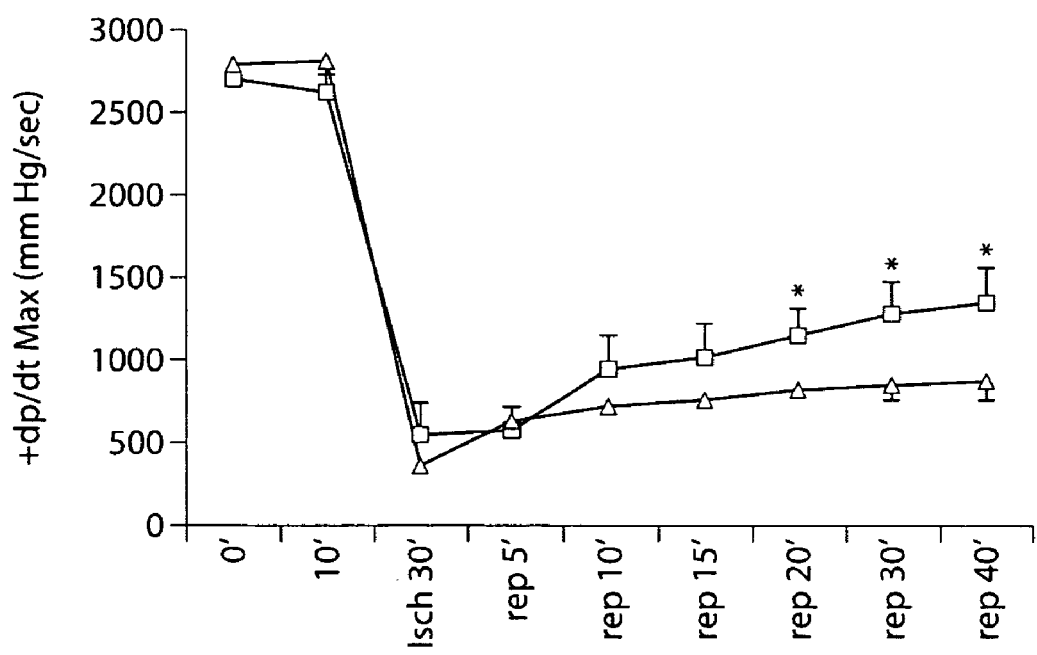
Figure 5:
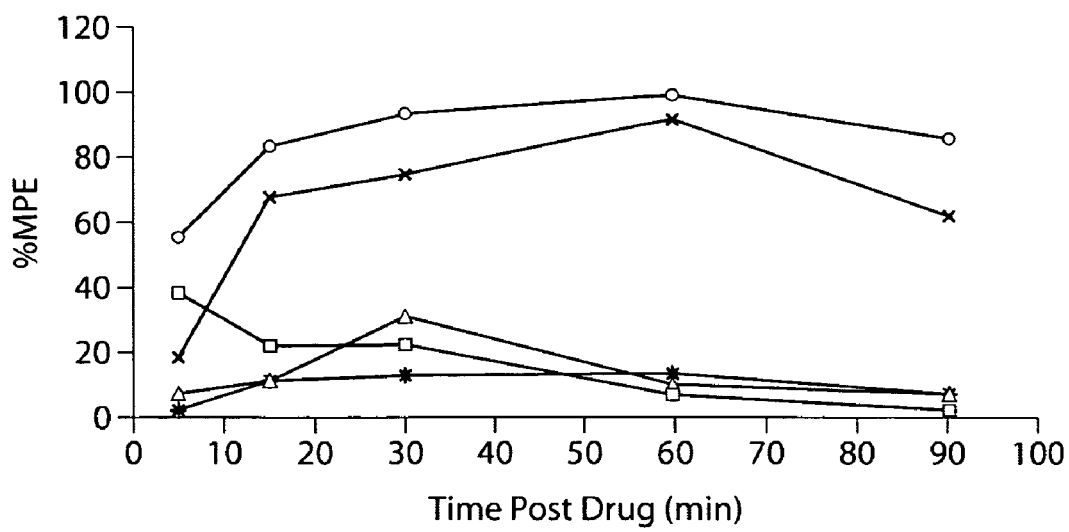

FIG. 4 shows the effect of Compound 17 on function recovery in isolated perfused rat hearts after 30 minute no-flow ischemia followed by 40 minute reperfusion. Line -▲- represents a non-treated control group (n=13) and line -■- represents administration (n=9) of Compound 17 at a concentration of 1 nM, administered 10 minutes prior to induction of ischemia FIG. 5 shows the effect of Compound 17 and/or buprenorphine in an acute pain model in mice using a tail flick assay. The X-axis represents Maximum Possible Effect (MPE) and the Y-axis represents time after administration of Compound 17 and/or buprenorphine. Line -●- represents co-administration of buprenorphine (1.0 mg/kg) and Compound 17 (3.0 mg/kg), line -■- represents buprenorphine (1.0 mg/kg), line -▲- represents Compound 17 (3.0 mg/kg), line —X— represents co-administration of buprenorphine (0.3 mg/kg) and Compound 17 (3.0 mg/kg), and line -✕- represents buprenorphine (0.3 mg/kg).

Figure 6:
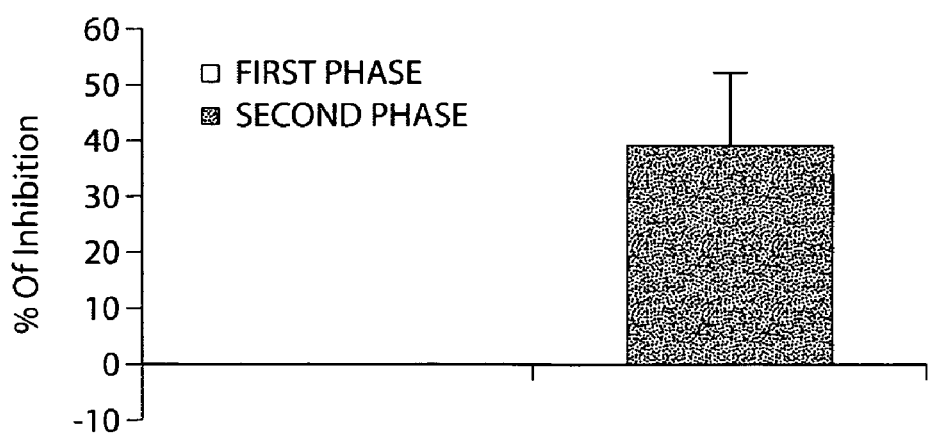

FIG. 6 shows the effect of Compound 17 in a mouse formalin pain model pain. The bar graph from left to right shows the first phase of the test (no response) and the second phase of the test (shaded bar).

Figure 7:
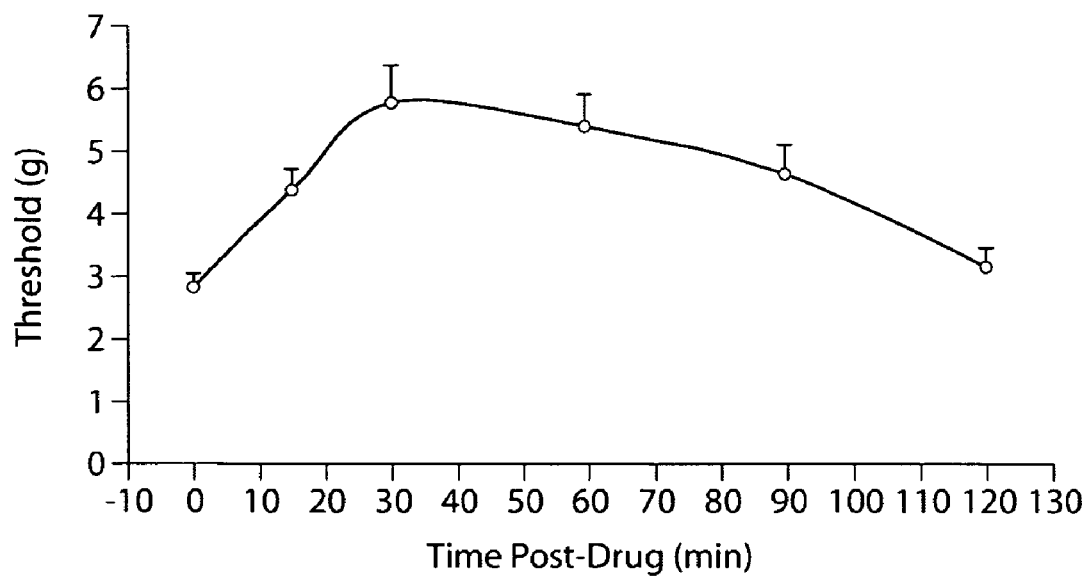

FIG. 7 shows the effect of Compound 17 on allodynia in a mouse model of diabetic neuropathy. The X-axis represents the animal's pain threshold and the Y-axis represents time after administration of Compound 17. Line -●- represents treatment with Compound 17 (1.0 mg/kg).

Figure 8:
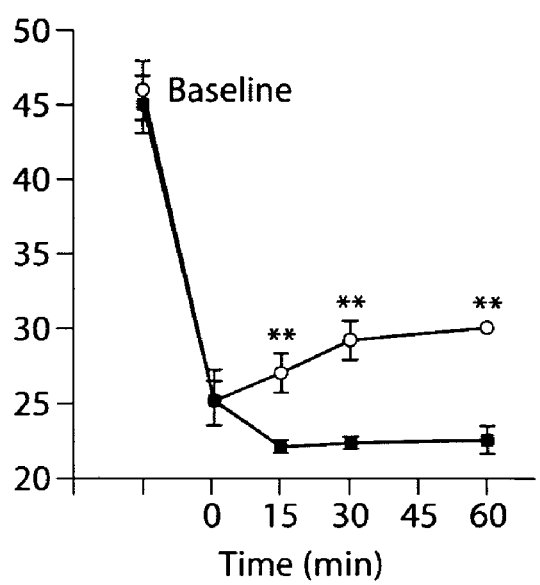

FIG. 8 shows the effect of Compound 17 on mechanically induced pain threshold in a carrageenan rat model. The X-axis represents the animal's pain threshold and the Y-axis represents time after administration of Compound 17. Line -○- represents vehicle and line -■-represents Compound 17 (5.0 mg/kg).

Figure 9:
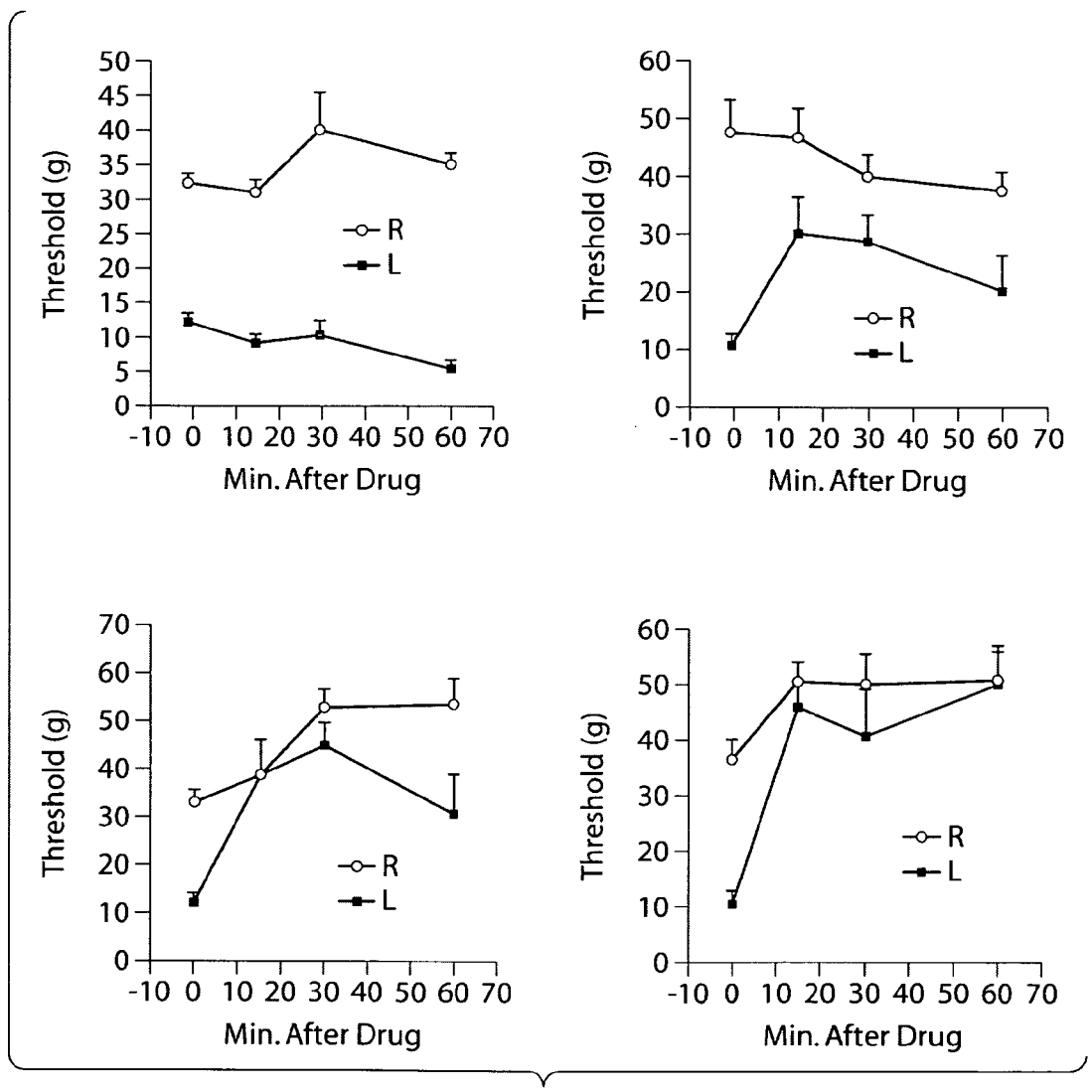

FIG. 9 shows the effect of Compound 17 and/or buprenorphine on pain threshold in a mouse model of sciatic nerve ligation. The k-axis represents the animal's pain threshold and the Y-axis represents time after administration of Compound 17 and or buprenorphine. The top left graph shows the effect of vehicle, the top right graph shows the effect of Compound 17 (0.1 mg/kg), the bottom left graph shows the effect of buprenorphine (0.3 mg/kg) and the bottom right graph shows the effect of co-administration of Compound 17 (0.1 mg/kg) and buprenorphine (0.3 mg/kg). Line -♦- represents the response of the control leg and line -■- represents the response of the treated leg.

5. DETAILED DESCRIPTION OF THE INVENTION

5.1 Definitions

The term "$C_1$-$C_{15}$ alkyl" as used herein refers to a straight or branched chain, saturated hydrocarbon having from 1 to 15 carbon atoms. Representative $C_1$-$C_{15}$ alkyl groups include, but are not limited to methyl, ethyl, propyl, isopropyl, butyl, sec-butyl, tert-buty, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl, neodecyl, undecyl, dodecyl, tridecyl, tetradecyl and pentadecyl. In one embodiment, the $C_1$-$C_{15}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{15}$ alkyl is unsubstituted.

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O— ($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted.

The term "$C_1$-$C_6$ alkyl" as used herein refers to a straight or branched chain, saturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, and neohexyl. Unless indicated, the $C_1$-$C_6$ alkyl is unsubstituted.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, -1,3,5-cycloheptatrienyl, cyclooctenyl, 1,3-cyclooctadienyl, 1,4-cyclooctadienyl, -1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl.

Unless indicated, the $C_8$-$C_{12}$ bicyclic cycloalkyl is unsubstituted.

The term "$C_8$-$C_{12}$ bicyclic cycloalkenyl" as used herein is a 8-, 9-, 10-, 11- or 12-membered non-aromatic bicyclic cycloalkyl ring system, having at least one endocyclic double bond. It is to be understood that when any two groups, together with the carbon atom to which they are attached form a $C_8$-$C_{12}$ bicyclic cycloalkenyl group, the carbon atom to which the two groups are attached remains tetravalent. Representative $C_8$-$C_{12}$ bicyclic cycloalkenyl groups include, but are not limited to, octahydronaphthalene, hexahydronaphthalene, hexahydroindene, tetrahydroindene, octahydrobenzocycloheptene, hexahydrobenzocycloheptene, tetrahydrobenzocycloheptene, decahydroheptalene, octahydroheptalene, hexahydroheptalene, and tetrahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkenyl is unsubstituted.

The term "effective amount" as used herein refers to an amount of a Purine Derivative that is effective for: (i) treating or preventing a Condition; (ii) reducing an animal's rate of metabolism; or (iii) protecting an animal's heart against myocardial damage during cardioplegia.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle-group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, -piperidinyl, pyranyl, pyrazinyl, pyrazolidinyl, pyrazolinyl, pyrazolyl, pyridazinyl, pyridooxazole, pyridoimuidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 3- to 7-membered monocyclic heterocycle is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 14 of its ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered monocyclic heterocycles are attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the -8- to 12-membered bicyclic heterocycle group can substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 8- to 12-membered bicyclic heterocycle is unsubstituted.

Representative examples of a "phenylene group" are depicted below:

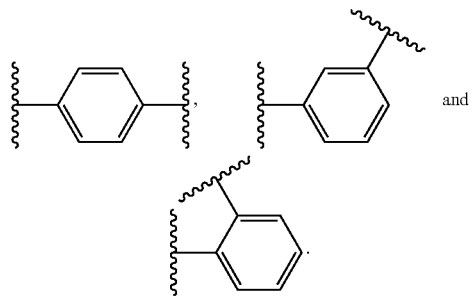

The phrase "pharmaceutically acceptable salt," as used herein, is a salt of an acid and a basic nitrogen atom of a Purine Derivative. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a Purine Derivative having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a Purine Derivative.

An "animal" is a mammal, e.g., a human, mouse, rat, guinea pig, dog, cat, horse, cow, pig, or non-human primate, such as a monkey, chimpanzee, baboon or rhesus. In one embodiment, an animal is a human.

The term "isolated and purified" as used herein means separate from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Purine Derivative by weight of the isolate. In one embodiment, the isolate contains at least 95% of a Purine Derivative by weight of the isolate.

The term "substantially free of its corresponding opposite enantiomer" as used herein, means that a Purine Derivative contains no more than about 10% by weight of its corresponding opposite enantiomer. In one embodiment the Purine Derivative that is substantially free of its corresponding opposite enantiomer contains no more than about 5% by weight of its corresponding opposite enantiomer. In a further embodiment a Purine Derivative that is substantially free of its corresponding opposite enantiomer contains no more than about 1% by weight of its corresponding opposite enantiomer. In another embodiment a Purine Derivative that is substantially free of its corresponding opposite enantiomer contains no more than about 0.5% by weight of its corresponding opposite enantiomer. In still another embodiment a Purine Derivative that is substantially free of its corresponding opposite enantiomer contains no more than about 0.1% by weight of its corresponding opposite enantiomer.

The term "substantially free of its corresponding other anomer" as used herein, means that a Purine Derivative contains no more than about 10% by weight of its corresponding other anomer. In one embodiment the Purine Derivative that is substantially free of its corresponding other anomer contains no more than about 5% by weight of its corresponding other anomer. In a further embodiment a Purine Derivative that is substantially free of its corresponding other anomer contains no more than about 1% by weight of its corresponding other anomer. In another embodiment a Purine Derivative that is substantially free of its corresponding other anomer contains no more than about 0.5% by weight of its corresponding other anomer. In still another embodiment a Purine Derivative that is substantially free of its corresponding other anomer contains no more than about 0.1% by weight of its corresponding other anomer.

Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached. For example, in the illustration below:

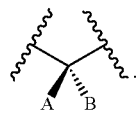

group A is above the plane of the carbon atom to which it is attached and group B is below the plane of the carbon atom to which it is attached.

The following abbreviations are used herein and have the indicated definitions: $Ac_2O$ is acetic anhydride; ATP is adenosine triphosphate; CCPA is 2-chloro-$N^6$-cyclopentyladenosine; CPA is $N^6$-cyclopentyladenosine; CSA is camphorsulfonic acid; CHO is chinese hamster ovary; DMF is N,N-dimethylformamide; EGTA is ethylene glycol bis(3-aminoethyl ether)-N,N,N',N'-tetraacetic acid; $EtNH_2$ is ethylamine; EtOAc is ethyl acetate; EtOH is ethanol; LiHMDS is lithium hexamethyldisilazide; MeOH is methanol; MS is mass spectrometry; NECA is adenosine-5'-(N-ethyl)carboxamido; NMR is nuclear magnetic resonance; R-PIA is $N^6$-(2-phenyl-isopropyl) adenosine, R-isomer; TFA is trifluoroacetic acid; THF is tetrahydrofuran; TMSOTf is trimethylsilyl trifluoromethanesulfonate.

5.2 The Purine Derivatives

5.2.1 The Purine Derivatives of Formula (Ia)

As stated above, the present invention encompasses Purine Derivatives having the Formula (Ia):

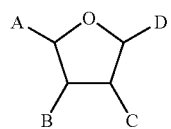

(Ia)

wherein A, B, C and D are defined above for the Purine Derivatives of Formula (Ia), and A and B are trans with respect to each other; B and C are cis with respect to each other; and C and D are cis or trans with respect to each other.

In one embodiment, $R^1$ is —$C_3$-$C_8$ monocyclic cycloalkyl.

In a specific embodiment, $R^1$ is cyclopentyl.

In another embodiment, $R^1$ is —$C_3$-$C_8$ monocyclic cycloalkenyl.

In another embodiment, $R^1$ is —$C_8$-$C_{12}$ bicyclic cycloalkyl or —$C_8$-$C_{12}$ bicyclic cycloalkenyl.

In still another embodiment, $R^1$ is —$(CH_2)_n$—($C_3$-$C_8$ monocyclic cycloalkyl) or —$(CH_2)_n$—($C_3$-$C_8$ monocyclic cycloalkenyl).

In one embodiment, $R^2$ is -halo.

In a specific embodiment, $R^2$ is —Cl.

In another embodiment, $R^2$ is —CN.

In another embodiment, $R^2$ is —$NHR^8$, —$OR^8$ or —$SR^8$.

In a further embodiment, $R^2$ is —$NHC(O)R^4$, —$NHC(O)OR^8$ or —$NHC(O)NHR^8$.

In another embodiment, $R^2$ is —$NHNHC(O)R^4$, —$NHNHC(O)OR^8$ or —$NHNHC(O)NHR^8$. In yet another embodiment, $R^2$ is —NH—N=$C(R^6)R^7$.

In one embodiment, C and D are cis with respect to each other.

In another embodiment, C and D are trans with respect to each other.

The present invention also provides compositions comprising an effective amount of a Purine Derivative of Formula (Ia) and a physiologically acceptable carrier or vehicle.

The invention further provides Purine Derivatives of Formula (Ia) that are in isolated and purified form.

The invention still further provides methods for treating or preventing a Condition, comprising administering an effective amount of a Purine Derivative of Formula (Ia) to an animal in need thereof.

The invention further provides methods for reducing an animal's rate of metabolism, comprising administering an effective amount of a Purine Derivative of Formula (Ia) to an animal in need thereof.

The invention further provides methods for protecting an animal's heart against myocardial damage during cardioplegia, comprising administering an effective amount of a Purine Derivative of Formula (Ia) to an animal in need thereof.

The Purine Derivatives of Formula (Ia) can exist in the form of a single enantiomer, for example, that depicted by either the Formula (Ia') or Formula (Ia"):

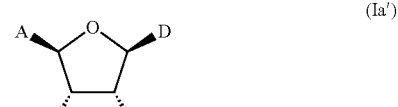

(Ia')

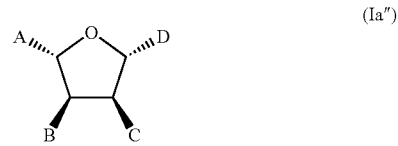

(Ia")

wherein A, B, C and D are defined above for the Purine Derivatives of Formula (Ia).

A Purine Derivative of Formula (Ia') is the corresponding opposite enantiomer of a Purine Derivative of Formula (Ia") when group A of the Purine Derivative of Formula (Ia') is the same as group A of the Purine Derivative of Formula (Ia") and when group D of the Purine Derivative of Formula (Ia') is the same as group D of the Purine Derivative of Formula (Ia").

A Purine Derivative of Formula (Ia") is the corresponding opposite enantiomer of a Purine Derivative of Formula (Ia") when group A of the Purine Derivative of Formula (Ia") is the same as group A of the Purine Derivative of Formula (Ia') and when group D of the Purine Derivative of Formula (Ia") is the same as group D of the Purine Derivative of Formula (Ia').

In one embodiment, the Purine Derivatives of Formula (Ia) have the formula (Ia'), depicted above, wherein A, B, C and D are defined above for the Purine Derivatives of Formula (Ia), and wherein the Purine Derivatives of Formula (Ia') are substantially free of their corresponding opposite enantiomer.

In another embodiment, the Purine Derivatives of Formula (Ia) have the formula (Ia"), depicted above, wherein A, B, C and D are defined above for the Purine Derivatives of Formula (Ia), and wherein the Purine Derivatives of Formula (Ia") are substantially free of their corresponding opposite enantiomer.

In another embodiment, the Purine Derivatives of Formula (Ia) exist as a mixture of a Purine Derivative of Formula (Ia') and a Purine Derivative of Formula (Ia") wherein the amount of the Purine Derivative of Formula (Ia') exceeds the amount of the Purine Derivative of Formula (Ia").

In a further embodiment, the Purine Derivatives of Formula (Ia) exist as a mixture of a Purine Derivative of Formula (Ia') and a Purine Derivative of Formula (Ia") wherein the amount of the Purine Derivative of Formula (Ia") exceeds the amount of the Purine Derivative of Formula (Ia').

In another embodiment, the Purine Derivatives of Formula (Ia) exist as a racemic mixture of a Purine Derivative of Formula (Ia') and a Purine Derivative of Formula (Ia").

In another embodiment, the Purine Derivatives of Formula (Ia) can exist in the form of a single enantiomer, for example, that depicted by either formula (Iaa') or (Iaa"):

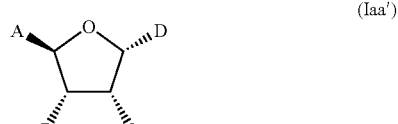

(Iaa')

(Iaa″)

$$\underset{B}{\overset{A}{\diagdown}}\underset{C}{\overset{O}{\diagdown}}D$$

wherein A, B, C and D are defined above for the Purine Derivatives of Formula (Ia).

A Purine Derivative of Formula (Iaa') is the corresponding opposite enantiomer of a Purine Derivative of Formula (Iaa″) when group A of the Purine Derivative of Formula (Iaa') is the same as group A of the Purine Derivative of Formula (Iaa″) and when group D of the Purine Derivative of Formula (Iaa') is the same as group D of the Purine Derivative of Formula (Iaa″).

A Purine Derivative of Formula (Iaa″) is the corresponding opposite enantiomer of a Purine Derivative of Formula (Iaa') when group A of the Purine Derivative of Formula (Iaa″) is the same as group A of the Purine Derivative of Formula (Iaa') and when group D of the Purine Derivative of Formula (Iaa″) is the same as group D of the Purine Derivative of Formula (Iaa').

In one embodiment, the Purine Derivatives of Formula (Ia) have the formula (Iaa'), depicted above, wherein A, B, C and D are defined above for the Purine Derivatives of Formula (Ia), and wherein the Purine Derivatives of Formula (Iaa') are substantially free of their corresponding opposite enantiomer.

In another embodiment, the Purine Derivatives of Formula (Ia) have the formula (Iaa″), depicted above, wherein A, B, C and D are defined above for the Purine Derivatives of Formula (Ia), and wherein the Purine Derivatives of Formula (Iaa″) are substantially free of their corresponding opposite enantiomer.

In another embodiment, the Purine Derivatives of Formula (Ia) exist as a mixture of a Purine Derivative of Formula (Iaa') and a Purine Derivative of Formula (Iaa″) wherein the amount of the Purine Derivative of Formula (Iaa') exceeds the amount of the Purine Derivative of Formula (Iaa″).

In a further embodiment, the Purine Derivatives of Formula (Ia) exist as a mixture of a Purine Derivative of Formula (Iaa') and a Purine Derivative of Formula (Iaa″) wherein the amount of the Purine Derivative of Formula (Iaa″) exceeds the amount of the Purine Derivative of Formula (Iaa').

In another embodiment, the Purine Derivatives of Formula (Ia) exist as a racemic mixture of a Purine Derivative of Formula (Iaa') and a Purine Derivative of Formula (Iaa″).

A Purine Derivative of Formula (Iaa') is the corresponding other anomer of a Purine Derivative of Formula (Ia') when group A of the Purine Derivative of Formula (Iaa') is the same as group A of the Purine Derivative of Formula (Ia') and when group D of the Purine Derivative of Formula (Iaa') is the same as group D of the Purine Derivative of Formula (Ia').

A Purine Derivative of Formula (Ia') is the corresponding other anomer of a Purine Derivative of Formula (Iaa') when group A of the Purine Derivative of Formula (Ia') is the same as group A of the Purine Derivative of Formula (Iaa') and when group D of the Purine Derivative of Formula (Ia') is the same as group D of the Purine Derivative of Formula (Iaa').

A Purine Derivative of Formula (Iaa') is the corresponding other anomer of a Purine Derivative of Formula (Ia″) when group A of the Purine Derivative of Formula (Iaa″) is the same as group A of the Purine Derivative of Formula (Ia″) and when group D of the Purine Derivative of Formula (Iaa″) is the same as group D of the Purine Derivative of Formula (Ia″).

A Purine Derivative of Formula (Ia″) is the corresponding other anomer of a Purine Derivative of Formula (Iaa″) when group A of the Purine Derivative of Formula (Ia″) is the same as group A of the Purine Derivative of Formula (Iaa″) and when group D of the Purine Derivative of Formula (Ia″) is the same as group D of the Purine Derivative of Formula (Iaa″).

In one embodiment, the Purine Derivatives of Formula (Ia) have the formula (Iaa'), depicted above, wherein A, B, C and D are defined above for the Purine Derivatives of Formula (Ia), and wherein the Purine Derivatives of Formula (Iaa') are substantially free of their corresponding other anomer.

In another embodiment, the Purine Derivatives of Formula (Ia) have the formula (Iaa″), depicted above, wherein A, B, C and D are defined above for the Purine Derivatives of Formula (Ia), and wherein the Purine Derivatives of Formula (Iaa″) are substantially free of their corresponding other anomer.

In one embodiment, the Purine Derivatives of Formula (Ia) have the formula (Ia'), depicted above, wherein A, B, C and D are defined above for the Purine Derivatives of Formula (Ia), and wherein the Purine Derivatives of Formula (Ia') are substantially free of their corresponding other anomer.

In another embodiment, the Purine Derivatives of Formula (Ia) have the formula (Ia″), depicted above, wherein A, B, C and D are defined above for the Purine Derivatives of Formula (Ia), and wherein the Purine Derivatives of Formula (Ia″) are substantially free of their corresponding other anomer.

In one embodiment, the Purine Derivatives of Formula (Ia) exist as a mixture of a Purine Derivative of Formula (Ia') and a Purine Derivative of Formula (Iaa') wherein the amount of the Purine Derivative of Formula (Ia') exceeds the amount of the Purine Derivative of Formula (Iaa').

In another embodiment, the Purine Derivatives of Formula (Ia) exist as a mixture of a Purine Derivative of Formula (Ia') and a Purine Derivative of Formula (Iaa') wherein the amount of the Purine Derivative of Formula (Iaa') exceeds the amount of the Purine Derivative of Formula (Ia').

In a further embodiment, the Purine Derivatives of Formula (Ia) exist as a equal mixture of a Purine Derivative of Formula (Ia') and a Purine Derivative of Formula (Iaa').

In one embodiment, the Purine Derivatives of Formula (Ia) exist as a mixture of a Purine Derivative of Formula (Ia″) and a Purine Derivative of Formula (Iaa″) wherein the amount of the Purine Derivative of Formula (Ia″) exceeds the amount of the Purine Derivative of Formula (Iaa″).

In another embodiment, the Purine Derivatives of Formula (Ia) exist as a mixture of a Purine Derivative of Formula (Ia″) and a Purine Derivative of Formula (Iaa″) wherein the amount of the Purine Derivative of Formula (Iaa″) exceeds the amount of the Purine Derivative of Formula (Ia″).

In a further embodiment, the Purine Derivatives of Formula (Ia) exist as a equal mixture of a Purine Derivative of Formula (Ia″) and a Purine Derivative of Formula (Iaa″).

5.2.2 The Purine Derivatives of Formula (Ib)

As stated above, the present invention encompasses Purine Derivatives having the Formula (Ib):

$$\underset{B}{\overset{A}{\diagdown}}\underset{C}{\overset{O}{\diagdown}}D$$

(Ib)

wherein A, B, C and D are defined above for the Purine Derivatives of Formula (Ib), and A and B are trans with respect to each other; B and C are cis with respect to each other; and C and D are cis or trans with respect to each other.

In one embodiment, $R^1$ is —H.

In another embodiment, $R^1$ is —$C_3$-$C_8$ monocyclic cycloalkyl.

In a specific embodiment, $R^1$ is cyclopentyl.

In another embodiment, $R^1$ is —$C_3$-$C_8$ monocyclic cycloalkenyl.

In another embodiment, $R^1$ is —$C_8$-$C_{12}$ bicyclic cycloalkyl or —$C_8$-$C_{12}$ bicyclic cycloalkenyl.

In still another embodiment, $R^1$ is —$(CH_2)_n$—($C_3$-$C_8$ monocyclic cycloalkyl) or —$(CH_2)_n$—($C_3$-$C_8$ monocyclic cycloalkenyl).

In another embodiment, $R^2$ is —CN.

In another embodiment, $R^2$ is —$NHR^4$.

In a further embodiment, $R^2$ is —$NHC(O)R^4$, —$NHC(O)OR^4$ or —$NHC(O)NHR^4$.

In another embodiment, $R^2$ is —$NHNHC(O)R^4$, —$NHNHC(O)OR^4$ or —$NHNHC(O)NHR^4$.

In yet another embodiment, $R^2$ is —NH—N=$C(R^6)R^7$.

In one embodiment, C and D are cis with respect to each other.

In another embodiment, C and D are trans with respect to each other.

The present invention also provides compositions comprising an effective amount of a Purine Derivative of Formula (Ib) and a physiologically acceptable carrier or vehicle.

The invention further provides Purine Derivatives of Formula (Ib) that are in isolated and purified form.

The invention still further provides methods for treating or preventing a Condition, comprising administering an effective amount of a Purine Derivative of Formula (Ib) to an animal in need thereof.

The invention further provides methods for reducing an animal's rate of metabolism, comprising administering an effective amount of a Purine Derivative of Formula (Ib) to an animal in need thereof.

The invention further provides methods protecting an animal's heart against myocardial damage during cardioplegia, comprising administering an effective amount of a Purine Derivative of Formula (Ib) to an animal in need thereof.

The Purine Derivatives of Formula (Ib) can exist in the form of a single enantiomer, for example, that depicted by either the Formula (Ib') or Formula (Ib"):

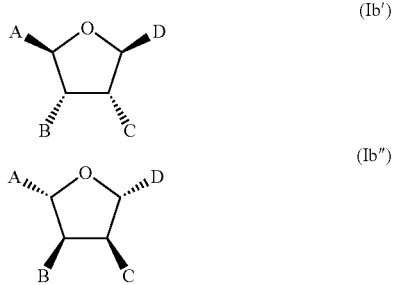

wherein A, B, C and D are defined above for the Purine Derivatives of Formula (Ib).

A Purine Derivative of Formula (Ib') is the corresponding opposite enantiomer of a Purine Derivative of Formula (Ib") when group A of the Purine Derivative of Formula (Ib") is the same as group A of the Purine Derivative of Formula (Ib") and when group D of the Purine Derivative of Formula (Ib') is the same as group D of the Purine Derivative of Formula (Ib").

A Purine Derivative of Formula (Ib") is the corresponding opposite enantiomer of a Purine Derivative of Formula (Ib') when group A of the Purine Derivatives of Formula (Ib") is the same as group A of the Purine Derivative of Formula (Ib') and when group D of the Purine Derivative of Formula (Ib") is the same as group D of the Purine Derivative of Formula (Ib').

In one embodiment, the Purine Derivatives of Formula (Ib) have the formula (Ib'), depicted above, wherein A, B, C and D are defined above for the Purine Derivatives of Formula (Ib), and wherein the Purine Derivatives of Formula (Ib') are substantially free of their corresponding enantiomer, represented by Formula (Ib").

In another embodiment, the Purine Derivatives of Formula (Ib) have the formula (Ib"), depicted above, wherein A, B, C and D are defined above for the Purine Derivatives of Formula (Ib), and wherein the Purine Derivatives of Formula (Ib") are substantially free of their corresponding enantiomer, represented by Formula (Ib').

In one embodiment, the Purine Derivatives of Formula (Ib) exist as a mixture of a Purine Derivative of Formula (Ib') and a Purine Derivative of Formula (Ib") wherein the amount of the Purine Derivative of Formula (Ib') exceeds the amount of the Purine Derivative of Formula (Ib").

In another embodiment, the Purine Derivatives of Formula (Ib) exist as a mixture of a Purine Derivative of Formula (Ib') and a Purine Derivative of Formula (Ib") wherein the amount of the Purine Derivative of Formula (Ib") exceeds the amount of the Purine Derivative of Formula (Ib').

In another embodiment, the Purine Derivatives of Formula (Ib) exist as a racemic mixture of a Purine Derivative of Formula (Ib') and a Purine Derivative of Formula (Ib").

In another embodiment, the Purine Derivatives of Formula (Ib) can exist in the form of a single enantiomer, for example, that depicted by either formula (Ibb') or (Ib"):

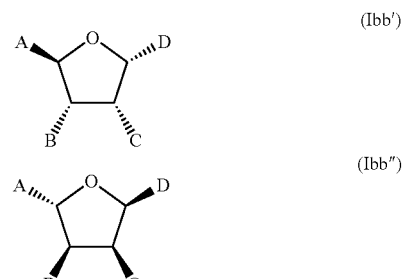

wherein A, B, C and D are defined above for the Purine Derivatives of Formula (Ib).

A Purine Derivative of Formula (Ibb') is the corresponding opposite enantiomer of a Purine Derivative of Formula (Ibb") when group A of the Purine Derivative of Formula (Ibb') is the same as group A of the Purine Derivative of Formula (Ibb") and when group D of the Purine Derivative of Formula (Ibb') is the same as group D of the Purine Derivative of Formula (Ibb").

A Purine Derivative of Formula (Ibb") is the corresponding opposite enantiomer of a Purine Derivative of Formula (Ibb') when group A of the Purine Derivative of Formula (Ibb") is the same as group A of the Purine Derivative of Formula (Ibb') and when group D of the Purine Derivative of Formula (Ibb") is the same as group D of the Purine Derivative of Formula (Ibb').

In one embodiment, the Purine Derivatives of Formula (Ib) have the formula (Ibb'), depicted above, wherein A, B, C and D are defined above for the Purine Derivatives of Formula (Ib), and wherein the Purine Derivatives of Formula (Ibb') are substantially free of their corresponding opposite enantiomer.

In another embodiment, the Purine Derivatives of Formula (Ib) have the formula (Ibb"), depicted above, wherein A, B, C and D are defined above for the Purine Derivatives of Formula (Ib), and wherein the Purine Derivatives of Formula (Ibb") are substantially free of their corresponding-opposite enantiomer.

In another embodiment, the Purine Derivatives of Formula (Ib) exist as a mixture of a Purine Derivative of Formula (Ibb') and a Purine Derivative of Formula (Ibb") wherein the amount of the Purine Derivative of Formula (Ibb') exceeds the amount of the Purine Derivative of Formula (Ibb").

In a further embodiment, the Purine Derivatives of Formula (Ib) exist as a mixture of a Purine Derivative of Formula (Ibb') and a Purine Derivative of Formula (Ibb") wherein the amount of the Purine Derivative of Formula (Ibb") exceeds the amount of the Purine Derivative of Formula (Ibb').

In another embodiment, the Purine Derivatives of Formula (Ib) exist as a racemic mixture of a Purine Derivative of Formula (Ibb') and a Purine Derivative of Formula (Ibb").

A Purine Derivative of Formula (Ibb') is the corresponding other anomer of a Purine Derivative of Formula (Ib') when group A of the Purine Derivative of Formula (Ibb') is the same as group A of the Purine Derivative of Formula (Ib') and when group D of the Purine Derivative of Formula (Ibb') is the same as group D of the Purine Derivative of Formula (Ib').

A Purine Derivative of Formula (Ib') is the corresponding other anomer of a Purine Derivative of Formula (Ibb') when group A of the Purine Derivative of Formula (Ib') is the same as group A of the Purine Derivative of Formula (Ibb') and when group D of the Purine Derivative of Formula (Ib') is the same as group D of the Purine Derivative of Formula (Ibb').

A Purine Derivative of Formula (Ibb") is the corresponding other anomer of a Purine Derivative of Formula (Ib") when group A of the Purine Derivative of Formula (Ibb") is the same as group A of the Purine Derivative of Formula (Ib") and when group D of the Purine Derivative of Formula (Ibb") is the same as group D of the Purine Derivative of Formula (Ib").

A Purine Derivative of Formula (Ib") is the corresponding other anomer of a Purine Derivative of Formula (Ibb") when group A of the Purine Derivative of Formula (Ib") is the same as group A of the Purine Derivative of Formula (Ibb") and when group D of the Purine Derivative of Formula (Ib") is the same as group D of the Purine Derivative of Formula (Ibb").

In one embodiment, the Purine Derivatives of Formula (Ib) have the formula (Ibb'), depicted above, wherein A, B, C and D are defined above for the Purine Derivatives of Formula (Ib), and wherein the Purine Derivatives of Formula (Ibb') are substantially free of their corresponding other anomer.

In another embodiment, the Purine Derivatives of Formula (Ib) have the formula (Ibb"), depicted above, wherein A, B, C and D are defined above for the Purine Derivatives of Formula (Ib), and wherein the Purine Derivatives of Formula (Ibb") are substantially free of their corresponding other anomer.

In one embodiment, the Purine Derivatives of Formula (Ib) have the formula (Ib'), depicted above, wherein A, B, C and D are defined above for the Purine Derivatives of Formula (Ib), and wherein the Purine Derivatives of Formula (Ib') are substantially free of their corresponding other anomer.

In another embodiment, the Purine Derivatives of Formula (Ib) have the formula (Ib"), depicted above, wherein A, B, C and D are defined above for the Purine Derivatives of Formula (Ib), and wherein the Purine Derivatives of Formula (Ib") are substantially free of their corresponding other anomer.

In one embodiment, the Purine Derivatives of Formula (Ib) exist as a mixture of a Purine Derivative of Formula (Ib') and a Purine Derivative of Formula (Ibb') wherein the amount of the Purine Derivative of Formula (Ib') exceeds the amount of the Purine Derivative of Formula (Ibb').

In another embodiment, the Purine Derivatives of Formula (Ib) exist as a mixture of a Purine Derivative of Formula (Ib') and a Purine Derivative of Formula (Ibb') wherein the amount of the Purine Derivative of Formula (Ibb') exceeds the amount of the Purine Derivative of Formula (Ib').

In another embodiment, the Purine Derivatives of Formula (Ib) exist as a equal mixture of a Purine Derivative of Formula (Ib') and a Purine Derivative of Formula (Ibb').

In one embodiment, the Purine Derivatives of Formula (Ib) exist as a mixture of a Purine Derivative of Formula (Ib") and a Purine Derivative of Formula (Ibb") wherein the amount of the Purine Derivative of Formula (Ib") exceeds the amount of the Purine Derivative of Formula (Ibb").

In another embodiment, the Purine Derivatives of Formula (Ib) exist as a mixture of a Purine Derivative of Formula (Ib") and a Purine Derivative of Formula (Ibb") wherein the amount of the Purine Derivative of Formula (Ibb") exceeds the amount of the Purine Derivative of Formula (Ib").

In another embodiment, the Purine Derivatives of Formula (Ib) exist as a equal mixture of a Purine Derivative of Formula (Ib") and a Purine Derivative of Formula (Ibb").

Illustrative Purine Derivatives of Formula (Ib) include the compound listed below:

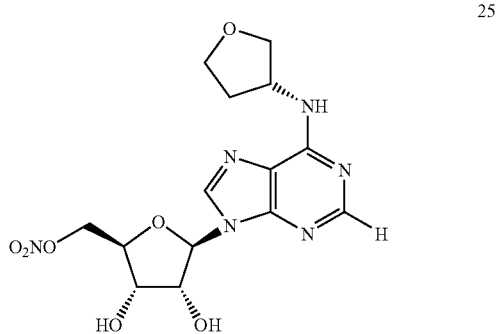

25

5.2.3 The Purine Derivatives of Formula (Ic)

As stated above, the present invention encompasses Purine Derivatives having the Formula (Ic):

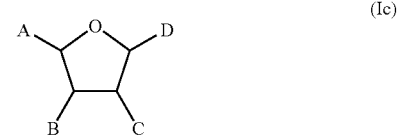

(Ic)

wherein A, B, C and D are defined above for the Purine Derivatives of Formula (Ic), and A and B are trans with respect to each other; B and C are cis with respect to each other; and C and D are cis or trans with respect to each other.

In one embodiment, $R^1$ is —H.

In another embodiment, $R^1$ is —$C_1$-$C_{10}$ alkyl.

In one embodiment, $R^1$ is -aryl or —$(CH_2)_n$-aryl.

In another embodiment, $R^1$ is —$C_3$-$C_8$ monocyclic cycloalkyl.

In a specific embodiment, $R^1$ is cyclopentyl.

In another embodiment, $R^1$ is $-C_3$-$C_8$ monocyclic cycloalkenyl.

In another embodiment, $R^1$ is $-C_8$-$C_{12}$ bicyclic cycloalkyl or $-C_8$-$C_{12}$ bicyclic cycloalkenyl.

In still another embodiment, $R^1$ is $-(CH_2)_n-(C_3$-$C_8$ monocyclic cycloalkyl) or $-(CH_2)_n-(C_3$-$C_8$ monocyclic cycloalkenyl).

In another embodiment, $R^1$ is -3- to 7-membered monocyclic heterocycle or -8- to 12-membered bicyclic heterocycle.

In another embodiment, $R^2$ is $-NHR^4$, $-OR^4$ or $-SR^4$.

In a further embodiment, $R^2$ is $-NHC(O)R^4$, $-NHC(O)OR^4$ or $-NHC(O)NHR^4$.

In another embodiment, $R^2$ is $-NHNHC(O)R^4$, $-NHNHC(O)OR^4$ or $-NHNHC(O)NHR^4$. In one embodiment, $R^5$ is $-C(O)O(C_1$-$C_{10}$ alkyl).

In another embodiment, $R^5$ is $-C(O)NH(C_1$-$C_{10}$ alkyl), $-C(O)N(C_1$-$C_{10}$ alkyl)$_2$ or $-C(O)NH$-aryl.

In another embodiment, $R^5$ is $-CH(NH_2)NH_2$ or $-CH(NH_2)NH(C_1$-$C_{10}$ alkyl).

In one embodiment, C and D are cis with respect to each other.

In another embodiment, C and D are trans with respect to each other.

The present invention also provides compositions comprising an effective amount of a Purine Derivative of Formula (Ic) and a physiologically acceptable carrier or vehicle.

The invention further provides Purine Derivatives of Formula (Ic) that are in isolated and purified form.

The invention still further provides methods for treating or preventing a Condition, comprising administering an effective amount of a Purine Derivative of Formula (Ic) to an animal in need thereof.

The invention further provides methods for reducing an animal's rate of metabolism, comprising administering an effective amount of a Purine Derivative of Formula (Ic) to an animal in need thereof.

The invention further provides methods protecting an animal's heart against myocardial damage during cardioplegia, comprising administering an effective amount of a Purine Derivative of Formula (Ic) to an animal in need thereof.

The Purine Derivatives of Formula (Ic) can exist in the form of a single enantiomer, for example, that depicted by either the Formula (Ic') or Formula (Ic"):

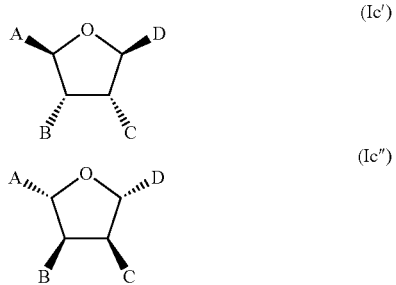

wherein A, B, C and D are defined above for the Purine Derivatives of Formula (Ic).

A Purine Derivative of Formula (Ic') is the corresponding opposite enantiomer of a Purine Derivative of Formula (Ic") when group A of the Purine Derivative of Formula (Ic') is the same as group A of the Purine Derivative of Formula (Ic") and when group D of the Purine Derivative of Formula (Ic') is the same as group D of the Purine Derivative of Formula (Ic").

A Purine Derivative of Formula (Ic") is the corresponding opposite enantiomer of a Purine Derivative of Formula (Ic') when group A of the Purine Derivatives of Formula (Ic") is the same as group A of the Purine Derivative of Formula (Ic') and when group D of the Purine Derivative of Formula (Ic") is the same as group D of the Purine Derivative of Formula (Ic').

In one embodiment, the Purine Derivatives of Formula (Ic) have the formula (Ic'), depicted above, wherein A, B, C and D are defined above for the Purine Derivatives of Formula (Ic), and wherein the Purine Derivatives of Formula (Ic') are substantially free of their corresponding enantiomer, represented by Formula (Ic").

In another embodiment, the Purine Derivatives of Formula (Ic) have the formula (Ic"), depicted above, wherein A, B, C and D are defined above for the Purine Derivatives of Formula (Ic), and wherein the Purine Derivatives of Formula (Ic") are substantially free of their corresponding enantiomer, represented by Formula (Ic').

In one embodiment, the Purine Derivatives of Formula (Ic) exist as a mixture of a Purine Derivative of Formula (Ic') and a Purine Derivative of Formula (Ic") wherein the amount of the Purine Derivative of Formula (Ic') exceeds the amount of the Purine Derivative of Formula (Ic").

In another embodiment, the Purine Derivatives of Formula (Ic) exist as a mixture of a Purine Derivative of Formula (Ic') and a Purine Derivative of Formula (Ic") wherein the amount of the Purine Derivative of Formula (Ic") exceeds the amount of the Purine Derivative of Formula (Ic').

In another embodiment, the Purine Derivatives of Formula (Ic) exist as a racemic mixture of a Purine Derivative of Formula (Ic') and a Purine Derivative of Formula (Ic").

In another embodiment, the Purine Derivatives of Formula (Ic) can exist in the form of a single enantiomer, for example, that depicted by either formula (Icc') or (Icc"):

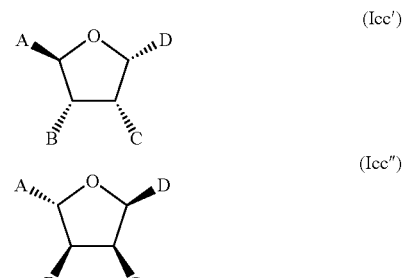

wherein A, B, C and D are defined above for the Purine Derivatives of Formula (Ic).

A Purine Derivative of Formula (Icc') is the corresponding opposite enantiomer of a Purine Derivative of Formula (Icc") when group A of the Purine Derivative of Formula (Icc') is the same as group A of the Purine Derivative of Formula (Icc") and when group D of the Purine Derivative of Formula (Icc') is the same as group D of the Purine Derivative of Formula (Icc").

A Purine Derivative of Formula (Icc") is the corresponding opposite enantiomer of a Purine Derivative of Formula (Icc') when group A of the Purine Derivative of Formula (Icc") is the same as group A of the Purine Derivative of Formula (Icc') and when group D of the Purine Derivative of Formula (Icc") is the same as group D of the Purine Derivative of Formula (Icc').

In one embodiment, the Purine Derivatives of Formula (Ic) have the formula (Icc'), depicted above, wherein A, B, C and D are defined above for the Purine Derivatives of Formula (Ic), and wherein the Purine Derivatives of Formula (Icc') are substantially free of their corresponding opposite enantiomer.

In another embodiment, the Purine Derivatives of Formula (Ic) have the formula (Icc"), depicted above, wherein A, B, C and D are defined above for the Purine Derivatives of Formula (Ic), and wherein the Purine Derivatives of Formula (Icc") are substantially free of their corresponding opposite enantiomer.

In another embodiment, the Purine Derivatives of Formula (Ic) exist as a mixture of a Purine Derivative of Formula (Icc') and a Purine Derivative of Formula (Icc") wherein the amount of the Purine Derivative of Formula (Icc') exceeds the amount of the Purine Derivative of Formula (Icc").

In a further embodiment, the Purine Derivatives of Formula (Ic) exist as a mixture of a Purine Derivative of Formula (Icc') and a Purine Derivative of Formula (Icc") wherein the amount of the Purine Derivative of Formula (Icc") exceeds the amount of the Purine Derivative of Formula (Icc').

In another embodiment, the Purine Derivatives of Formula (Ic) exist as a racemic mixture of a Purine Derivative of Formula (Icc') and a Purine Derivative of Formula (Icc").

A Purine Derivative of Formula (Icc') is the corresponding other anomer of a Purine Derivative of Formula (Ic') when group A of the Purine Derivative of Formula (Icc') is the same as group A of the Purine Derivative of Formula (Ic') and when group D of the Purine Derivative of Formula (Icc') is the same as group D of the Purine Derivative of Formula (Ic').

A Purine Derivative of Formula (Ic') is the corresponding other anomer of a Purine Derivative of Formula (Icc') when group A of the Purine Derivative of Formula (Ic') is the same as group A of the Purine Derivative of Formula (Icc') and when group D of the Purine Derivative of Formula (Ic') is the same as group D of the Purine Derivative of Formula (Icc').

A Purine Derivative of Formula (Icc") is the corresponding other anomer of a Purine Derivative of Formula (Ic") when group A of the Purine Derivative of Formula (Icc") is the same as group A of the Purine Derivative of Formula (Ic") and when group D of the Purine Derivative of Formula (Icc") is the same as group D of the Purine Derivative of Formula (Ic").

A Purine Derivative of Formula (Ic") is the corresponding other anomer of a Purine Derivative of Formula (Icc") when group A of the Purine Derivative of Formula (Ic") is the same as group A of the Purine Derivative of Formula (Icc") and when group D of the Purine Derivative of Formula (Ic") is the same as group D of the Purine Derivative of Formula (Icc").

In one embodiment, the Purine Derivatives of Formula (Ic) have the formula (Icc'), depicted above, wherein A, B, C and D are defined above for the Purine Derivatives of Formula (Ic), and wherein the Purine Derivatives of Formula (Icc') are substantially free of their corresponding other anomer.

In another embodiment, the Purine Derivatives of Formula (Ic) have the formula (Icc"), depicted above, wherein A, B, C and D are defined above for the Purine Derivatives of Formula (Ic), and wherein the Purine Derivatives of Formula (Icc") are substantially free of their corresponding other anomer.

In one embodiment, the Purine Derivatives of Formula (Ic) have the formula (Ic'), depicted above, wherein A, B, C and D are defined above for the Purine Derivatives of Formula (Ic), and wherein the Purine Derivatives of Formula (Ic') are substantially free of their corresponding other anomer.

In another embodiment, the Purine Derivatives of Formula (Ic) have the formula (Ic"), depicted above, wherein A, B, C and D are defined above for the Purine Derivatives of Formula (Ic), and wherein the Purine Derivatives of Formula (Ic") are substantially free of their corresponding other anomer.

In one embodiment, the Purine Derivatives of Formula (Ic) exist as a mixture of a Purine Derivative of Formula (Ic') and a Purine Derivative of Formula (Icc') wherein the amount of the Purine Derivative of Formula (Ic') exceeds the amount of the Purine Derivative of Formula (Icc').

In another embodiment, the Purine Derivatives of Formula (Ic) exist as a mixture of a Purine Derivative of Formula (Ic') and a Purine Derivative of Formula (Icc') wherein the amount of the Purine Derivative of Formula (Icc') exceeds the amount of the Purine Derivative of Formula (Ic').

In another embodiment, the Purine Derivatives of Formula (Ic) exist as a equal mixture of a Purine Derivative of Formula (Ic') and a Purine Derivative of Formula (Icc').

In one embodiment, the Purine Derivatives of Formula (Ic) exist as a mixture of a Purine Derivative of Formula (Ic") and a Purine Derivative of Formula (Icc") wherein the amount of the Purine Derivative of Formula (Ic") exceeds the amount of the Purine Derivative of Formula (Icc").

In another embodiment, the Purine Derivatives of Formula (Ic) exist as a mixture of a Purine Derivative of Formula (Ic") and a Purine Derivative of Formula (Icc") wherein the amount of the Purine Derivative of Formula (Icc") exceeds the amount of the Purine Derivative of Formula (Ic").

In another embodiment, the Purine Derivatives of Formula (Ic) exist as a equal mixture of a Purine Derivative of Formula (Ic") and a Purine Derivative of Formula (Icc").

5.2.4 The Purine Derivatives of Formula (Id)

As stated above, the present invention encompasses Purine Derivatives having the Formula (Id):

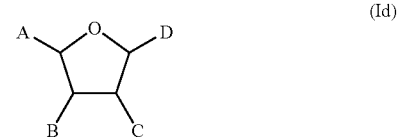

(Id)

wherein A, B, C and D are defined above for the Purine Derivatives of Formula (Id), and A and B are trans with respect to each other; B and C are cis with respect to each other; and C and D are cis or trans with respect to each other.

In one embodiment, $R^1$ is —H.

In another embodiment, $R^1$ is —$C_1$-$C_{10}$ alkyl.

In one embodiment, $R^1$ is -aryl or —$(CH_2)_n$-aryl.

In another embodiment, $R^1$ is —$C_3$-$C_8$ monocyclic cycloalkyl.

In a specific embodiment, $R^1$ is cyclopentyl.

In another embodiment, $R^1$ is —$C_3$-$C_8$ monocyclic cycloalkenyl.

In another embodiment, $R^1$ is —$C_8$-$C_{12}$ bicyclic cycloalkyl or —$C_8$-$C_{12}$ bicyclic cycloalkenyl.

In still another embodiment, $R^1$ is —$(CH_2)_n$—($C_3$-$C_8$ monocyclic cycloalkyl) or —$(CH_2)_n$—($C_3$-$C_8$ monocyclic cycloalkenyl).

In another embodiment, $R^1$ is -3- to 7-membered monocyclic heterocycle or -8- to 12-membered bicyclic heterocycle.

In one embodiment, $R^2$ is —H.

In one embodiment, $R^2$ is -halo.

In a specific embodiment, $R^2$ is —Cl.

In another embodiment, $R^2$ is —N.

In another embodiment, $R^2$ is —$NHR^4$, —$OR^4$ or —$SR^4$.

In a further embodiment, $R^2$ is —$NHC(O)R^4$, —$NHC(O)OR^4$ or —$NHC(O)NHR^4$.

In another embodiment, $R^2$ is —$NHNHC(O)R^4$, —$NHNHC(O)OR^4$ or —$NHNHC(O)NHR^4$.

In yet another embodiment, $R^2$ is —NH—N=C($R^6$)$R^7$.

In one embodiment, $R^3$ is —CH$_2$ONO.

In another embodiment, $R^3$ is —CH$_2$OSO$_3$H.

In one embodiment, C and D are cis with respect to each other.

In another embodiment, C and D are trans with respect to each other.

The present invention also provides compositions comprising an effective amount of a Purine Derivative of Formula (Id) and a physiologically acceptable carrier or vehicle.

The invention further provides Purine Derivatives of Formula (Id) that are in isolated and purified form.

The invention still further provides methods for treating or preventing a Condition, comprising administering an effective amount of a Purine Derivative of Formula (Id) to an animal in need thereof.

The invention further provides methods for reducing an animal's rate of metabolism, comprising administering an effective amount of a Purine Derivative of Formula (Id) to an animal in need thereof.

The invention further provides methods protecting an animal's heart against myocardial damage during cardioplegia, comprising administering an effective amount of a Purine Derivative of Formula (Id) to an animal in need thereof.

The Purine Derivatives of Formula (Id) can exist in the form of a single enantiomer, for example, that depicted by either the Formula (Id') or Formula (Id"):

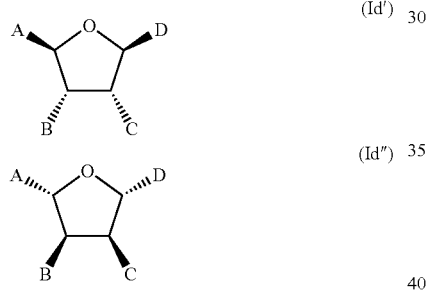

wherein A, B, C and D are defined above for the Purine Derivatives of Formula (Id).

A Purine Derivative of Formula (Id') is the corresponding opposite enantiomer of a Purine Derivative of Formula (Id") when group A of the Purine Derivative of Formula (Id') is the same as group A of the Purine Derivative of Formula (Id") and when group D of the Purine Derivative of Formula (Id') is the same as group D of the Purine Derivative of Formula (Id").

A Purine Derivative of Formula (Id") is the corresponding opposite enantiomer of a Purine Derivative of Formula (Id') when group A of the Purine Derivatives of Formula (Id") is the same as group A of the Purine Derivative of Formula (Id') and when group D of the Purine Derivative of Formula (Id") is the same as group D of the Purine Derivative of Formula (Id').

In one embodiment, the Purine Derivatives of Formula (Id) have the formula (Id'), depicted above, wherein A, B, C and D are defined above for the Purine Derivatives of Formula (Id), and wherein the Purine Derivatives of Formula (Id') are substantially free of their corresponding enantiomer, represented by Formula (Id").

In another embodiment, the Purine Derivatives of Formula (Id) have the formula (Id"), depicted above, wherein A, B, C and D are defined above for the Purine Derivatives of Formula (Id), and wherein the Purine Derivatives of Formula (Id") are substantially free of their corresponding enantiomer, represented by Formula (Id').

In one embodiment, the Purine Derivatives of Formula (Id) exist as a mixture of a Purine Derivative of Formula (Id') and a Purine Derivative of Formula (Id") wherein the amount of the Purine Derivative of Formula (Id') exceeds the amount of the Purine Derivative of Formula (Id").

In another embodiment, the Purine Derivatives of Formula (Id) exist as a mixture of a Purine Derivative of Formula (Id') and a Purine Derivative of Formula (Id") wherein the amount of the Purine Derivative of Formula (Id") exceeds the amount of the Purine Derivative of Formula (Id').

In another embodiment, the Purine Derivatives of Formula (Id) exist as a racemic mixture of a Purine Derivative of Formula (Id') and a Purine Derivative of Formula (Id").

In another embodiment, the Purine Derivatives of Formula (Id) can exist in the form of a single enantiomer, for example, that depicted by either formula (Idd') or (Idd"):

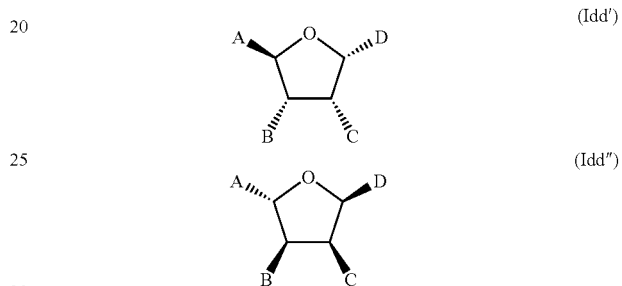

wherein A, B, C and D are defined above for the Purine Derivatives of Formula (Id).

A Purine Derivative of Formula (Idd') is the corresponding opposite enantiomer of a Purine Derivative of Formula (Idd") when group A of the Purine Derivative of Formula (Idd') is the same as group A of the Purine Derivative of Formula (Idd") and when group D of the Purine Derivative of Formula (Idd') is the same as group D of the Purine Derivative of Formula (Idd").

A Purine Derivative of Formula (Idd") is the corresponding opposite enantiomer of a Purine Derivative of Formula (Idd') when group A of the Purine Derivative of Formula (Idd") is the same as group A of the Purine Derivative of Formula (Idd') and when group D of the Purine Derivative of Formula (Idd") is the same as group D of the Purine Derivative of Formula (Idd').

In one embodiment, the Purine Derivatives of Formula (Id) have the formula (Idd'), depicted above, wherein A, B, C and D are defined above for the Purine Derivatives of Formula (Id), and wherein the Purine Derivatives of Formula (Idd') are substantially free of their corresponding opposite enantiomer.

In another embodiment, the Purine Derivatives of Formula (Id) have the formula (Idd"), depicted above, wherein A, B, C and D are defined above for the Purine Derivatives of Formula (Id), and wherein the Purine Derivatives of Formula (Idd") are substantially free of their corresponding opposite enantiomer.

In another embodiment, the Purine Derivatives of Formula (Id) exist as a mixture of a Purine Derivative of Formula (Idd') and a Purine Derivative of Formula (Idd") wherein the amount of the Purine Derivative of Formula (Idd') exceeds the amount of the Purine Derivative of Formula (Idd").

In a further embodiment, the Purine Derivatives of Formula (Id) exist as a mixture of a Purine Derivative of Formula (Idd') and a Purine Derivative of Formula (Idd") wherein the amount of the Purine Derivative of Formula (Idd") exceeds the amount of the Purine Derivative of Formula (Idd').

In another embodiment, the Purine Derivatives of Formula (Id) exist as a racemic mixture of a Purine Derivative of Formula (Idd') and a Purine Derivative of Formula (Idd").

A Purine Derivative of Formula (Idd') is the corresponding other anomer of a Purine Derivative of Formula (Id') when group A of the Purine Derivative of Formula (Idd') is the same as group A of the Purine Derivative of Formula (Ib') and when group D of the Purine Derivative of Formula (Idd') is the same as group D of the Purine Derivative of Formula (Id').

A Purine Derivative of Formula (Id') is the corresponding other anomer of a Purine Derivative of Formula (Idd') when group A of the Purine Derivative of Formula (Id') is the same as group A of the Purine Derivative of Formula (Idd') and when group D of the Purine Derivative of Formula (Id') is the same as group D of the Purine Derivative of Formula (Idd').

A Purine Derivative of Formula (Idd") is the corresponding other anomer of a Purine Derivative of Formula (Id") when group A of the Purine Derivative of Formula (Idd") is the same as group A of the Purine Derivative of Formula (Id") and when group D of the Purine Derivative of Formula (Idd") is the same as group D of the Purine Derivative of Formula (Id").

A Purine Derivative of Formula (Id") is the corresponding other anomer of a Purine Derivative of Formula (Idd") when group A of the Purine Derivative of Formula (Id") is the same as group A of the Purine Derivative of Formula (Idd") and when group D of the Purine Derivative of Formula (Id") is the same as group D of the Purine Derivative of Formula (Idd").

In one embodiment, the Purine Derivatives of Formula (Id) have the formula (Idd'), depicted above, wherein A, B, C and D are defined above for the Purine Derivatives of Formula (Id), and wherein the Purine Derivatives of Formula (Idd') are substantially free of their corresponding other anomer.

In another embodiment, the Purine Derivatives of Formula (Id) have the formula (Idd"), depicted above, wherein A, B, C and D are defined above for the Purine Derivatives of Formula (Id), and wherein the Purine Derivatives of Formula (Idd") are substantially free of their corresponding other anomer.

In one embodiment, the Purine Derivatives of Formula (Id) have the formula (Id'), depicted above, wherein A, B, C and D are defined above for the Purine Derivatives of Formula (Id), and wherein the Purine Derivatives of Formula (Id') are substantially free of their corresponding other anomer.

In another embodiment, the Purine Derivatives of Formula (Id) have the formula (Id"), depicted above, wherein A, B, C and D are defined above for the Purine Derivatives of Formula (Id), and wherein the Purine Derivatives of Formula (Id") are substantially free of their corresponding other anomer.

In one embodiment, the Purine Derivatives of Formula (Id) exist as a mixture of a Purine Derivative of Formula (Id') and a Purine Derivative of Formula (Idd') wherein the amount of the Purine Derivative of Formula (Id') exceeds the amount of the Purine Derivative of Formula (Idd').

In another embodiment, the Purine Derivatives of Formula (Id) exist as a mixture of a Purine Derivative of Formula (Id') and a Purine Derivative of Formula (Idd') wherein the amount of the Purine Derivative of Formula (Idd') exceeds the amount of the Purine Derivative of Formula (Id').

In another embodiment, the Purine Derivatives of Formula (Id) exist as a equal mixture of a Purine Derivative of Formula (Id') and a Purine Derivative of Formula (Idd').

In one embodiment, the Purine Derivatives of Formula (Id) exist as a mixture of a Purine Derivative of Formula (Id") and a Purine Derivative of Formula (Idd") wherein the amount of the Purine Derivative of Formula (Id") exceeds the amount of the Purine Derivative of Formula (Idd").

In another embodiment, the Purine Derivatives of Formula (Id) exist as a mixture of a Purine Derivative of Formula (Id") and a Purine Derivative of Formula (Idd") wherein the amount of the Purine Derivative of Formula (Idd") exceeds the amount of the Purine Derivative of Formula (Id").

In another embodiment, the Purine Derivatives of Formula (Id) exist as a equal mixture of a Purine Derivative of Formula (Id") and a Purine Derivative of Formula (Idd")

Illustrative Purine Derivatives of Formula (Id) include the compounds listed below:

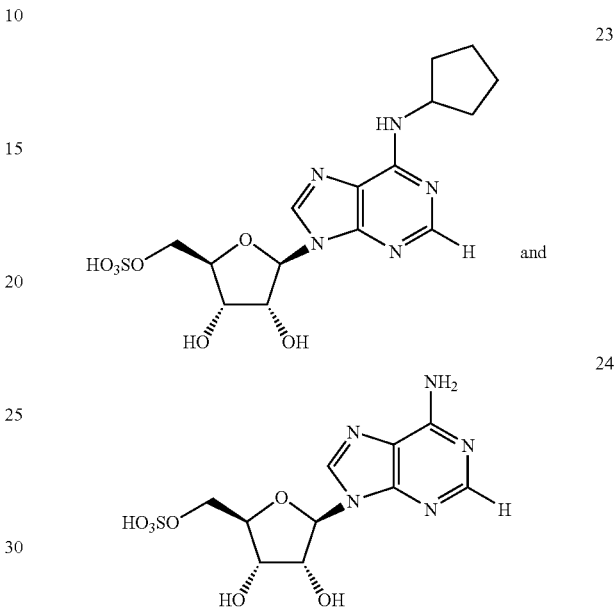

and pharmaceutically acceptable salts thereof.

In one embodiment, compound 23 is in the form of its sodium salt.

In another embodiment, compound 24 is in the form of its sodium salt.

5.2.5 The Purine Derivatives of Formula (Ie)

As stated above, the present invention encompasses Purine Derivatives having the Formula (Ie):

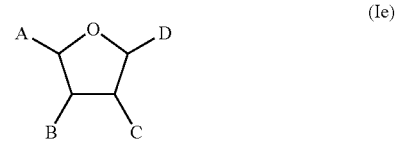

wherein A, B, C and D are defined above for the Purine Derivatives of Formula (Ie), and A and B are trans with respect to each other; B and C are cis with respect to each other; and C and D are cis or trans with respect to each other.

In one embodiment, $R^1$ is —$(CH_2)_n$-aryl.

In another embodiment, $R^1$ is —$C_3$-$C_8$ monocyclic cycloalkyl.

In a specific embodiment, $R^1$ is cyclopentyl.

In another embodiment, $R^1$ is —$C_3$-$C_8$ monocyclic cycloalkenyl.

In another embodiment, $R^1$ is —$C_8$-$C_{12}$ bicyclic cycloalkyl or —$C_8$-$C_{12}$ bicyclic cycloalkenyl.

In still another embodiment, $R^1$ is —$(CH_2)_n$—($C_3$-$C_8$ monocyclic cycloalkyl) or —$(CH_2)_n$—($C_3$-$C_8$ monocyclic cycloalkenyl).

In another embodiment, $R^1$ is -3- to 7-membered monocyclic heterocycle or -8- to 12-membered bicyclic heterocycle.

In one embodiment, $R^2$ is -halo.

In a specific embodiment, $R^2$ is —Cl.

In another embodiment, $R^2$ is —CN.

In another embodiment, $R^2$ is —NHR$^4$, —OR$^4$ or —R$^4$.

In a further embodiment, $R^2$ is —NHC(O)R$^4$, —NHC(O)OR$^4$ or —NHC(O)NHR$^4$.

In another embodiment, $R^2$ is —NHNHC(O)R$^4$, —NHNHC(O)OR$^4$ or —NHNHC(O)NHR$^4$.

In yet another embodiment, $R^2$ is —NH—N=C(R$^6$)R$^7$.

In one embodiment, C and D are cis with respect to each other.

In another embodiment, C and D are trans with respect to each other.

The present invention also provides compositions comprising an effective amount of a Purine Derivative of Formula (Ie) and a physiologically acceptable carrier or vehicle.

The invention further provides Purine Derivatives of Formula (Ie) that are in isolated and purified form.

The invention still further provides methods for treating or preventing a Condition, comprising administering an effective amount of a Purine Derivative of Formula (Ie) to an animal in need thereof.

The invention further provides methods for reducing an animal's rate of metabolism, comprising administering an effective amount of a Purine Derivative of Formula (Ie) to an animal in need thereof.

The invention further provides methods protecting an animal's heart against myocardial damage during cardioplegia, comprising administering an effective amount of a Purine Derivative of Formula (Ie) to an animal in need thereof.

The Purine Derivatives of Formula (Ie) can exist in the form of a single enantiomer, for example, that depicted by either the Formula (Ie') or Formula (Ie"):

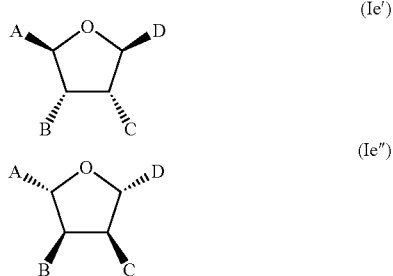

wherein A, B, C and D are defined above for the Purine Derivatives of Formula (Ie).

A Purine Derivative of Formula (Ie') is the corresponding opposite enantiomer of a Purine Derivative of Formula (Ie") when group A of the Purine Derivative of Formula (Ie') is the same as group A of the Purine Derivative of Formula (Ie") and when group D of the Purine Derivative of Formula (Ie') is the same as group D of the Purine Derivative of Formula (Ie").

A Purine Derivative of Formula (Ie") is the corresponding opposite enantiomer of a Purine Derivative of Formula (Ie') when group A of the Purine Derivatives of Formula (Ie") is the same as group A of the Purine Derivative of Formula (Ie') and when group D of the Purine Derivative of Formula (Ie") is the same as group D of the Purine Derivative of Formula (Ie').

In one embodiment, the Purine Derivatives of Formula (Ie) have the formula (Ie'), depicted above, wherein A, B, C and D are defined above for the Purine Derivatives of Formula (Ie), and wherein the Purine Derivatives of Formula (Ie') are substantially free of their corresponding enantiomer, represented by Formula (Ie").

In another embodiment, the Purine Derivatives of Formula (Ie) have the formula (Ie"), depicted above, wherein A, B, C and D are defined above for the Purine Derivatives of Formula (Ie), and wherein the Purine Derivatives of Formula (Ie") are substantially free of their corresponding enantiomer, represented by Formula (Ie').

In one embodiment, the Purine Derivatives of Formula (Ie) exist as a mixture of a Purine Derivative of Formula (Ie') and a Purine Derivative of Formula (Ie") wherein the amount of the Purine Derivative of Formula (Ie') exceeds the amount of the Purine Derivative of Formula (Ie").

In another embodiment, the Purine Derivatives of Formula (Ie) exist as a mixture of a Purine Derivative of Formula (Ie') and a Purine Derivative of Formula (Ie") wherein the amount of the Purine Derivative of Formula (Ie") exceeds the amount of the Purine Derivative of Formula (Ie').

In another embodiment, the Purine Derivatives of Formula (Ie) exist as a racemic mixture of a Purine Derivative of Formula (Ie') and a Purine Derivative of Formula (Ie").

In another embodiment, the Purine Derivatives of Formula (Ie) can exist in the form of a single enantiomer, for example, that depicted by either formula (Iee') or (Iee"):

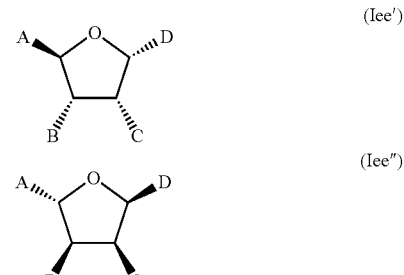

wherein A, B, C and D are defined above for the Purine Derivatives of Formula (Ie).

A Purine Derivative of Formula (Iee') is the corresponding opposite enantiomer of a Purine Derivative of Formula (Iee") when group A of the Purine Derivative of Formula (Iee') is the same as group A of the Purine Derivative of Formula (Iee") and when group D of the Purine Derivative of Formula (Iee') is the same as group D of the Purine Derivative of Formula (Iee").

A Purine Derivative of Formula (Iee") is the corresponding opposite enantiomer of a Purine Derivative of Formula (Iee') when group A of the Purine Derivative of Formula (Iee") is the same as group A of the Purine Derivative of Formula (Iee') and when group D of the Purine Derivative of Formula (Iee") is the same as group D of the Purine Derivative of Formula (Iee').

In one embodiment, the Purine Derivatives of Formula (Ie) have the formula (Iee'), depicted above, wherein A, B, C and D are defined above for the Purine Derivatives of Formula (Ie), and wherein the Purine Derivatives of Formula (Iee') are substantially free of their corresponding opposite enantiomer.

In another embodiment, the Purine Derivatives of Formula (Ie) have the formula (Iee"), depicted above, wherein A, B, C and D are defined above for the Purine Derivatives of Formula (Ie), and wherein the Purine Derivatives of Formula (Iee") are substantially free of their corresponding opposite enantiomer.

In another embodiment, the Purine Derivatives of Formula (Ie) exist as a mixture of a Purine Derivative of Formula (Iee') and a Purine Derivative of Formula (Iee") wherein the amount of the Purine Derivative of Formula (Iee') exceeds the amount of the Purine Derivative of Formula (Iee").

In a further embodiment, the Purine Derivatives of Formula (Ie) exist as a mixture of a Purine Derivative of Formula (Iee') and a Purine Derivative of Formula (Iee") wherein the amount of the Purine Derivative of Formula (Iee") exceeds the amount of the Purine Derivative of Formula (Iee').

In another embodiment, the Purine Derivatives of Formula (Ie) exist as a racemic mixture of a Purine Derivative of Formula (Iee') and a Purine Derivative of Formula (Iee").

A Purine Derivative of Formula (Iee') is the corresponding other anomer of a Purine Derivative of Formula (Ie') when group A of the Purine Derivative of Formula (Iee') is the same as group A of the Purine Derivative of Formula (Ie') and when group D of the Purine Derivative of Formula (Iee') is the same as group D of the Purine Derivative of Formula (Ie').

A Purine Derivative of Formula (Ie') is the corresponding other anomer of a Purine Derivative of Formula (Iee') when group A of the Purine Derivative of Formula (Ie') is the same as group A of the Purine Derivative of Formula (Iee') and when group D of the Purine Derivative of Formula (Ie') is the same as group D of the Purine Derivative of Formula (Iee').

A Purine Derivative of Formula (Iee") is the corresponding other anomer of a Purine Derivative of Formula (Ie") when group A of the Purine Derivative of Formula (Iee") is the same as group A of the Purine Derivative of Formula (Ie") and when group D of the Purine Derivative of Formula (Iee") is the same as group D of the Purine Derivative of Formula (Ie").

A Purine Derivative of Formula (Ie") is the corresponding other anomer of a Purine Derivative of Formula (Iee") when group A of the Purine Derivative of Formula (Ie") is the same as group A of the Purine Derivative of Formula (Iee") and when group D of the Purine Derivative of Formula (Ie") is the same as group D of the Purine Derivative of Formula (Iee").

In one embodiment, the Purine Derivatives of Formula (Ie) have the formula (Iee'), depicted above, wherein A, B, C and D are defined above for the Purine Derivatives of Formula (Ie), and wherein the Purine Derivatives of Formula (Iee') are substantially free of their corresponding other anomer.

In another embodiment, the Purine Derivatives of Formula (Ie) have the formula (Iee"), depicted above, wherein A, B, C and D are defined above for the Purine Derivatives of Formula (Ie), and wherein the Purine Derivatives of Formula (Iee") are substantially free of their corresponding other anomer.

In one embodiment, the Purine Derivatives of Formula (Ie) have the formula (Ie'), depicted above, wherein A, B, C and D are defined above for the Purine Derivatives of Formula (Ie), and wherein the Purine Derivatives of Formula (Ie') are substantially free of their corresponding other anomer.

In another embodiment, the Purine Derivatives of Formula (Ie) have the formula (Ie"), depicted above, wherein A, B, C and D are defined above for the Purine Derivatives of Formula (Ie), and wherein the Purine Derivatives of Formula (Ie") are substantially free of their corresponding other anomer.

In one embodiment, the Purine Derivatives of Formula (Ie) exist as a mixture of a Purine Derivative of Formula (Ie') and a Purine Derivative of Formula (Iee') wherein the amount of the Purine Derivative of Formula (Ie') exceeds the amount of the Purine Derivative of Formula (Iee').

In another embodiment, the Purine Derivatives of Formula (Ie) exist as a mixture of a Purine Derivative of Formula (Ie') and a Purine Derivative of Formula (Iee') wherein the amount of the Purine Derivative of Formula (Iee') exceeds the amount of the Purine Derivative of Formula (Ie').

In another embodiment, the Purine Derivatives of Formula (Ie) exist as a equal mixture of a Purine Derivative of Formula (Ie') and a Purine Derivative of Formula (Iee').

In one embodiment, the Purine Derivatives of Formula (Ie) exist as a mixture of a Purine Derivative of Formula (Ie") and a Purine Derivative of Formula (Iee") wherein the amount of the Purine Derivative of Formula (Ie") exceeds the amount of the Purine Derivative of Formula (Iee").

In another embodiment, the Purine Derivatives of Formula (Ie) exist as a mixture of a Purine Derivative of Formula (Ie") and a Purine Derivative of Formula (Iee") wherein the amount of the Purine Derivative of Formula (Iee") exceeds the amount of the Purine Derivative of Formula (Ie").

In another embodiment, the Purine Derivatives of Formula (Ie) exist as a equal mixture of a Purine Derivative of Formula (Ie") and a Purine Derivative of Formula (Iee").

5.2.6 The Purine Derivatives of Formula (If)

As stated above, the present invention encompasses Purine Derivatives having the Formula (If):

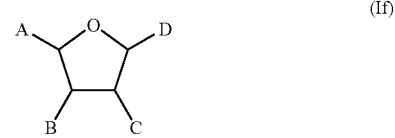

wherein A, B, C and D are defined above for the Purine Derivatives of Formula (If), and A and B are trans with respect to each other; B and C are cis with respect to each other; and C and D are cis or trans with respect to each other.

In one embodiment, $R^1$ is —$C_5$-$C_6$ monocyclic cycloalkyl.

In another embodiment, $R^1$ is cyclopentyl.

In one embodiment, $R^2$ is —H

In another embodiment $R^2$ is -halo.

In another embodiment, $R^2$ is —Cl.

In one embodiment, C and D are cis with respect to each other.

In another embodiment, C and D are trans with respect to each other.

The present invention also provides compositions comprising an effective amount of a Purine Derivative of Formula (If) and a physiologically acceptable carrier or vehicle.

The invention further provides Purine Derivatives of Formula (If) that are in isolated and purified form.

The invention still further provides methods for treating or preventing a Condition, comprising administering an effective amount of a Purine Derivative of Formula (If) to an animal in need thereof.

The invention further provides methods for reducing an animal's rate of metabolism, comprising administering an effective amount of a Purine Derivative of Formula (If) to an animal in need thereof.

The invention further provides methods protecting an animal's heart against myocardial damage during cardioplegia, comprising administering an effective amount of a Purine Derivative of Formula (If) to an animal in need thereof.

The Purine Derivatives of Formula (If) can exist in the form of a single enantiomer, for example, that depicted by either the Formula (If') or Formula (If"):

(If')

[Structure: tetrahydrofuran ring with A, O, D on top and B, C on bottom]

(If'')

[Structure: tetrahydrofuran ring with A (wedge down), O, D on top and B, C on bottom]

wherein A, B, C and D are defined above for the Purine Derivatives of Formula (If).

A Purine Derivative of Formula (If') is the corresponding opposite enantiomer of a Purine Derivative of Formula (If") when group A of the Purine Derivative of Formula (If') is the same as group A of the Purine Derivative of Formula (If") and when group D of the Purine Derivative of Formula (If') is the same as group D of the Purine Derivative of Formula (If").

A Purine Derivative of Formula (If") is the corresponding opposite enantiomer of a Purine Derivative of Formula (If') when group A of the Purine Derivatives of Formula (If") is the same as group A of the Purine Derivative of Formula (If') and when group D of the Purine Derivative of Formula (If") is the same as group D of the Purine Derivative of Formula (If').

In one embodiment, the Purine Derivatives of Formula (If) have the formula (If'), depicted above, wherein A, B, C and D are defined above for the Purine Derivatives of Formula (If), and wherein the Purine Derivatives of Formula (If') are substantially free of their corresponding enantiomer, represented by Formula (If").

In another embodiment, the Purine Derivatives of Formula (If) have the formula (If"), depicted above, wherein A, B, C and D are defined above for the Purine Derivatives of Formula (If), and wherein the Purine Derivatives of Formula (If") are substantially free of their corresponding enantiomer, represented by Formula (If').

In one embodiment, the Purine Derivatives of Formula (If) exist as a mixture of a Purine Derivative of Formula (If') and a Purine Derivative of Formula (If") wherein the amount of the Purine Derivative of Formula (If') exceeds the amount of the Purine Derivative of Formula (If").

In another embodiment, the Purine Derivatives of Formula (If) exist as a mixture of a Purine Derivative of Formula (If') and a Purine Derivative of Formula (If") wherein the amount of the Purine Derivative of Formula (If") exceeds the amount of the Purine Derivative of Formula (If').

In another embodiment, the Purine Derivatives of Formula (If) exist as a racemic mixture of a Purine Derivative of Formula (If') and a Purine Derivative of Formula (If").

In another embodiment, the Purine Derivatives of Formula (If) can exist in the form of a single enantiomer, for example, that depicted by either formula (Iff") or (Iff"'):

(Iff')

[Structure: tetrahydrofuran ring with A, O, D (wedge) on top and B, C (wedge) on bottom]

(Iff")

[Structure: tetrahydrofuran ring with A (wedge down), O, D on top and B, C on bottom]

wherein A, B, C and D are defined above for the Purine Derivatives of Formula (If).

A Purine Derivative of Formula (Iff") is the corresponding opposite enantiomer of a Purine Derivative of Formula (Iff"') when group A of the Purine Derivative of Formula (Iff") is the same as group A of the Purine Derivative of Formula (Iff"') and when group D of the Purine Derivative of Formula (If') is the same as group D of the Purine Derivative of Formula (If").

A Purine Derivative of Formula (Iff") is the corresponding opposite enantiomer of a Purine Derivative of Formula (If') when group A of the Purine Derivative of Formula (Iff") is the same as group A of the Purine Derivative of Formula (Iff') and when group D of the Purine Derivative of Formula (If') is the same as group D of the Purine Derivative of Formula (Iff').

In one embodiment, the Purine Derivatives of Formula (If) have the formula (Iff'), depicted above, wherein A, B, C and D are defined above for the Purine Derivatives of Formula (If), and wherein the Purine Derivatives of Formula (Iff') are substantially free of their corresponding opposite enantiomer.

In another embodiment, the Purine. Derivatives of Formula (If) have the formula (Iff"), depicted above, wherein A, B, C and D are defined above for the Purine Derivatives of Formula (If), and wherein the Purine Derivatives of Formula (Iff") are substantially free of their corresponding opposite enantiomer.

In another embodiment, the Purine Derivatives of Formula (If) exist as a mixture of a Purine Derivative of Formula (Iff') and a Purine Derivative of Formula (Iff") wherein the amount of the Purine Derivative of Formula (Iff') exceeds the amount of the Purine Derivative of Formula (Iff").

In a further embodiment, the Purine Derivatives of Formula (If) exist as a mixture of a Purine Derivative of Formula (If') and a Purine Derivative of Formula (Iff") wherein the amount of the Purine Derivative of Formula (Iff") exceeds the amount of the Purine Derivative of Formula (Iff').

In another embodiment, the Purine Derivatives of Formula (If) exist as a racemic mixture of a Purine Derivative of Formula (If') and a Purine Derivative of Formula (Iff").

A Purine Derivative of Formula (Iff') is the corresponding other anomer of a Purine Derivative of Formula (If') when group A of the Purine Derivative of Formula (Iff') is the same as group A of the Purine Derivative of Formula (If') and when group D of the Purine Derivative of Formula (If') is the same as group D of the Purine Derivative of Formula (If').

A Purine Derivative of Formula (If') is the corresponding other anomer of a Purine Derivative of Formula (Iff') when group A of the Purine Derivative of Formula (If') is the same as group A of the Purine Derivative of Formula (Iff') and when group D of the Purine Derivative of Formula (If') is the same as group D of the Purine Derivative of Formula (Iff').

A Purine Derivative of Formula (Iff") is the corresponding other anomer of a Purine Derivative of Formula (If") when group A of the Purine Derivative of Formula (Iff") is the same as group A of the Purine Derivative of Formula (If") and when group D of the Purine Derivative of Formula (Iff") is the same as group D of the Purine Derivative of Formula (If").

A Purine Derivative of Formula (If") is the corresponding other anomer of a Purine Derivative of Formula (Iff") when group A of the Purine Derivative of Formula (If") is the same as group A of the Purine Derivative of Formula (Iff") and when group D of the Purine Derivative of Formula (If") is the same as group D of the Purine Derivative of Formula (Iff").

In one embodiment, the Purine Derivatives of Formula (If) have the formula (Iff'), depicted above, wherein A, B, C and D are defined above for the Purine Derivatives of Formula (If), and wherein the Purine Derivatives of Formula (Iff') are substantially free of their corresponding other anomer.

In another embodiment, the Purine Derivatives of Formula (If) have the formula (Iff"), depicted above, wherein A, B, C and D are defined above for the Purine Derivatives of Formula (If), and wherein the Purine Derivatives of Formula (Iff") are substantially free of their corresponding other anomer.

In one embodiment, the Purine Derivatives of Formula (If) have the formula (If'), depicted above, wherein A, B, C and D are defined above for the Purine Derivatives of Formula (If), and wherein the Purine Derivatives of Formula (If') are substantially free of their corresponding other anomer.

In another embodiment, the Purine Derivatives of Formula (If) have the formula (If"), depicted above, wherein A, B, C and D are defined above for the Purine Derivatives of Formula (If), and wherein the Purine Derivatives of Formula (If") are substantially free of their corresponding other anomer.

In one embodiment, the Purine Derivatives of Formula (If) exist as a mixture of a Purine Derivative of Formula (If') and a Purine Derivative of Formula (Iff') wherein the amount of the Purine Derivative of Formula (If') exceeds the amount of the Purine Derivative of Formula (Iff').

In another embodiment, the Purine Derivatives of Formula (If) exist as a mixture of a Purine Derivative of Formula (If') and a Purine Derivative of Formula (Iff') wherein the amount of the Purine Derivative of Formula (Iff') exceeds the amount of the Purine Derivative of Formula (If').

In another embodiment, the Purine Derivatives of Formula (If) exist as a equal mixture of a Purine Derivative of Formula (If') and a Purine Derivative of Formula (Iff').

In one embodiment, the Purine Derivatives of Formula (If) exist as a mixture of a Purine Derivative of Formula (If") and a Purine Derivative of Formula (Iff") wherein the amount of the Purine Derivative of Formula (If") exceeds the amount of the Purine Derivative of Formula (Iff").

In another embodiment, the Purine Derivatives of Formula (If) exist as a mixture of a Purine Derivative of Formula (If") and a Purine Derivative of Formula (Iff") wherein the amount of the Purine Derivative of Formula (Iff") exceeds the amount of the Purine Derivative of Formula (If").

In another embodiment, the Purine Derivatives of Formula (If) exist as a equal mixture of a Purine Derivative of Formula (If") and a Purine Derivative of Formula (Iff").

Illustrative Purine Derivatives of Formula (If) include the compounds listed below:

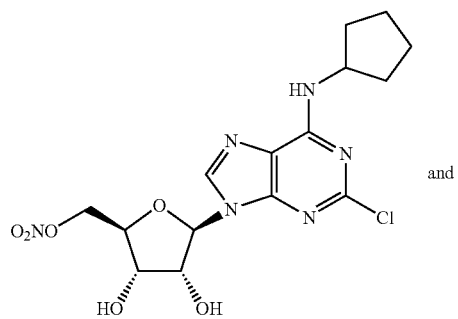

16 and

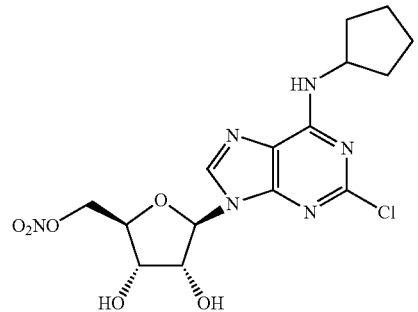

17 and pharmaceutically acceptable salts thereof.

5.2.7 The Purine Derivatives of Formula (Ig)

As stated above, the present invention encompasses Purine Derivatives having the Formula (Ig):

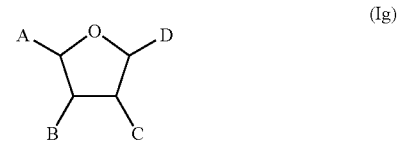

(Ig)

wherein A, B, C and D are defined above for the Purine Derivatives of Formula (Ig), and A and B are trans with respect to each other; B and C are cis with respect to each other; and C and D are cis or trans with respect to each other.

In one embodiment, $R^2$ is —H

In another embodiment $R^2$ is -halo.

In a specific embodiment, $R^2$ is —Cl.

In one embodiment, C and D are cis with respect to each other.

In another embodiment, C and D are trans with respect to each other.

The present invention also provides compositions comprising an effective amount of a Purine Derivative of Formula (Ig) and a physiologically acceptable carrier or vehicle.

The invention further provides Purine Derivatives of Formula (Ig) that are in isolated and purified form.

The invention still further provides methods for treating or preventing a Condition, comprising administering an effective amount of a Purine Derivative of Formula (Ig) to an animal in need thereof.

The invention further provides methods for reducing an animal's rate of metabolism, comprising administering an effective amount of a Purine Derivative of Formula (Ig) to an animal in need thereof.

The invention further provides methods protecting an animal's heart against myocardial damage during cardioplegia, comprising administering an effective amount of a Purine Derivative of Formula (Ig) to an animal in need thereof.

The Purine Derivatives of Formula (Ig) can exist in the form of a single enantiomer, for example, that depicted by either the Formula (Ig') or Formula (Ig"):

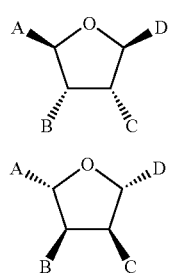

(Ig')

(Ig")

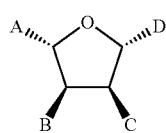

wherein A, B, C and D are defined above for the Purine Derivatives of Formula (Ig).

A Purine Derivative of Formula (Ig') is the corresponding opposite enantiomer of a Purine Derivative of Formula (Ig") when group A of the Purine Derivative of Formula (Ig') is the same as group A of the Purine Derivative of Formula (Ig") and when group D of the Purine Derivative of Formula (Ig') is the same as group D of the Purine Derivative of Formula (Ig").

A Purine Derivative of Formula (Ig") is the corresponding opposite enantiomer of a Purine Derivative of Formula (Ig') when group A of the Purine Derivatives of Formula (Ig") is the same as group A of the Purine Derivative of Formula (Ig') and when group D of the Purine Derivative of Formula (Ig") is the same as group D of the Purine Derivative of Formula (Ig').

In one embodiment, the Purine Derivatives of Formula (Ig) have the formula (Ig'), depicted above, wherein A, B, C and D are defined above for the Purine Derivatives of Formula (Ig), and wherein the Purine Derivatives of Formula (Ig') are substantially free of their corresponding enantiomer, represented by Formula (Ig").

In another embodiment, the Purine Derivatives of Formula (Ig) have the formula (Ig"), depicted above, wherein A, B, C and D are defined above for the Purine Derivatives of Formula (Ig), and wherein the Purine Derivatives of Formula (Ig") are substantially free of their corresponding enantiomer, represented by Formula (Ig').

In one embodiment, the Purine Derivatives of Formula (Ig) exist as a mixture of a Purine Derivative of Formula (Ig') and a Purine Derivative of Formula (Ig") wherein the amount of the Purine Derivative of Formula (Ig') exceeds the amount of the Purine Derivative of Formula (Ig").

In another embodiment, the Purine Derivatives of Formula (Ig) exist as a mixture of a Purine Derivative of Formula (Ig') and a Purine Derivative of Formula (Ig") wherein the amount of the Purine Derivative of Formula (Ig") exceeds the amount of the Purine Derivative of Formula (Ig').

In another embodiment, the Purine Derivatives of Formula (Ig) exist as a racemic mixture of a Purine Derivative of Formula (Ig') and a Purine Derivative of Formula (Ig").

In another embodiment, the Purine Derivatives of Formula (Ig) can exist in the form of a single enantiomer, for example, that depicted by either formula (Igg') or (Igg"):

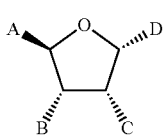

(Igg')

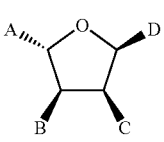

(Igg")

wherein A, B, C and D are defined above for the Purine Derivatives of Formula (Ig).

A Purine Derivative of Formula (Igg') is the corresponding opposite enantiomer of a Purine Derivative of Formula (Igg") when group A of the Purine Derivative of Formula (Igg') is the same as group A of the Purine Derivative of Formula (Igg") and when group D of the Purine Derivative of Formula (Igg') is the same as group D of the Purine Derivative of Formula (Igg").

A Purine Derivative of Formula (Igg") is the corresponding opposite enantiomer of a Purine Derivative of Formula (Igg') when group A of the Purine Derivative of Formula (Igg") is the same as group A of the Purine Derivative of Formula (Igg') and when group D of the Purine Derivative of Formula (Igg") is the same as group D of the Purine Derivative of Formula (Igg').

In one embodiment, the Purine Derivatives of Formula (Ig) have the formula (Igg'), depicted above, wherein A, B, C and D are defined above for the Purine Derivatives of Formula (Ig), and wherein the Purine Derivatives of Formula (Igg') are substantially free of their corresponding opposite enantiomer.

In another embodiment, the Purine Derivatives of Formula (Ig) have the formula (Igg"), depicted above, wherein A, B, C and D are defined above for the Purine Derivatives of Formula (Ig), and wherein the Purine Derivatives of Formula (Igg") are substantially free of their corresponding opposite enantiomer.

In another embodiment, the Purine Derivatives of Formula (Ig) exist as a mixture of a Purine Derivative of Formula (Igg') and a Purine Derivative of Formula (Igg") wherein the amount of the Purine Derivative of Formula (Igg') exceeds the amount of the Purine Derivative of Formula (Igg").

In a further embodiment, the Purine Derivatives of Formula (Ig) exist as a mixture of a Purine Derivative of Formula (Igg') and a Purine Derivative of Formula (Igg") wherein the amount of the Purine Derivative of Formula (Igg") exceeds the amount of the Purine Derivative of Formula (Igg').

In another embodiment, the Purine Derivatives of Formula (Ig) exist as a racemic mixture of a Purine Derivative of Formula (Igg') and a Purine Derivative of Formula (Igg").

A Purine Derivative of Formula (Igg') is the corresponding other anomer of a Purine Derivative of Formula (Ig') when group A of the Purine Derivative of Formula (Igg') is the same as group A of the Purine Derivative of Formula (Ig') and when group D of the Purine Derivative of Formula (Igg') is the same as group D of the Purine Derivative of Formula (Ig').

A Purine Derivative of Formula (Ig') is the corresponding other anomer of a Purine Derivative of Formula (Igg') when group A of the Purine Derivative of Formula (Ig') is the same as group A of the Purine Derivative of Formula (Igg') and when group D of the Purine Derivative of Formula (Ig') is the same as group D of the Purine Derivative of Formula (Igg').

A Purine Derivative of Formula (Igg") is the corresponding other anomer of a Purine Derivative of Formula (Ig") when group A of the Purine Derivative of Formula (Igg") is the same as group A of the Purine Derivative of Formula (Ig") and when group D of the Purine Derivative of Formula (Igg") is the same as group D of the Purine Derivative of Formula (Ig").

A Purine Derivative of Formula (Ig") is the corresponding other anomer of a Purine Derivative of Formula (Igg") when group A of the Purine Derivative of Formula (Ig") is the same as group A of the Purine Derivative of Formula (Igg") and when group D of the Purine Derivative of Formula (Ig") is the same as group D of the Purine Derivative of Formula (Igg").

In one embodiment, the Purine Derivatives of Formula (Ig) have the formula (Igg'), depicted above, wherein A, B, C and D are defined above for the Purine Derivatives of Formula (Ig), and wherein the Purine Derivatives of Formula (Igg') are substantially free of their corresponding other anomer.

In another embodiment, the Purine Derivatives of Formula (Ig) have the formula (Igg"), depicted above, wherein A, B, C and D are defined above for the Purine Derivatives of Formula (Ig), and wherein the Purine Derivatives of Formula (Igg") are substantially free of their corresponding other anomer.

In one embodiment, the Purine Derivatives of Formula (Ig) have the formula (Ig'), depicted above, wherein A, B, C and D are defined above for the Purine Derivatives of Formula (Ig), and wherein the Purine Derivatives of Formula (Ig') are substantially free of their corresponding other anomer.

In another embodiment, the Purine Derivatives of Formula (Ig) have the formula (Ig"), depicted above, wherein A, B, C and D are defined above for the Purine Derivatives of Formula (Ig), and wherein the Purine Derivatives of Formula (Ig") are substantially free of their corresponding other anomer.

In one embodiment, the Purine Derivatives of Formula (Ig) exist as a mixture of a Purine Derivative of Formula (Ig') and a Purine Derivative of Formula (Igg') wherein the amount of the Purine Derivative of Formula (Ig') exceeds the amount of the Purine Derivative of Formula (Igg').

In another embodiment, the Purine Derivatives of Formula (Ig) exist as a mixture of a Purine Derivative of Formula (Ig') and a Purine Derivative of Formula (Igg') wherein the amount of the Purine Derivative of Formula (Igg') exceeds the amount of the Purine Derivative of Formula (Ig').

In another embodiment, the Purine Derivatives of Formula (Ig) exist as a equal mixture of a Purine Derivative of Formula (Ig') and a Purine Derivative of Formula (Igg').

In one embodiment, the Purine Derivatives of Formula (Ig) exist as a mixture of a Purine Derivative of Formula (Ig") and a Purine Derivative of Formula (Igg") wherein the amount of the Purine Derivative of Formula (Ig") exceeds the amount of the Purine Derivative of Formula (Igg").

In another embodiment, the Purine Derivatives of Formula (Ig) exist as a mixture of a Purine Derivative of Formula (Ig") and a Purine Derivative of Formula (Igg") wherein the amount of the Purine Derivative of Formula (Igg") exceeds the amount of the Purine Derivative of Formula (Ig").

In another embodiment, the Purine Derivatives of Formula (Ig) exist as a equal mixture of a Purine Derivative of Formula (Ig") and a Purine Derivative of Formula (Igg").

Illustrative Purine Derivatives of Formula (Ig) include the compounds listed below:

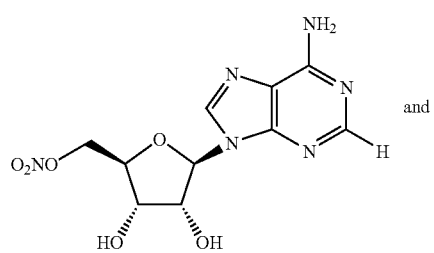

18 and

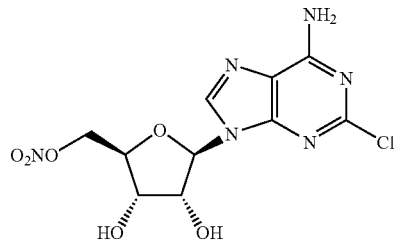

19 and pharmaceutically acceptable salts thereof.

5.2.8 The Purine Derivatives of Formula (Ih)

As stated above, the present invention encompasses Purine Derivatives having the Formula (Ih):

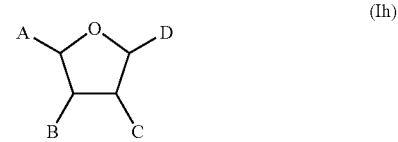

(Ih)

wherein A, B, C and D are defined above for the Purine Derivatives of Formula (Ih), and A and B are trans with respect to each other; B and C are cis with respect to each other; and C and D are cis or trans with respect to each other.

In one embodiment, $R^1$ is cyclopent-1-ol-2-yl.

In another embodiment $R^1$ is cyclopent-1-ol-3-yl.

In one embodiment, C and D are cis with respect to each other.

In another embodiment, C and D are trans with respect to each other.

The present invention also provides compositions comprising an effective amount of a Purine Derivative of Formula (Ih) and a physiologically acceptable carrier or vehicle.

The invention further provides Purine Derivatives of Formula (Ih) that are in isolated and purified form.

The invention still further provides methods for treating or preventing a Condition, comprising administering an effective amount of a Purine Derivative of Formula (Ih) to an animal in need thereof.

The invention further provides methods for reducing an animal's rate of metabolism, comprising administering an effective amount of a Purine Derivative of Formula (Ih) to an animal in need thereof.

The invention further provides methods protecting an animal's heart against myocardial damage during cardioplegia, comprising administering an effective amount of a Purine Derivative of Formula (Ih) to an animal in need thereof.

The Purine Derivatives of Formula (Ih) can exist in the form of a single enantiomer, for example, that depicted by either the Formula (Ih') or Formula (Ih"):

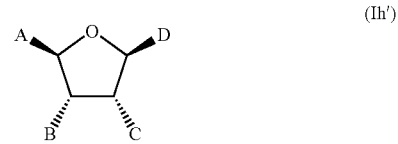

(Ih')

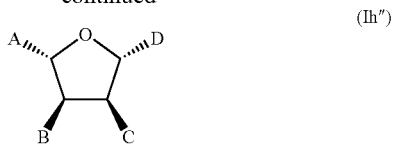

wherein A, B, C and D are defined above for the Purine Derivatives of Formula (Ih).

A Purine Derivative of Formula (Ih') is the corresponding opposite enantiomer of a Purine Derivative of Formula (Ih") when group A of the Purine Derivative of Formula (Ih') is the same as group A of the Purine Derivative of Formula (Ih") and when group D of the Purine Derivative of Formula (Ih') is the same as group D of the Purine Derivative of Formula (Ib").

A Purine Derivative of Formula (Ih") is the corresponding opposite enantiomer of a Purine Derivative of Formula (Ih') when group A of the Purine Derivatives of Formula (Ib") is the same as group A of the Purine Derivative of Formula (Ih') and when group D of the Purine Derivative of Formula (Ih") is the same as group D of the Purine Derivative of Formula (Ih').

In one embodiment, the Purine Derivatives of Formula (Ih) have the formula (Ih'), depicted above, wherein A, B, C and D are defined above for the Purine Derivatives of Formula (Ih), and wherein the Purine Derivatives of Formula (Ih') are substantially free of their corresponding enantiomer, represented by Formula (Ih").

In another embodiment, the Purine Derivatives of Formula (Ih) have the formula (Ih"), depicted above, wherein A, B, C and D are defined above for the Purine Derivatives of Formula (Ih), and wherein the Purine Derivatives of Formula (Ih") are substantially free of their corresponding enantiomer, represented by Formula (Ih').

In one embodiment, the Purine Derivatives of Formula (Ih) exist as a mixture of a Purine Derivative of Formula (Ih') and a Purine Derivative of Formula (Ih") wherein the amount of the Purine Derivative of Formula (Ih') exceeds the amount of the Purine Derivative of Formula (Ih").

In another embodiment, the Purine Derivatives of Formula (Ih) exist as a mixture of a Purine Derivative of Formula (Ih') and a Purine Derivative of Formula (Ih") wherein the amount of the Purine Derivative of Formula (Ih") exceeds the amount of the Purine Derivative of Formula (Ih').

In another embodiment, the Purine Derivatives of Formula (Ih) exist as a racemic mixture of a Purine Derivative of Formula (Ih') and a Purine Derivative of Formula (Ih").

In another embodiment, the Purine Derivatives of Formula (Ih) can exist in the form of a single enantiomer, for example, that depicted by either formula (Ihh') or (Ihh"):

(Ihh')

(Ihh")

wherein A, B, C and D are defined above for the Purine Derivatives of Formula (Ih).

A Purine Derivative of Formula (Ihh') is the corresponding opposite enantiomer of a Purine Derivative of Formula (Ihh") when group A of the Purine Derivative of Formula (Ihh') is the same as group A of the Purine Derivative of Formula (Ihh") and when group D of the Purine Derivative of Formula (Ihh') is the same as group D of the Purine Derivative of Formula (Ihh").

A Purine Derivative of Formula (Ihh") is the corresponding opposite enantiomer of a Purine Derivative of Formula (Ihh') when group A of the Purine Derivative of Formula (Ihh") is the same as group A of the Purine Derivative of Formula (Ihh') and when group D of the Purine Derivative of Formula (Ihh") is the same as group D of the Purine Derivative of Formula (Ihh').

In one embodiment, the Purine Derivatives of Formula (Ih) have the formula (Ihh'), depicted above, wherein A, B, C and D are defined above for the Purine Derivatives of Formula (Ih), and wherein the Purine Derivatives of Formula (Ihh') are substantially free of their corresponding opposite enantiomer.

In another embodiment, the Purine Derivatives of Formula (Ih) have the formula (Ihh"), depicted above, wherein A, B, C and D are defined above for the Purine Derivatives of Formula (Ih), and wherein the Purine Derivatives of Formula (Ihh") are substantially free of their corresponding opposite enantiomer.

In another embodiment, the Purine Derivatives of Formula (Ih) exist as a mixture of a Purine Derivative of Formula (Ihh') and a Purine Derivative of Formula (Ihh") wherein the amount of the Purine Derivative of Formula (Ihh') exceeds the amount of the Purine Derivative of Formula (Ihh").

In a further embodiment, the Purine Derivatives of Formula (Ih) exist as a mixture of a Purine Derivative of Formula (Ihh') and a Purine Derivative of Formula (Ihh") wherein the amount of the Purine Derivative of Formula (Ihh") exceeds the amount of the Purine Derivative of Formula (Ihh').

In another embodiment, the Purine Derivatives of Formula (Ih) exist as a racemic mixture of a Purine Derivative of Formula (Ihh') and a Purine Derivative of Formula (Ihh").

A Purine Derivative of Formula (Ihh') is the corresponding other anomer of a Purine Derivative of Formula (Ih') when group A of the Purine Derivative of Formula (Ihh') is the same as group A of the Purine Derivative of Formula (Ih') and when group D of the Purine Derivative of Formula (Ihh') is the same as group D of the Purine Derivative of Formula (Ih').

A Purine Derivative of Formula (Ih') is the corresponding other anomer of a Purine Derivative of Formula (Ihh') when group A of the Purine Derivative of Formula (Ih') is the same as group A of the Purine Derivative of Formula (Ihh') and when group D of the Purine Derivative of Formula (Ih') is the same as group D of the Purine Derivative of Formula (Ihh').

A Purine Derivative of Formula (Ihh") is the corresponding other anomer of a Purine Derivative of Formula (Ih") when group A of the Purine Derivative of Formula (Ihh") is the same as group A of the Purine Derivative of Formula (Ih") and when group D of the Purine Derivative of Formula (Ihh") is the same as group D of the Purine Derivative of Formula (Ib").

A Purine Derivative of Formula (Ih") is the corresponding other anomer of a Purine Derivative of Formula (Ihh") when group A of the Purine Derivative of Formula (Ih") is the same as group A of the Purine Derivative of Formula (Ihh") and when group D of the Purine Derivative of Formula (Ih") is the same as group D of the Purine Derivative of Formula (Ihh").

In one embodiment, the Purine Derivatives of Formula (Ih) have the formula (Ihh'), depicted above, wherein A, B, C and D are defined above for the Purine Derivatives of Formula (Ih), and wherein the Purine Derivatives of Formula (Ihh') are substantially free of their corresponding other anomer.

In another embodiment, the Purine Derivatives of Formula (Ih) have the formula (Ihh"), depicted above, wherein A, B, C and D are defined above for the Purine Derivatives of Formula (Ih), and wherein the Purine Derivatives of Formula (Ihh") are substantially free of their corresponding other anomer.

In one embodiment, the Purine Derivatives of Formula (Ih) have the formula (Ih'), depicted above, wherein A, B, C and D are defined above for the Purine Derivatives of Formula (Ih), and wherein the Purine Derivatives of Formula (Ih') are substantially free of their corresponding other anomer.

In another embodiment, the Purine Derivatives of Formula (Ih) have the formula (Ih"), depicted above, wherein A, B, C and D are defined above for the Purine Derivatives of Formula (Ih), and wherein the Purine Derivatives of Formula (Ih") are substantially free of their corresponding other anomer.

In one embodiment, the Purine Derivatives of Formula (Ih) exist as a mixture of a Purine Derivative of Formula (Ih') and a Purine Derivative of Formula (Ihh') wherein the amount of the Purine Derivative of Formula (Ih') exceeds the amount of the Purine Derivative of Formula (Ihh').

In another embodiment, the Purine Derivatives of Formula (Ih) exist as a mixture of a Purine Derivative of Formula (Ih') and a Purine Derivative of Formula (Ihh') wherein the amount of the Purine Derivative of Formula (Ihh') exceeds the amount of the Purine Derivative of Formula (Ih').

In another embodiment, the Purine Derivatives of Formula (Ih) exist as a equal mixture of a Purine Derivative of Formula (Ih') and a Purine Derivative of Formula (Ihh').

In one embodiment, the Purine Derivatives of Formula (Ih) exist as a mixture of a Purine Derivative of Formula (Ih") and a Purine Derivative of Formula (Ihh") wherein the amount of the Purine Derivative of Formula (Ih") exceeds the amount of the Purine Derivative of Formula (Ihh").

In another embodiment, the Purine Derivatives of Formula (Ih) exist as a mixture of a Purine Derivative of Formula (Ih") and a Purine Derivative of Formula (Ihh") wherein the amount of the Purine Derivative of Formula (Ihh") exceeds the amount of the Purine Derivative of Formula (Ih").

In another embodiment, the Purine Derivatives of Formula (Ih) exist as a equal mixture of a Purine Derivative of Formula (Ih") and a Purine Derivative of Formula (Ihh").

Illustrative Purine Derivatives of Formula (Ih) include the compounds listed below:

26
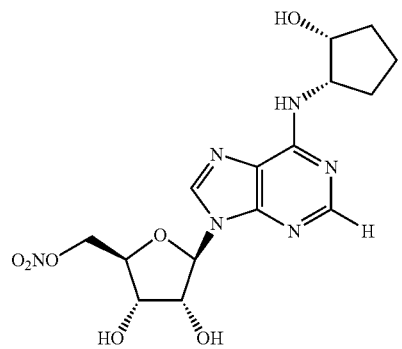

27
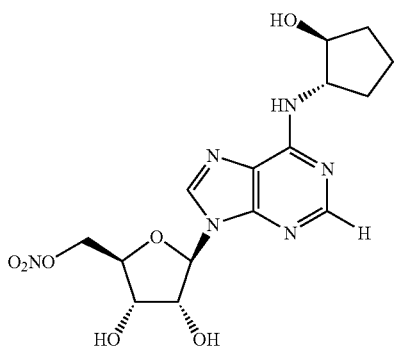

28
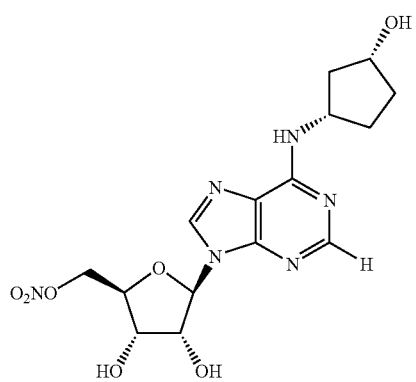

29
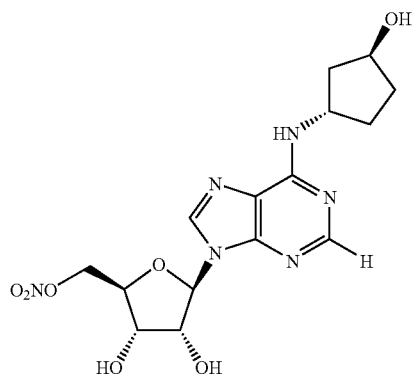

30
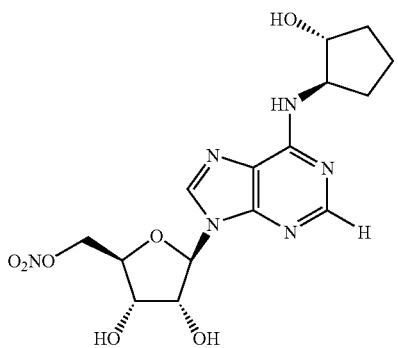

-continued

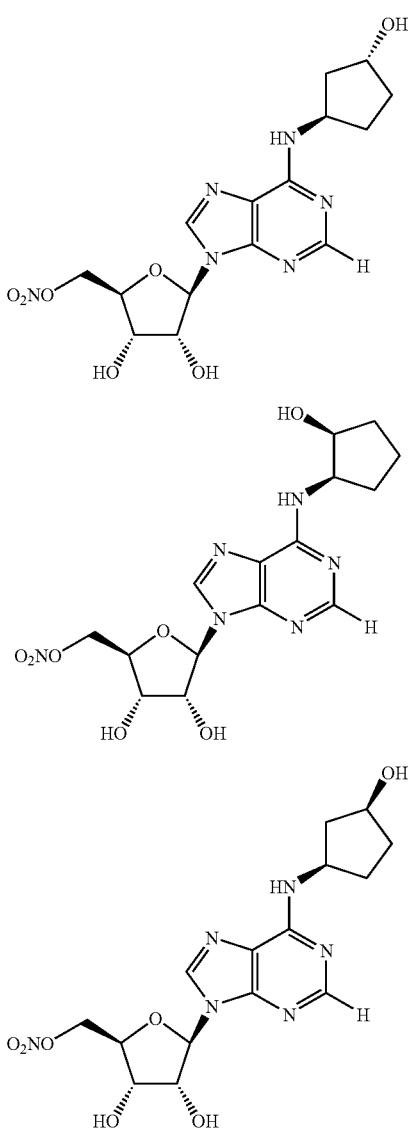

and pharmaceutically acceptable salts thereof.

5.2.9 The Purine Derivatives of Formula (II)

As stated above, the present invention encompasses Purine Derivatives having the Formula (II):

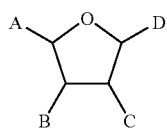
(II)

wherein A, B, C and D are defined above for the Purine Derivatives of Formula (II), and A and B are trans with respect to each other; B and C are cis with respect to each other; and C and D are cis or trans with respect to each other.

In one embodiment, $R^1$ is —H.

In another embodiment, $R^1$ is —$C_1$-$C_{10}$ alkyl.

In still another embodiment, $R^1$ is —$(CH_2)_m$—$(C_8$-$C_{12}$ bicyclic cycloalkyl) or —$(CH_2)_m$—$(C_8$-$C_{12}$ bicyclic cycloalkenyl).

In another embodiment, $R^2$ is —$OR^4$ or —SR.

In another embodiment, $R^2$ is —$NHNHC(O)R^3$, —$NHNHC(O)OR^7$ or —$NHNHC(O)NHR^3$.

In yet another embodiment, $R^2$ is —NH—N=$C(R^5)R^6$.

In a specific embodiment, $R^2$ is —NH—N=CH-cyclopropyl.

In one embodiment, C and D are cis with respect to each other.

In another embodiment, C and D are trans with respect to each other.

The present invention also provides compositions comprising an effective amount of a Purine Derivative of Formula (II) and a physiologically acceptable carrier or vehicle.

The invention further provides Purine Derivatives of Formula (II) that are in isolated and purified form.

The invention still further provides methods for treating or preventing a Condition, comprising administering an effective amount of a Purine Derivative of Formula (II) to an animal in need thereof.

The invention further provides methods for reducing an animal's rate of metabolism, comprising administering an effective amount of a Purine Derivative of Formula (II) to an animal in need thereof.

The invention further provides methods protecting an animal's heart against myocardial damage during cardioplegia, comprising administering an effective amount of a Purine Derivative of Formula (II) to an animal in need thereof.

The Purine Derivatives of Formula (II) can exist in the form of a single enantiomer, for example, that depicted by either the Formula (II') or Formula (II"):

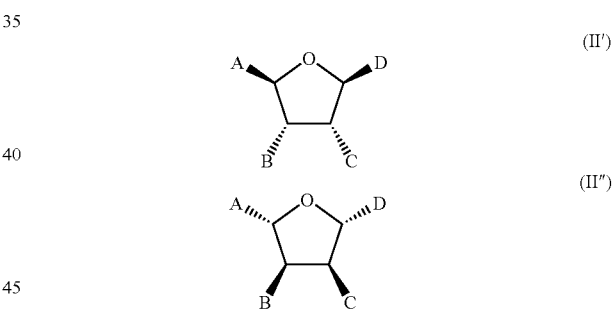

wherein A, B, C and D are defined above for the Purine Derivatives of Formula (II).

A Purine Derivative of Formula (II') is the corresponding opposite enantiomer of a Purine Derivative of Formula (II") when group A of the Purine Derivative of Formula (II') is the same as group A of the Purine Derivative of Formula (II") and when group D of the Purine Derivative of Formula (II') is the same as group D of the Purine Derivative of Formula (II").

A Purine Derivative of Formula (II") is the corresponding opposite enantiomer of a Purine Derivative of Formula (II') when group A of the Purine Derivatives of Formula (II") is the same as group A of the Purine Derivative of Formula (IT) and when group D of the Purine Derivative of Formula (II") is the same as group D of the Purine Derivative of Formula (II').

In one embodiment, the Purine Derivatives of Formula (II) have the formula (II'), depicted above, wherein A, B, C and D are defined above for the Purine Derivatives of Formula (II), and wherein the Purine Derivatives of Formula (II') are substantially free of their corresponding enantiomer, represented by Formula (II").

In another embodiment, the Purine Derivatives of Formula (II) have the formula (II″), depicted above, wherein A, B, C and D are defined above for the Purine Derivatives of Formula (II), and wherein the Purine Derivatives of Formula (II″) are substantially free of their corresponding enantiomer, represented by Formula (II′).

In one embodiment, the Purine Derivatives of Formula (II) exist as a mixture of a Purine Derivative of Formula (II′) and a Purine Derivative of Formula (II″) wherein the amount of the Purine Derivative of Formula (II′) exceeds the amount of the Purine Derivative of Formula (II″).

In another embodiment, the Purine Derivatives of Formula (II) exist as a mixture of a Purine Derivative of Formula (II′) and a Purine Derivative of Formula (II″) wherein the amount of the Purine Derivative of Formula (II″) exceeds the amount of the Purine Derivative of Formula (II′).

In another embodiment, the Purine Derivatives of Formula (II) exist as a racemic mixture of a Purine Derivative of Formula (II′) and a Purine Derivative of Formula (II″).

In another embodiment, the Purine Derivatives of Formula (II) can exist in the form of a single enantiomer, for example, that depicted by either formula (IIa′) or (IIa″):

$$\text{(IIa')}$$

$$\text{(IIa'')}$$

wherein A, B, C and D are defined above for the Purine Derivatives of Formula (II).

A Purine Derivative of Formula (IIa′) is the corresponding opposite enantiomer of a Purine Derivative of Formula (IIa″) when group A of the Purine Derivative of Formula (IIa′) is the same as group A of the Purine Derivative of Formula (IIa″) and when group D of the Purine Derivative of Formula (IIa′) is the same as group D of the Purine Derivative of Formula (IIa″).

A Purine Derivative of Formula (IIa″) is the corresponding opposite enantiomer of a Purine Derivative of Formula (IIa′) when group A of the Purine Derivative of Formula (IIa″) is the same as group A of the Purine Derivative of Formula (IIa′) and when group D of the Purine Derivative of Formula (IIa″) is the same as group D of the Purine Derivative of Formula (IIa′).

In one embodiment, the Purine Derivatives of Formula (II) have the formula (IIa′), depicted above, wherein A, B, C and D are defined above for the Purine Derivatives of Formula (II), and wherein the Purine Derivatives of Formula (IIa′) are substantially free of their corresponding opposite enantiomer.

In another embodiment, the Purine Derivatives of Formula (II) have the formula (IIa″), depicted above, wherein A, B, C and D are defined above for the Purine Derivatives of Formula (II), and wherein the Purine Derivatives of Formula (IIa″) are substantially free of their corresponding opposite enantiomer.

In another embodiment, the Purine Derivatives of Formula (II) exist as a mixture of a Purine Derivative of Formula (IIa′) and a Purine Derivative of Formula (IIa″) wherein the amount of the Purine Derivative of Formula (IIa′) exceeds the amount of the Purine Derivative of Formula (IIa″).

In a further embodiment, the Purine Derivatives of Formula (II) exist as a mixture of a Purine Derivative of Formula (IIa′) and a Purine Derivative of Formula (IIa″) wherein the amount of the Purine Derivative of Formula (IIa″) exceeds the amount of the Purine Derivative of Formula (Ia′).

In another embodiment, the Purine Derivatives of Formula (II) exist as a racemic mixture of a Purine Derivative of Formula (IIa′) and a Purine Derivative of Formula (IIa″).

A Purine Derivative of Formula (IIa′) is the corresponding other anomer of a Purine Derivative of Formula (II′) when group A of the Purine Derivative of Formula (II′) is the same as group A of the Purine Derivative of Formula (II′) and when group D of the Purine Derivative of Formula (IIa′) is the same as group D of the Purine Derivative of Formula (II′).

A Purine Derivative of Formula (II′) is the corresponding other anomer of a Purine Derivative of Formula (IIa′) when group A of the Purine Derivative of Formula (II′) is the same as group A of the Purine Derivative of Formula (IIa′) and when group D of the Purine Derivative of Formula (II′) is the same as group D of the Purine Derivative of Formula (IIa′).

A Purine Derivative of Formula (IIa″) is the corresponding other anomer of a Purine Derivative of Formula (II″) when group A of the Purine Derivative of Formula (IIa″) is the same as group A of the Purine Derivative of Formula (II″) and when group D of the Purine Derivative of Formula (IIa″) is the same as group D of the Purine Derivative of Formula (II″).

A Purine Derivative of Formula (II″) is the corresponding other anomer of a Purine Derivative of Formula (IIa″) when group A of the Purine Derivative of Formula (II″) is the same as group A of the Purine Derivative of Formula (IIa″) and when group D of the Purine Derivative of Formula (II″) is the same as group D of the Purine Derivative of Formula (IIa″).

In one embodiment, the Purine Derivatives of Formula (II) have the formula (IIa′), depicted above, wherein A, B, C and D are defined above for the Purine Derivatives of Formula (II), and wherein the Purine Derivatives of Formula (IIa′) are substantially free of their corresponding other anomer.

In another embodiment, the Purine Derivatives of Formula (II) have the formula (IIa″), depicted above, wherein A, B, C and D are defined above for the Purine Derivatives of Formula (II), and wherein the Purine Derivatives of Formula (IIa″) are substantially free of their corresponding other anomer.

In one embodiment, the Purine Derivatives of Formula (II) have the formula (II′), depicted above, wherein A, B, C and D are defined above for the Purine Derivatives of Formula (II), and wherein the Purine Derivatives of Formula (II′) are substantially free of their corresponding other anomer.

In another embodiment, the Purine Derivatives of Formula (II) have the formula (II″), depicted above, wherein A, B, C and D are defined above for the Purine Derivatives of Formula (II), and wherein the Purine Derivatives of Formula (II″) are substantially free of their corresponding other anomer.

In one embodiment, the Purine Derivatives of Formula (II) exist as a mixture of a Purine Derivative of Formula (II′) and a Purine Derivative of Formula (IIa′) wherein the amount of the Purine Derivative of Formula (II′) exceeds the amount of the Purine Derivative of Formula (IIa′)

In another embodiment, the Purine Derivatives of Formula (II) exist as a mixture of a Purine Derivative of Formula (II′) and a Purine Derivative of Formula (IIa′) wherein the amount of the Purine Derivative of Formula (IIa′) exceeds the amount of the Purine Derivative of Formula (II′).

In another embodiment, the Purine Derivatives of Formula (IIa) exist as a equal mixture of a Purine Derivative of Formula (II′) and a Purine Derivative of Formula (IIa′).

In one embodiment, the Purine Derivatives of Formula (IIa) exist as a mixture of a Purine Derivative of Formula (II″)

and a Purine Derivative of Formula (IIa") wherein the amount of the Purine Derivative of Formula (II") exceeds the amount of the Purine Derivative of Formula (IIa").

In another embodiment, the Purine Derivatives of Formula (IIa) exist as a mixture of a Purine Derivative of Formula (II") and a Purine Derivative of Formula (IIa") wherein the amount of the Purine Derivative of Formula (IIa") exceeds the amount of the Purine Derivative of Formula (II").

In another embodiment, the Purine Derivatives of Formula (IIa) exist as a equal mixture of a Purine Derivative of Formula (II") and a Purine Derivative of Formula (IIa").

A first subclass of the Purine Derivatives of Formula (II) is that wherein one occurrence of $R^1$ is —H.

A second subclass of the Purine Derivatives of Formula (II) is that wherein both $R^1$ groups together with the carbon atom to which they are attached, join to form a —$C_3$-$C_8$ monocyclic cycloalkyl.

A third subclass of the Purine Derivatives of Formula (II) is that wherein $R^2$ is —NH—N=C($R^5$)$R^6$

5.2.10 The Purine Derivatives of Formula (III)

As stated above, the present invention encompasses Purine Derivatives having the Formula (III):

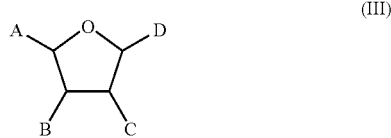

(III)

wherein A, B, C and D are defined above for the Purine Derivatives of Formula (m), and A and B are trans with respect to each other; B and C are cis with respect to each other; and C and D are cis or trans with respect to each other.

In one embodiment, $R^1$ is —H.

In another embodiment, $R^1$ is —$C_1$-$C_{10}$ alkyl.

In another embodiment, $R^1$ is —$(CH_2)_m$-(3- to 7-membered monocyclic heterocycle) or —$(CH_2)_m$-(8- to 12-membered bicyclic heterocycle).

In still another embodiment, $R^1$ is —$(CH_2)_n$—($C_3$-$C_8$ monocyclic cycloalkyl) or —$(CH_2)_m$—($C_3$-$C_8$ monocyclic cycloalkenyl), In a further embodiment, $R^1$ is —$(CH_2)_m$—($C_8$-$C_{12}$ bicyclic cycloalkyl) or —$(CH_2)_n$—($C_8$-$C_{12}$ bicyclic cycloalkenyl).

In another embodiment, $R^1$ is —$(CH_2)_m$-aryl.

In still another embodiment, two $R^1$ groups, together with the carbon atom to which they are attached, form a —$C_3$-$C_8$ monocyclic cycloalkyl, a —$C_3$-$C_8$ monocyclic cycloalkenyl, a —$C_8$-$C_{12}$ bicyclic cycloalkyl, or a —$C_8$-$C_{12}$ bicyclic cycloalkenyl.

In a specific embodiment, $R^1$ is cyclopentyl.

In one embodiment, m is 0.

In another embodiment, m is 1.

In another embodiment, m is 2.

In still another embodiment, m is 3.

In one embodiment, $R^2$ is -halo.

In a specific embodiment, $R^2$ is —Cl.

In one embodiment, $R^2$ is —H.

In another embodiment, $R^2$ is —CN.

In another embodiment, $R^2$ is —N($R^4$)$_2$, —$OR^4$ or —$SR^4$.

In a further embodiment, $R^2$ is —NHC(O)$R^4$, —NHC(O)$OR^4$ or —NHC(O)NHR$^4$.

In another embodiment, $R^2$ is —NHNHC(O)$R^4$, —NHNHC(O)$OR^4$ or —NHNHC(O)NHR$^4$. In yet another embodiment, $R^2$ is —NH—N=C($R^6$)$R^7$.

In a specific embodiment, $R^2$ is —NH—N=CH-cyclopropyl.

In one embodiment, $R^3$ is —$ONO_2$ or —ONO.

In another embodiment, $R^3$ is —$OSO_3H$, —$OSO_2NH_2$, —$OSO_2NH(C_1$-$C_{10}$ alkyl), —$OSO_2N(C_1$-$C_{10}$ alkyl)$_2$ or —$OSO_2NH$-aryl.

In another embodiment, $R^3$ is —N($R^5$)$_2$.

In one embodiment, C and D are cis with respect to each other.

In another embodiment, C and D are trans with respect to each other.

The present invention also provides compositions comprising an effective amount of a Purine Derivative of Formula (III) and a physiologically acceptable carrier or vehicle.

The invention further provides Purine Derivatives of Formula (III) that are in isolated and purified form.

The invention still further provides methods for treating or preventing a Condition, comprising administering an effective amount of a Purine Derivative of Formula (III) to an animal in need thereof.

The invention further provides methods for reducing an animal's rate of metabolism, comprising administering an effective amount of a Purine Derivative of Formula (III) to an animal in need thereof.

The invention further provides methods protecting an animal's heart against myocardial damage during cardioplegia, comprising administering an effective amount of a Purine Derivative of Formula (III) to an animal in need thereof.

The Purine Derivatives of Formula (III) can exist in the form of a single enantiomer, for example, that depicted by either the Formula (III') or Formula (III"):

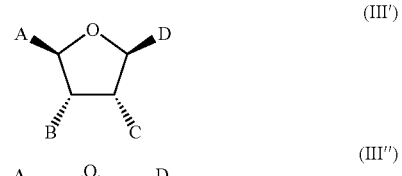

(III')

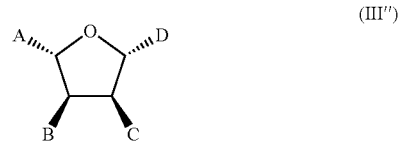

(III")

wherein A, B, C and D are defined above for the Purine Derivatives of Formula (III).

A Purine Derivative of Formula (III') is the corresponding opposite enantiomer of a Purine Derivative of Formula (III") when group A of the Purine Derivative of Formula (III") is the same as group A of the Purine Derivative of Formula (III") and when group D of the Purine Derivative of Formula (III") is the same as group D of the Purine Derivative of Formula (III").

A Purine Derivative of Formula (III") is the corresponding opposite enantiomer of a Purine Derivative of Formula (III') when group A of the Purine Derivatives of Formula (III") is the same as group A of the Purine Derivative of Formula (III') and when group D of the Purine Derivative of Formula (III") is the same as group D of the Purine Derivative of Formula (III').

In one embodiment, the Purine Derivatives of Formula (III) have the formula (III'), depicted above, wherein A, B, C and D are defined above for the Purine Derivatives of Formula (III), and wherein the Purine Derivatives of Formula (III') are substantially free of their corresponding enantiomer, represented by Formula (III").

In another embodiment, the Purine Derivatives of Formula (III) have the formula (III"), depicted above, wherein A, B, C and D are defined above for the Purine Derivatives of Formula (III), and wherein the Purine Derivatives of Formula (III") are substantially free of their corresponding enantiomer, represented by Formula (III"').

In one embodiment, the Purine Derivatives of Formula (III) exist as a mixture of a Purine Derivative of Formula (III') and a Purine Derivative of Formula (III") wherein the amount of the Purine Derivative of Formula (III') exceeds the amount of the Purine Derivative of Formula (III").

In another embodiment, the Purine Derivatives of Formula (III) exist as a mixture of a Purine Derivative of Formula (III') and a Purine Derivative of Formula (III") wherein the amount of the Purine Derivative of Formula (III") exceeds the amount of the Purine Derivative of Formula (III').

In another embodiment, the Purine Derivatives of Formula (III) exist as a racemic mixture of a Purine Derivative of Formula (III') and a Purine Derivative of Formula (III").

In another embodiment, the Purine Derivatives of Formula (III) can exist in the form of a single enantiomer, for example, that depicted by either formula (IIIa') or (IIIa"):

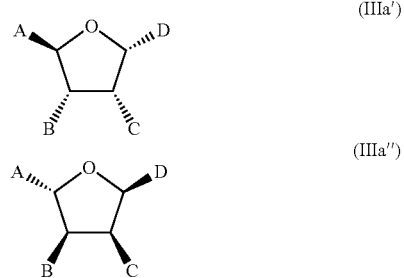

wherein A, B, C and D are defined above for the Purine Derivatives of Formula (III).

A Purine Derivative of Formula (IIIa') is the corresponding opposite enantiomer of a Purine Derivative of Formula (IIIa") when group A of the Purine Derivative of Formula (III') is the same as group A of the Purine Derivative of Formula (III") and when group D of the Purine Derivative of Formula (III') is the same as group D of the Purine Derivative of Formula (III").

A Purine Derivative of Formula (III") is the corresponding opposite enantiomer of a Purine Derivative of Formula (III') when group A of the Purine Derivative of Formula (III") is the same as group A of the Purine Derivative of Formula (III') and when group D of the Purine Derivative of Formula (III") is the same as group D of the Purine Derivative of Formula (III').

In one embodiment, the Purine Derivatives of Formula (III) have the formula (IIIa'), depicted above, wherein A, B, C and D are defined above for the Purine Derivatives of Formula (III), and wherein the Purine Derivatives of Formula (IIIa') are substantially free of their corresponding opposite enantiomer.

In another embodiment, the Purine Derivatives of Formula (III) have the formula (III"), depicted above, wherein A, B, C and D are defined above for the Purine Derivatives of Formula (III), and wherein the Purine Derivatives of Formula (III") are substantially free of their corresponding opposite enantiomer.

In another embodiment, the Purine Derivatives of Formula (III) exist as a mixture of a Purine Derivative of Formula (IIIa') and a Purine Derivative of Formula (IIIa") wherein the amount of the Purine Derivative of Formula (IIIa') exceeds the amount of the Purine Derivative of Formula (IIIa").

In a further embodiment, the Purine Derivatives of Formula (III) exist as a mixture of a Purine Derivative of Formula (IIIa') and a Purine Derivative of Formula (IIIa") wherein the amount of the Purine Derivative of Formula (IIIa") exceeds the amount of the Purine Derivative of Formula (IIIa').

In another embodiment, the Purine Derivatives of Formula (III) exist as a racemic mixture of a Purine Derivative of Formula (IIIa') and a Purine Derivative of Formula (IIIa").

A Purine Derivative of Formula (III) is the corresponding other anomer of a Purine Derivative of Formula (III') when group A of the Purine Derivative of Formula (III") is the same as group A of the Purine Derivative of Formula (III') and when group D of the Purine Derivative of Formula (III') is the same as group D of the Purine Derivative of Formula (III').

A Purine Derivative of Formula (III') is the corresponding other anomer of a Purine Derivative of Formula (III') when group A of the Purine Derivative of Formula (III') is the same as group A of the Purine Derivative of Formula (IIIa') and when group D of the Purine Derivative of Formula (III') is the same as group D of the Purine Derivative of Formula (IIa').

A Purine Derivative of Formula (IIIa") is the corresponding other anomer of a Purine Derivative of Formula (III") when group A of the Purine Derivative of Formula (IIIa") is the same as group A of the Purine Derivative of Formula (III") and when group D of the Purine Derivative of Formula (IIIa") is the same as group D of the Purine Derivative of Formula (III").

A Purine Derivative of Formula (III") is the corresponding other anomer of a Purine Derivative of Formula (IIIa") when group A of the Purine Derivative of Formula (III") is the same as group A of the Purine Derivative of Formula (IIIa") and when group D of the Purine Derivative of Formula (III") is the same as group D of the Purine Derivative of Formula (IIIa").

In one embodiment, the Purine Derivatives of Formula (III) have the formula (IIIa'), depicted above, wherein A, B, C and D are defined above for the Purine Derivatives of Formula (III), and wherein the Purine Derivatives of Formula (IIIa') are substantially free of their corresponding other anomer.

In another embodiment, the Purine Derivatives of Formula (III) have the formula (IIIa"), depicted above, wherein A, B, C and D are defined above for the Purine Derivatives of Formula (III), and wherein the Purine Derivatives of Formula (IIIa") are substantially free of their corresponding other anomer.

In one embodiment, the Purine Derivatives of Formula (III) have the formula (III'), depicted above, wherein A, B, C and D are defined above for the Purine Derivatives of Formula (III), and wherein the Purine Derivatives of Formula (III') are substantially free of their corresponding other anomer.

In another embodiment, the Purine Derivatives of Formula (III) have the formula (III"), depicted above, wherein A, B, C and D are defined above for the Purine Derivatives of Formula (III), and wherein the Purine Derivatives of Formula (III") are substantially free of their corresponding other anomer.

In one embodiment, the Purine Derivatives of Formula (III) exist as a mixture of a Purine Derivative of Formula (III') and a Purine Derivative of Formula (IIIa') wherein the amount of the Purine Derivative of Formula (III') exceeds the amount of the Purine Derivative of Formula (IIIa')

In another embodiment, the Purine Derivatives of Formula (III) exist as a mixture of a Purine Derivative of Formula (III') and a Purine Derivative of Formula (IIIa') wherein the amount of the Purine Derivative of Formula (IIIa') exceeds the amount of the Purine Derivative of Formula (III').

In another embodiment, the Purine Derivatives of Formula (IIIa) exist as a equal mixture of a Purine Derivative of Formula (III') and a Purine Derivative of Formula (IIIa').

In one embodiment, the Purine Derivatives of Formula (IIIa) exist as a mixture of a Purine Derivative of Formula (III") and a Purine Derivative of Formula (IIIa") wherein the amount of the Purine Derivative of Formula (III") exceeds the amount of the Purine Derivative of Formula (III").

In another embodiment, the Purine Derivatives of Formula (IIIa) exist as a mixture of a Purine Derivative of Formula (III") and a Purine Derivative of Formula (IIIa") wherein the amount of the Purine Derivative of Formula (IIIa") exceeds the amount of the Purine Derivative of Formula (III").

In another embodiment, the Purine Derivatives of Formula (IIIa) exist as a equal mixture of a Purine Derivative of Formula (III") and a Purine Derivative of Formula (III").

A first subclass of the Purine Derivatives of Formula (III) is that wherein one occurrence of $R^1$ is —H.

A second subclass of the Purine Derivatives of Formula (III) is that wherein one occurrence of $R^1$ is —H and the other occurrence of $R^1$ is —$C_3$-$C_8$ monocyclic cycloalkyl.

A third subclass of the Purine Derivatives of Formula (IE) is that wherein $R^2$ is —NH—N=C($R^5$)$R^6$.

A fourth subclass of the Purine Derivatives of Formula (III) is that wherein $R^3$ is —$ONO_2$.

5.2.11 The Purine Derivatives of Formula (IV)

As stated above, the present invention encompasses Purine Derivatives having the Formula (IV):

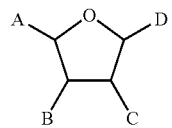

(IV)

wherein A, B, C and D are defined above for the Purine Derivatives of Formula (IV), and A and B are trans with respect to each other; B and C are cis with respect to each other; and C and D are cis or trans with respect to each other.

In one embodiment, $R^1$ is —$C_3$-$C_8$ monocyclic cycloalkyl.
In another embodiment, $R^1$ is —$C_3$-$C_8$ monocyclic cycloalkenyl.
In a specific embodiment, $R^1$ is cyclopentyl.
In one embodiment, $R^2$ is —H.
In another embodiment, $R^2$ is -halo.
In a specific embodiment, $R^2$ is —Cl.
In another embodiment, $R^2$ is —CN.
In another embodiment, $R^2$ is —N($R^3$)$_2$, —$OR^3$ or —$SR^3$.
In another embodiment, $R^2$ is —NHNHC(O)$R^3$, —NHNHC(O)O$R^3$ or —NHNHC(O)NH$R^3$. In yet another embodiment, $R^2$ is —NH—N=C($R^4$)$R^5$.
In a specific embodiment, $R^2$ is —NH—N=CH-cyclopropyl.
In one embodiment, C and D are cis with respect to each other.
In another embodiment, C and D are trans with respect to each other.

The present invention also provides compositions comprising an effective amount of a Purine Derivative of Formula (IV) and a physiologically acceptable carrier or vehicle.

The invention further provides Purine Derivatives of Formula (IV) that are in isolated and purified form.

The invention still further provides methods for treating or preventing a Condition, comprising administering an effective amount of a Purine Derivative of Formula (IV) to an animal in need thereof.

The invention further provides methods for reducing an animal's rate of metabolism, comprising administering an effective amount of a Purine Derivative of Formula (IV) to an animal in need thereof.

The invention further provides methods protecting an animal's heart against myocardial damage during cardioplegia, comprising administering an effective amount of a Purine Derivative of Formula (IV) to an animal in need thereof.

The Purine Derivatives of Formula (IV) can exist in the form of a single enantiomer, for example, that depicted by either the Formula (IV') or Formula (IV"):

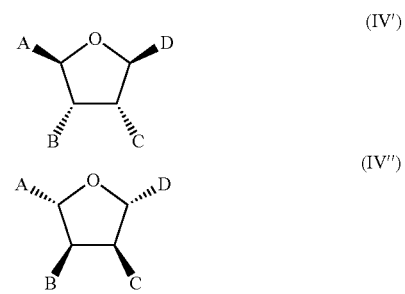

wherein A, B, C and D are defined above for the Purine Derivatives of Formula (IV).

A Purine Derivative of Formula (IV') is the corresponding opposite enantiomer of a Purine Derivative of Formula (IV") when group A of the Purine Derivative of Formula (IV') is the same as group A of the Purine Derivative of Formula (IV") and when group D of the Purine Derivative of Formula (IV') is the same as group D of the Purine Derivative of Formula (IV").

A Purine Derivative of Formula (IV") is the corresponding opposite enantiomer of a Purine Derivative of Formula (IV') when group A of the Purine Derivatives of Formula (IV") is the same as group A of the Purine Derivative of Formula (IV') and when group D of the Purine Derivative of Formula (IV") is the same as group D of the Purine Derivative of Formula (IV').

In one embodiment, the Purine Derivatives of Formula (IV) have the formula (IV'), depicted above, wherein A, B, C and D are defined above for the Purine Derivatives of Formula (IV), and wherein the Purine Derivatives of Formula (IV') are substantially free of their corresponding enantiomer, represented by Formula (IV").

In another embodiment, the Purine Derivatives of Formula (IV) have the formula (IV"), depicted above, wherein A, B, C and D are defined above for the Purine Derivatives of Formula (IV), and wherein the Purine Derivatives of Formula (IV") are substantially free of their corresponding enantiomer, represented by Formula (IV').

In one embodiment, the Purine Derivatives of Formula (IV) exist as a mixture of a Purine Derivative of Formula (IV') and a Purine Derivative of Formula (IV") wherein the amount of the Purine Derivative of Formula (IV') exceeds the amount of the Purine Derivative of Formula (IV").

In another embodiment, the Purine Derivatives of Formula (IV) exist as a mixture of a Purine Derivative of Formula (IV')

and a Purine Derivative of Formula (IV''') wherein the amount of the Purine Derivative of Formula (IV''') exceeds the amount of the Purine Derivative of Formula (IV').

In another embodiment, the Purine Derivatives of Formula (IV) exist as a racemic mixture of a Purine Derivative of Formula (IV') and a Purine Derivative of Formula (IV''')

In another embodiment, the Purine Derivatives of Formula (IV) can exist in the form of a single enantiomer, for example, that depicted by either formula (IVa') or (IVa''):

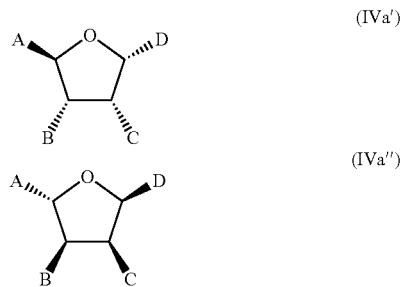

wherein A, B, C and D are defined above for the Purine Derivatives of Formula (IV).

A Purine Derivative of Formula (IVa') is the corresponding opposite enantiomer of a Purine Derivative of Formula (IVa'') when group A of the Purine Derivative of Formula (IVa') is the same as group A of the Purine Derivative of Formula (IVa'') and when group D of the Purine Derivative of Formula (IVa') is the same as group D of the Purine Derivative of Formula (IVa'').

A Purine Derivative of Formula (IVa'') is the corresponding opposite enantiomer of a Purine Derivative of Formula (IVa') when group A of the Purine Derivative of Formula (IVa'') is the same as group A of the Purine Derivative of Formula (IVa') and when group D of the Purine Derivative of Formula (IVa'') is the same as group D of the Purine Derivative of Formula (IVa').

In one embodiment, the Purine Derivatives of Formula (IV) have the formula (IVa'), depicted above, wherein A, B, C and D are defined above for the Purine Derivatives of Formula (IV), and wherein the Purine Derivatives of Formula (IVa') are substantially free of their corresponding opposite enantiomer.

In another embodiment, the Purine Derivatives of Formula (IV) have the formula (IVa''), depicted above, wherein A, B, C and D are defined above for the Purine Derivatives of Formula (IV), and wherein the Purine Derivatives of Formula (IVa'') are substantially free of their corresponding opposite enantiomer.

In another embodiment, the Purine Derivatives of Formula (IV) exist as a mixture of a Purine Derivative of Formula (IVa') and a Purine Derivative of Formula (IVa'') wherein the amount of the Purine Derivative of Formula (IVa') exceeds the amount of the Purine Derivative of Formula (IVa'').

In a further embodiment, the Purine Derivatives of Formula (IV) exist as a mixture of a Purine Derivative of Formula (IVa') and a Purine Derivative of Formula (IVa'') wherein the amount of the Purine Derivative of Formula (IVa'') exceeds the amount of the Purine Derivative of Formula (IVa').

In another embodiment, the Purine Derivatives of Formula (IV) exist as a racemic mixture of a Purine Derivative of Formula (IVa') and a Purine Derivative of Formula (IVa'').

A Purine Derivative of Formula (IVa') is the corresponding other anomer of a Purine Derivative of Formula (IV') when group A of the Purine Derivative of Formula (IVa') is the same as group A of the Purine Derivative of Formula (IV') and when group D of the Purine Derivative of Formula (IVa') is the same as group D of the Purine Derivative of Formula (IV').

A Purine Derivative of Formula (IV') is the corresponding other anomer of a Purine Derivative of Formula (IVa') when group A of the Purine Derivative of Formula (IV') is the same as group A of the Purine Derivative of Formula (IVa') and when group D of the Purine Derivative of Formula (IV') is the same as group D of the Purine Derivative of Formula (IVa').

A Purine Derivative of Formula (IVa'') is the corresponding other anomer of a Purine Derivative of Formula (IV''') when group A of the Purine Derivative of Formula (IVa'') is the same as group A of the Purine Derivative of Formula (IV''') and when group D of the Purine Derivative of Formula (IVa'') is the same as group D of the Purine Derivative of Formula (IV''').

A Purine Derivative of Formula (IV''') is the corresponding other anomer of a Purine Derivative of Formula (IVa'') when group A of the Purine Derivative of Formula (IV''') is the same as group A of the Purine Derivative of Formula (IVa'') and when group D of the Purine Derivative of Formula (IV''') is the same as group D of the Purine Derivative of Formula (IVa'').

In one embodiment, the Purine Derivatives of Formula (IV) have the formula (IVa'), depicted above, wherein A, B, C and D are defined above for the Purine Derivatives of Formula (IV), and wherein the Purine Derivatives of Formula (IVa') are substantially free of their corresponding other anomer.

In another embodiment, the Purine Derivatives of Formula (IV) have the formula (IVa''), depicted above, wherein A, B, C and D are defined above for the Purine Derivatives of Formula (IV), and wherein the Purine Derivatives of Formula (IVa'') are substantially free of their corresponding other anomer.

In one embodiment, the Purine Derivatives of Formula (IV) have the formula (IV'), depicted above, wherein A, B, C and D are defined above for the Purine Derivatives of Formula (IV), and wherein the Purine Derivatives of Formula (IV') are substantially free of their corresponding other anomer.

In another embodiment, the Purine Derivatives of Formula (IV) have the formula (IV'''), depicted above, wherein A, B, C and D are defined above for the Purine Derivatives of Formula (IV), and wherein the Purine Derivatives of Formula (IV''') are substantially free of their corresponding other anomer.

In one embodiment, the Purine Derivatives of Formula (IV) exist as a mixture of a Purine Derivative of Formula (IV') and a Purine Derivative of Formula (IVa') wherein the amount of the Purine Derivative of Formula (IV') exceeds the amount of the Purine Derivative of Formula (IVa')

In another embodiment, the Purine Derivatives of Formula (IV) exist as a mixture of a Purine Derivative of Formula (IV') and a Purine Derivative of Formula (IVa') wherein the amount of the Purine Derivative of Formula (IVa') exceeds the amount of the Purine Derivative of Formula (IV').

In another embodiment, the Purine Derivatives of Formula (IVa) exist as a equal mixture of a Purine Derivative of Formula (IV') and a Purine Derivative of Formula (IVa').

In one embodiment, the Purine Derivatives of Formula (IVa) exist as a mixture of a Purine Derivative of Formula (IV''') and a Purine Derivative of Formula (IVa'') wherein the amount of the Purine Derivative of Formula (IV''') exceeds the amount of the Purine Derivative of Formula (IVa'').

In another embodiment, the Purine Derivatives of Formula (IVa) exist as a mixture of a Purine Derivative of Formula (IV''') and a Purine Derivative of Formula (IVa'') wherein the amount of the Purine Derivative of Formula (IVa'') exceeds the amount of the Purine Derivative of Formula (IV''').

In another embodiment, the Purine Derivatives of Formula (IVa) exist as a equal mixture of a Purine Derivative of Formula (IV''') and a Purine Derivative of Formula (IVa'').

A first subclass of the Purine Derivatives of Formula (IV) is that wherein $R^1$ is -cyclopentyl.

A second subclass of the Purine Derivatives of Formula (IV) is that wherein $R^2$ is —H.

A third subclass of the Purine Derivatives of Formula (IV) is that wherein $R^2$ is —Cl.

Illustrative Purine Derivatives of Formula (IV) include the compounds listed below:

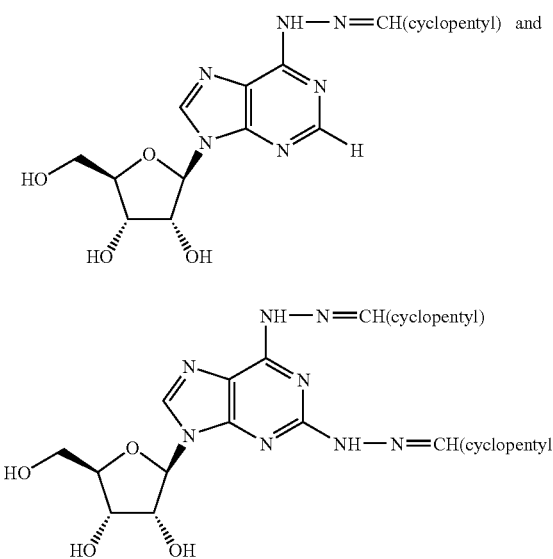

and pharmaceutically acceptable salts thereof.

5.2.12 The Purine Derivatives of Formula (V)

As stated above, the present invention encompasses Purine Derivatives having the Formula (V):

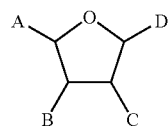

(V)

wherein A, B, C and D are defined above for the Purine Derivatives of Formula (V), and A and B are trans with respect to each other; B and C are cis with respect to each other; and C and D are cis or trans with respect to each other.

In one embodiment, $R^1$ is —$C_1$-$C_{10}$ alkyl.

In another embodiment, $R^1$ is —$(CH_2)_m$-(3- to 7-membered monocyclic heterocycle) or —$(CH_2)_m$-(8- to 12-membered bicyclic heterocycle).

In another embodiment, $R^1$ is —$(CH_2)_m$—($C_8$-$C_{12}$ bicyclic cycloalkyl) or —$(CH_2)_n$—($C_8$-$C_{12}$ bicyclic cycloalkenyl).

In still another embodiment, $R^1$ is —$(CH_2)_m$—($C_3$-$C_8$ monocyclic cycloalkyl) or —$(CH_2)_n$—($C_3$-$C_8$ monocyclic cycloalkenyl).

In a further embodiment, $R^1$ is —$(CH_2)_m$-aryl.

In one embodiment, $R^{1a}$ is —$C_3$-$C_8$ monocyclic cycloalkyl.

In another embodiment, $R^{1a}$ is —$C_3$-$C_8$ monocyclic cycloalkenyl.

In a specific embodiment, $R^{1a}$ is cyclopentyl.

In another embodiment, $R^1$ and $R^{1a}$ together with the carbon atom to which they are attached form a —$C_3$-$C_8$ monocyclic cycloalkyl, a —$C_3$-$C_8$ monocyclic cycloalkenyl, a —$C_8$-$C_{12}$ bicyclic cycloalkyl, or a —$C_8$-$C_{12}$ bicyclic cycloalkenyl.

In one embodiment, $R^2$ is —$OR^4$ or —$SR^4$.

In another embodiment, $R^2$ is —NHNHC(O)$R^3$, —NHNHC(O)$OR^3$ or —NHNHC(O)NH$R^3$. In yet another embodiment, $R^2$ is —NH—N=C($R^5$)$R^6$.

In a specific embodiment, $R^2$ is —NH—N=CH-cyclopropyl.

In one embodiment, C and D are cis with respect to each other.

In another embodiment, C and D are trans with respect to each other.

The present invention also provides compositions comprising an effective amount of a Purine Derivative of Formula (V) and a physiologically acceptable carrier or vehicle.

The invention further provides Purine Derivatives of Formula (V) that are in isolated and purified form.

The invention still further provides methods for treating or preventing a Condition, comprising administering an effective amount of a Purine Derivative of Formula (V) to an animal in need thereof.

The invention further provides methods for reducing an animal's rate of metabolism, comprising administering an effective amount of a Purine Derivative of Formula (V) to an animal in need thereof.

The invention further provides methods protecting an animal's heart against myocardial damage during cardioplegia, comprising administering an effective amount of a Purine Derivative of Formula (V) to an animal in need thereof.

The Purine Derivatives of Formula (V) can exist in the form of a single enantiomer, for example, that depicted by either the Formula (V') or Formula (V''):

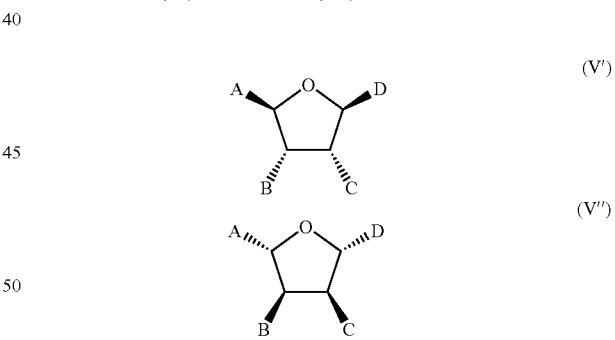

wherein A, B, C and D are defined above for the Purine Derivatives of Formula (V).

A Purine Derivative of Formula (V') is the corresponding opposite enantiomer of a Purine Derivative of Formula (V''') when group A of the Purine Derivative of Formula (V') is the same as group A of the Purine Derivative of Formula (V''') and when group D of the Purine Derivative of Formula (V') is the same as group D of the Purine Derivative of Formula (V''').

A Purine Derivative of Formula (V'') is the corresponding opposite enantiomer of a Purine Derivative of Formula (V') when group A of the Purine Derivatives of Formula (V''') is the same as group A of the Purine Derivative of Formula (V') and when group D of the Purine Derivative of Formula (V''') is the same as group D of the Purine Derivative of Formula (V').

In one embodiment, the Purine Derivatives of Formula (V) have the formula (V'), depicted above, wherein A, B, C and D are defined above for the Purine Derivatives of Formula (V), and wherein the Purine Derivatives of Formula (V') are substantially free of their corresponding enantiomer, represented by Formula (V").

In another embodiment, the Purine Derivatives of Formula (V) have the formula (V"), depicted above, wherein A, B, C and D are defined above for the Purine Derivatives of Formula (V), and wherein the Purine Derivatives of Formula (V") are substantially free of their corresponding enantiomer, represented by Formula (V').

In one embodiment, the Purine Derivatives of Formula (V) exist as a mixture of a Purine Derivative of Formula (V') and a Purine Derivative of Formula (V") wherein the amount of the Purine Derivative of Formula (V') exceeds the amount of the Purine Derivative of Formula (V").

In another embodiment, the Purine Derivatives of Formula (V) exist as a mixture of a Purine Derivative of Formula (V') and a Purine Derivative of Formula (V") wherein the amount of the Purine Derivative of Formula (V") exceeds the amount of the Purine Derivative of Formula (V').

In another embodiment, the Purine Derivatives of Formula (V) exist as a racemic mixture of a Purine Derivative of Formula (V') and a Purine Derivative of Formula (V")

In another embodiment, the Purine Derivatives of Formula (V) can exist in the form of a single enantiomer, for example, that depicted by either formula (Va') or (Va"):

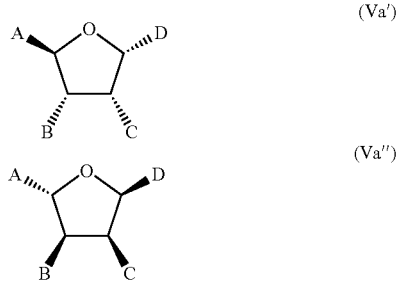

wherein A, B, C and D are defined above for the Purine Derivatives of Formula (V).

A Purine Derivative of Formula (Va') is the corresponding opposite enantiomer of a Purine Derivative of Formula (Va") when group A of the Purine Derivative of Formula (Va') is the same as group A of the Purine Derivative of Formula (Va") and when group D of the Purine Derivative of Formula (Va') is the same as group D of the Purine Derivative of Formula (Va").

A Purine Derivative of Formula (Va") is the corresponding opposite enantiomer of a Purine Derivative of Formula (Va') when group A of the Purine Derivative of Formula (Va") is the same as group A of the Purine Derivative of Formula (Va') and when group D of the Purine Derivative of Formula (Va") is the same as group D of the Purine Derivative of Formula (Va').

In one embodiment, the Purine Derivatives of Formula (V) have the formula (Va'), depicted above, wherein A, B, C and D are defined above for the Purine Derivatives of Formula (V), and wherein the Purine Derivatives of Formula (Va') are substantially free of their corresponding opposite enantiomer.

In another embodiment, the Purine Derivatives of Formula (V) have the formula (Va"), depicted above, wherein A, B, C and D are defined above for the Purine Derivatives of Formula (V), and wherein the Purine Derivatives of Formula (Va") are substantially free of their corresponding opposite enantiomer.

In another embodiment, the Purine Derivatives of Formula (V) exist as a mixture of a Purine Derivative of Formula (Va') and a Purine Derivative of Formula (Va") wherein the amount of the Purine Derivative of Formula (Va') exceeds the amount of the Purine Derivative of Formula (Va").

In a further embodiment, the Purine Derivatives of Formula (V) exist as a mixture of a Purine Derivative of Formula (Va') and a Purine Derivative of Formula (Va") wherein the amount of the Purine Derivative of Formula (Va") exceeds the amount of the Purine Derivative of Formula (Va').

In another embodiment, the Purine Derivatives of Formula (V) exist as a racemic mixture of a Purine Derivative of Formula (Va') and a Purine Derivative of Formula (Va").

A Purine Derivative of Formula (Va') is the corresponding other anomer of a Purine Derivative of Formula (V') when group A of the Purine Derivative of Formula (Va') is the same as group A of the Purine Derivative of Formula (V') and when group D of the Purine Derivative of Formula (Va') is the same as group D of the Purine Derivative of Formula (V').

A Purine Derivative of Formula (V') is the corresponding other anomer of a Purine Derivative of Formula (Va') when group A of the Purine Derivative of Formula (V') is the same as group A of the Purine Derivative of Formula (Va') and when group D of the Purine Derivative of Formula (V') is the same as group D of the Purine Derivative of Formula (Va').

A Purine Derivative of Formula (Va") is the corresponding other anomer of a Purine Derivative of Formula (V") when group A of the Purine Derivative of Formula (Va") is the same as group A of the Purine Derivative of Formula (V") and when group D of the Purine Derivative of Formula (Va") is the same as group D of the Purine Derivative of Formula (V").

A Purine Derivative of Formula (V") is the corresponding other anomer of a Purine Derivative of Formula (Va") when group A of the Purine Derivative of Formula (V") is the same as group A of the Purine Derivative of Formula (Va") and when group D of the Purine Derivative of Formula (V") is the same as group D of the Purine Derivative of Formula (Va").

In one embodiment, the Purine Derivatives of Formula (V) have the formula (Va'), depicted above, wherein A, B, C and D are defined above for the Purine Derivatives of Formula (V), and wherein the Purine Derivatives of Formula (Va') are substantially free of their corresponding other anomer.

In another embodiment, the Purine Derivatives of Formula (V) have the formula (Va"), depicted above, wherein A, B, C and D are defined above for the Purine Derivatives of Formula (V), and wherein the Purine Derivatives of Formula (Va") are substantially free of their corresponding other anomer.

In one embodiment, the Purine Derivatives of Formula (V) have the formula (V'), depicted above, wherein A, B, C and D are defined above for the Purine Derivatives of Formula (V), and wherein the Purine Derivatives of Formula (V') are substantially free of their corresponding other anomer.

In another embodiment, the Purine Derivatives of Formula (V) have the formula (V"), depicted above, wherein A, B, C and D are defined above for the Purine Derivatives of Formula (V), and wherein the Purine Derivatives of Formula (V") are substantially free of their corresponding other anomer.

In one embodiment, the Purine Derivatives of Formula (V) exist as a mixture of a Purine Derivative of Formula (V') and a Purine Derivative of Formula (Va') wherein the amount of the Purine Derivative of Formula (V') exceeds the amount of the Purine Derivative of Formula (Va')

In another embodiment, the Purine Derivatives of Formula (V) exist as a mixture of a Purine Derivative of Formula (V') and a Purine Derivative of Formula (Va') wherein the amount of the Purine Derivative of Formula (Va') exceeds the amount of the Purine Derivative of Formula (V').

In another embodiment, the Purine Derivatives of Formula (Va) exist as a equal mixture of a Purine Derivative of Formula (V') and a Purine Derivative of Formula (Va').

In one embodiment, the Purine Derivatives of Formula (Va) exist as a mixture of a Purine Derivative of Formula (V") and a Purine Derivative of Formula (Va") wherein the amount of the Purine Derivative of Formula (V") exceeds the amount of the Purine Derivative of Formula (Va").

In another embodiment, the Purine Derivatives of Formula (Va) exist as a mixture of a Purine Derivative of Formula (V") and a Purine Derivative of Formula (Va") wherein the amount of the Purine Derivative of Formula (Va") exceeds the amount of the Purine Derivative of Formula (V").

In another embodiment, the Purine Derivatives of Formula (Va) exist as a equal mixture of a Purine Derivative of Formula (V") and a Purine Derivative of Formula (Va").

5.3 Methods for Making the Purine Derivatives

The Purine Derivatives can be made according to published methods (see Cristalli et al., *J. Med. Chem.* 35:2363-2369, 1992; Cristalli et al., *J. Med. Chem.* 37:1720-1726, 1994; Cristalli et al, *J. Med. Chem.* 38:1462-1472, 1995; and Camaioni et al., *Bioorg. Med. Chem.* 5:2267-2275, 1997), or by using the synthetic procedures outlined below in Schemes 1-12.

Scheme 1 shows methods for making nucleoside intermediates that are useful for making the Purine Derivatives of Formulas (Ia), (Ib), (Ic), (Id), (Ie), (If), (Ig), (Ih), (II), (III), (IV) and (V).

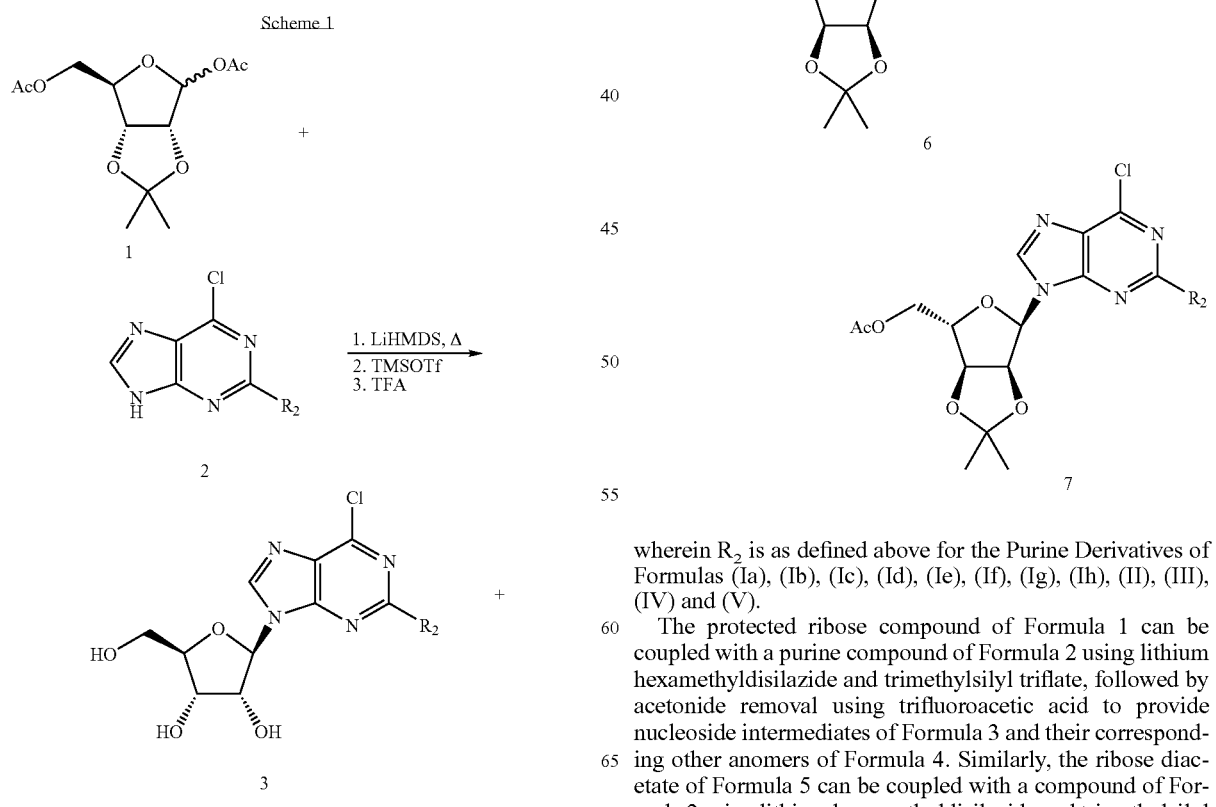

wherein $R_2$ is as defined above for the Purine Derivatives of Formulas (Ia), (Ib), (Ic), (Id), (Ie), (If), (Ig), (Ih), (II), (III), (IV) and (V).

The protected ribose compound of Formula 1 can be coupled with a purine compound of Formula 2 using lithium hexamethyldisilazide and trimethylsilyl triflate, followed by acetonide removal using trifluoroacetic acid to provide nucleoside intermediates of Formula 3 and their corresponding other anomers of Formula 4. Similarly, the ribose diacetate of Formula 5 can be coupled with a compound of Formula 2 using lithium hexamethyldisilazide and trimethylsilyl triflate to provide acetonide-protected nucleoside intermediates of Formula 6 and their corresponding other anomers of Formula 7.

Scheme 2 shows a method useful for making the adenosine intermediates of Formula 8 which are useful for making the Purine Derivatives of Formulas (Ia), (Ib), (Ic), (Id) and (Ie).

Scheme 2

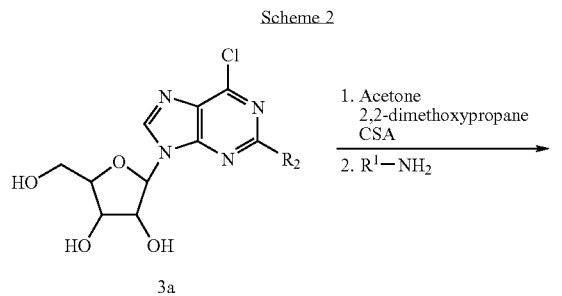

3a

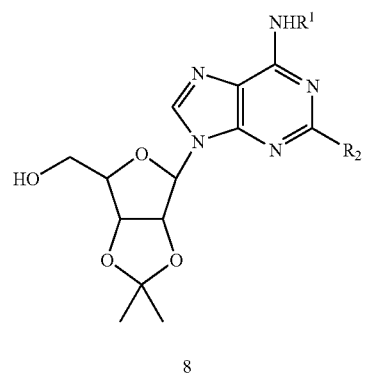

8 where $R^1$ and $R^2$ are defined above herein for the Purine Derivatives.

The 6-chloroadenosine derivative of formula 3a is converted to its 2',3'-acetonide using acetone and 2,2-dimethoxypropane in the presence of camphorsulfonic acid. The acetonide can be further derivatized using an amine of formula $R^1$—$NH_2$ in the presence of base to provide compounds of formula 8.

Scheme 3 shows a method useful for making the Purine Derivatives of Formula (Ia)

Scheme 3

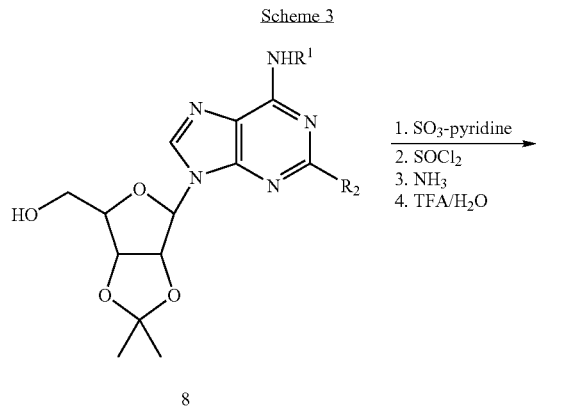

8

-continued

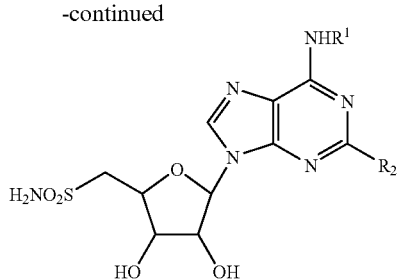

Purine Derivatives of Formula (Ia)

where $R^1$ and $R^2$ are defined above herein for the Purine Derivatives of Formula (Ia).

The adenosine intermediates of formula 8 can be converted to their 5'-sulfonic acid analogs, which can then be chlorinated using thionyl chloride to provide the corresponding 5'-chlorosulfonate intermediates. The chlorosulfonate intermediates can then be reacted with ammonia to provide the corresponding 5'-sulfonamide intermediates. Acetonide removal using TFA/water provides the Purine Derivatives of Formula (Ia).

Methodology useful for making Purine Derivatives of Formula (Ib) is described in Scheme 4.

Scheme 4

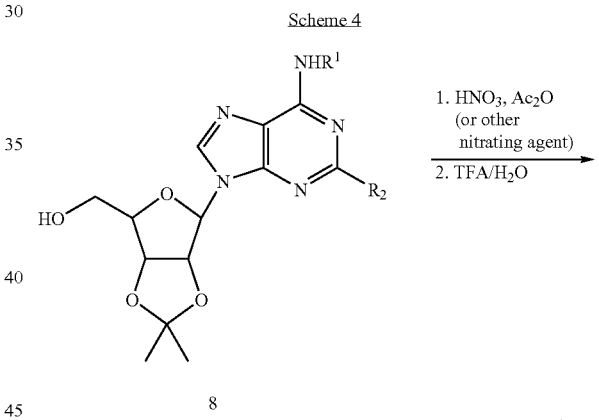

8

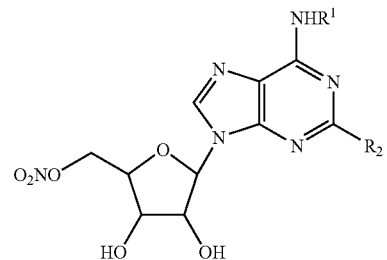

Purine Derivatives of Formula (Ib)

where $R^1$ and $R^2$ are defined above herein for the Purine Derivatives of Formula (Ib).

The Adenosine intermediates of formula 8 can be converted to their 5'-nitrate analogs using nitric acid in the presence of acetic anhydride, or other nitrating agents, such as MsCl/$ONO_3$ or nitrosonium tetrafluoroborate. Acetonide removal using TFA/water provides Purine Derivatives of Formula (Ib).

Methodology useful for making the Purine Derivatives of Formula (Ic) is outlined below in Scheme 5.

Scheme 5

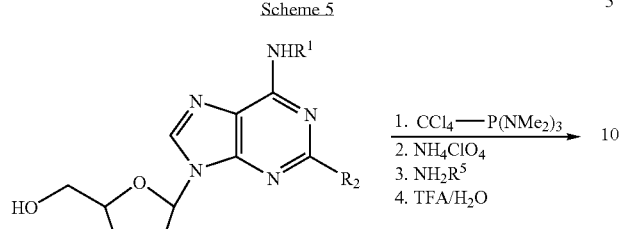

8

1. CCl₄—P(NMe₂)₃
2. NH₄ClO₄
3. NH₂R⁵
4. TFA/H₂O

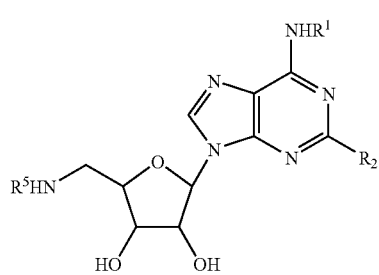

Purine Derivatives of Formula (Ic)

where $R^1$, $R^2$ and $R^5$ are defined above herein for the Purine Derivatives of Formula (Ic).

The adenosine intermediates of formula 8 can be converted to their 5'-alkoxyphosphonium perchlorate analogs using CCl₄—P(NMe₂)₃, then treating the product of this reaction with ammonium perchlorate. The intermediate 5'-alkoxyphosphonium perchlorates can subsequently be reacted with an amine of formula NH₂R⁵ to provide the 5'-amino analogs. Acetonide removal using TFA/water provides the Purine Derivatives of Formula (Ic).

Methodology useful for making the Purine Derivatives of Formula (Id) wherein $R^3$ is —CH₂OSO₃H is outlined in Scheme 6.

Scheme 6

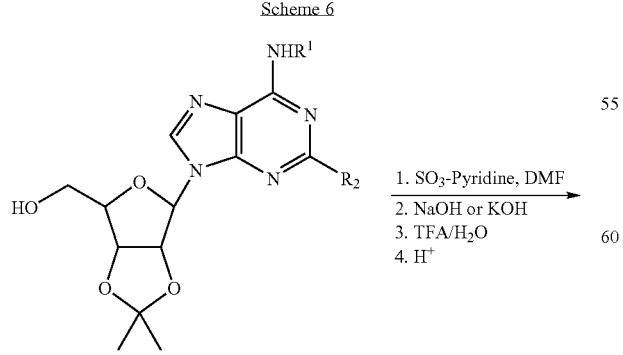

8

1. SO₃-Pyridine, DMF
2. NaOH or KOH
3. TFA/H₂O
4. H⁺

-continued

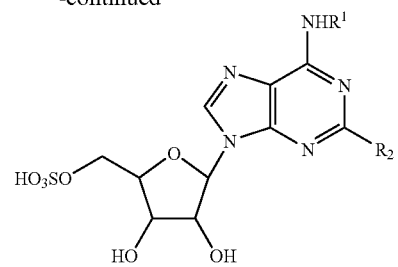

Purine Derivatives of Formula (Id)
wherein $R^3$ is —CH₂OSO₃H where $R^1$ and $R^2$ are defined above herein for the Purine Derivatives of Formula (Id).

The adenosine intermediates of formula 8 can be treated with sulfur trioxide-pyridine complex to provide the corresponding 5'-sulfonic acid pyridine salt intermediate. The pyridine salt intermediate can then be neutralized using NaOH or KOH, followed by acetonide removal using TFA/water to provide the corresponding sodium or potassium salt, respectively, of the Purine Derivatives of Formula (Id) wherein $R^3$ is —CH₂OSO₃H. Treatment of the sodium or potassium salt with strong aqueous acid, such as sulfuric or hydrochloric acid, provides the Purine Derivatives of Formula (Id) wherein $R^3$ is —CH₂OSO₃H.

Methodology useful for making the Purine Derivatives of Formula (Id) wherein $R^3$ is —ONO is outlined in Scheme 7.

Scheme 7

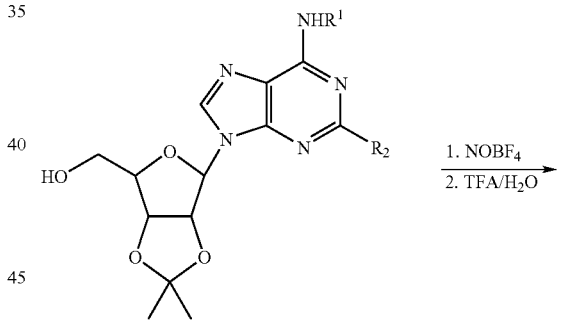

8

1. NOBF₄
2. TFA/H₂O

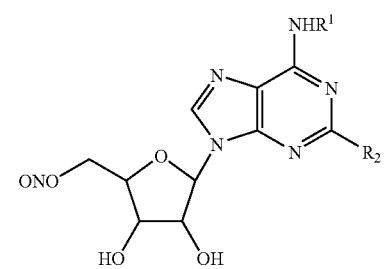

Purine Derivatives of Formula (Id)
wherein $R^3$ is —CH₂ONO where $R^1$ and $R^2$ are defined above herein for the Purine Derivatives of Formula (Id).

The adenosine intermediates of formula 8 can be treated with nitrosonium fluoroborate complex to provide the corresponding nitrosooxy intermediates. Acetonide removal using TFA/water provides the Purine Derivatives of Formula (Id) wherein $R^3$ is —$CH_2ONO$.

Methodology useful for making the Purine Derivatives of Formula (Ie) wherein $R^3$ is —$OSO_2NH(C_1\text{-}C_{10}$ alkyl), —$OSO_2N(C_1\text{-}C_{10}$ alkyl)$_2$, or —$OSO_2NH$-aryl, is outlined in Scheme 8.

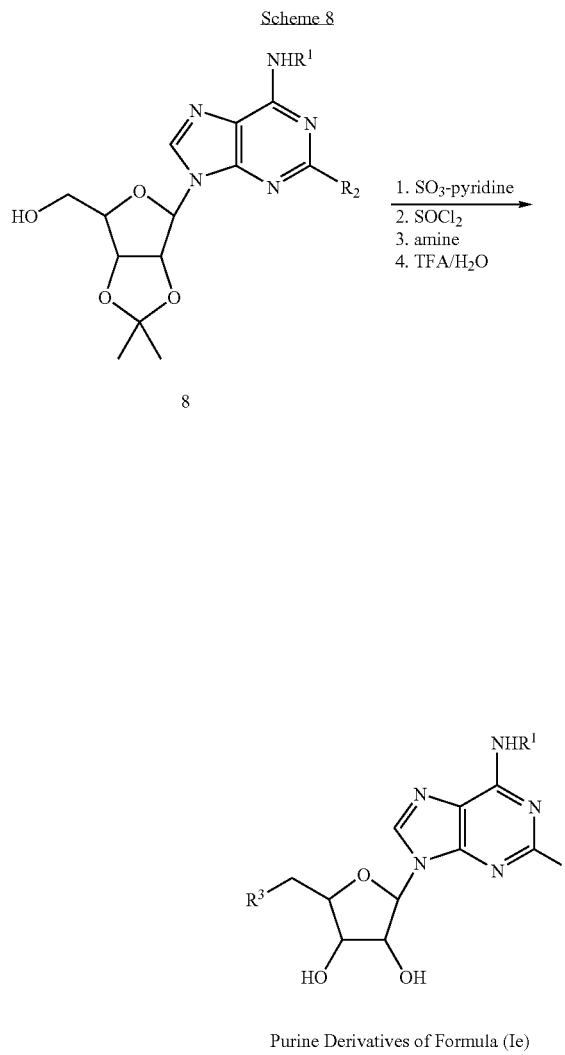

Purine Derivatives of Formula (Ie)

where $R^1$ and $R^2$ are defined above herein for the Purine Derivatives of Formula (Ie).

The adenosine intermediates of formula 8 can be reacted with sulfur trioxide-pyridine complex to provide the corresponding 5'-sulfonic acid intermediates, which can subsequently be treated with thionyl chloride to provide the intermediate 5'-chlorosulfonate intermediates. The chlorosulfonate intermediates can then be reacted with an amine of formula $H_2N$—($C_1\text{-}C_{10}$ alkyl), $HN(C_1\text{-}C_{10}$ alkyl)$_2$ or $H_2N$-aryl to provide the corresponding 5'-sulfonamide intermediates. Acetonide removal using TFA/water provides the Purine Derivatives of Formula (Ie) wherein $R^3$ is —$OSO_2NH(C_1\text{-}C_{10}$ alkyl), —$OSO_2N(C_1\text{-}C_{10}$ alkyl)$_2$, or —$OSO_2NH$-aryl.

Methodology useful for making the Purine Derivatives of Formulas (II) is outlined in Scheme 9.

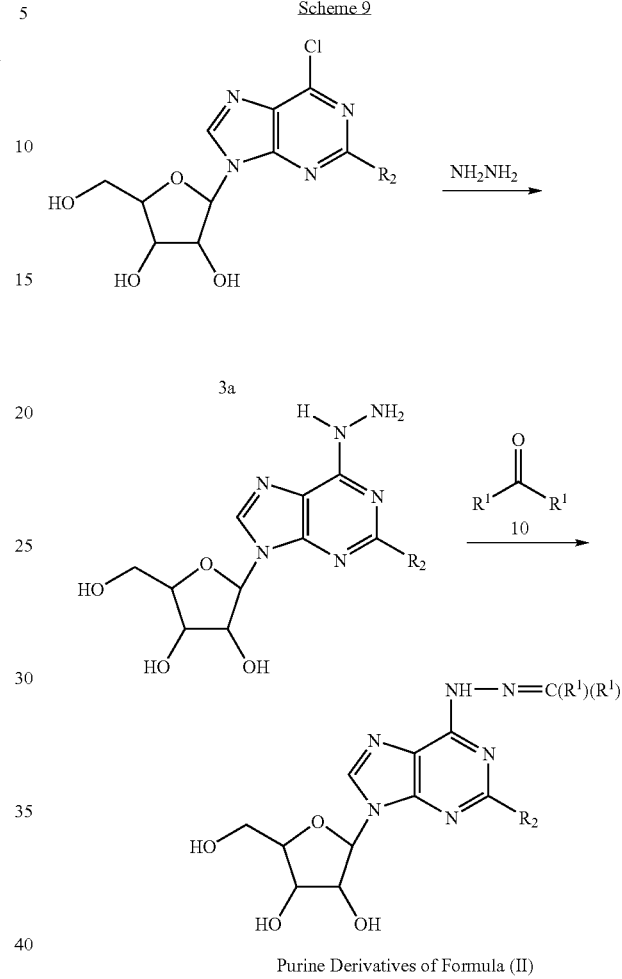

Purine Derivatives of Formula (II)

where $R^1$ and $R^2$ are defined above herein for the Purine Derivatives of Formula (II).

The 6-chloroadenosine derivatives of Formula 3a can be converted to their 6-hydrazine derivatives of Formula 9 upon reacting with hydrazine. Compounds of Formula 9 can then be treated with a carbonyl compound of formula 10 to provide the Purine Derivatives of Formula (II).

Methodology useful for making the Purine Derivatives of Formula (III) is outlined in Scheme 10.

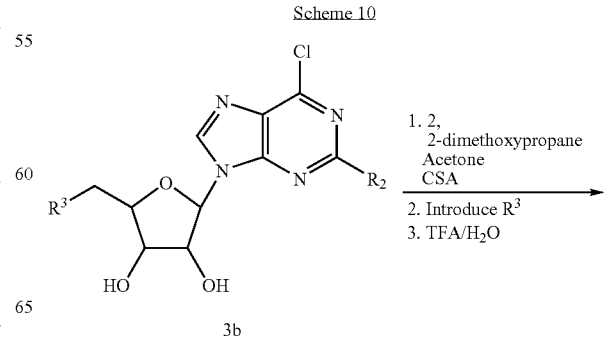

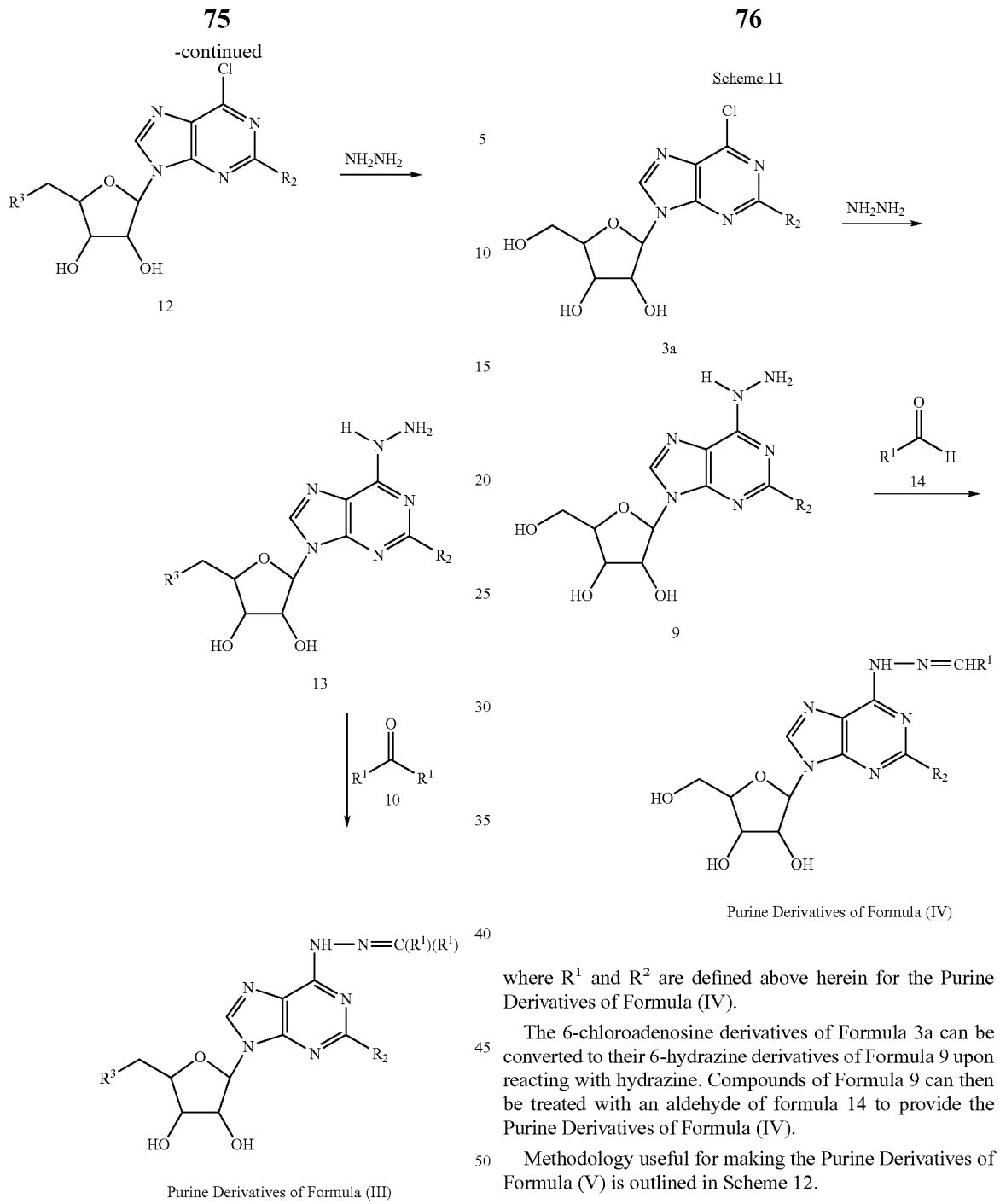

where $R^1$, $R^2$ and $R^3$ are defined above herein for the Purine Derivatives of Formula (III).

The compounds of Formula 3b can be protected as their 2',3'-acetonide derivatives and their 5'-OH group can be converted to an $R^3$ group using methodology well known to one skilled in the art of organic synthesis. Subsequent removal of the acetonide unit using TFA affords the 6-chloroadenosine compounds of formula 12 which can be converted to their 6-hydrazino derivatives of formula 13 using hydrazine. The hydrazino compounds of formula 13 can then be treated with a carbonyl compound of formula 10 to provide the Purine Derivatives of Formula (III).

Methodology useful for making the Purine Derivatives of Formula (IV) is outlined in Scheme 11.

where $R^1$ and $R^2$ are defined above herein for the Purine Derivatives of Formula (IV).

The 6-chloroadenosine derivatives of Formula 3a can be converted to their 6-hydrazine derivatives of Formula 9 upon reacting with hydrazine. Compounds of Formula 9 can then be treated with an aldehyde of formula 14 to provide the Purine Derivatives of Formula (IV).

Methodology useful for making the Purine Derivatives of Formula (V) is outlined in Scheme 12.

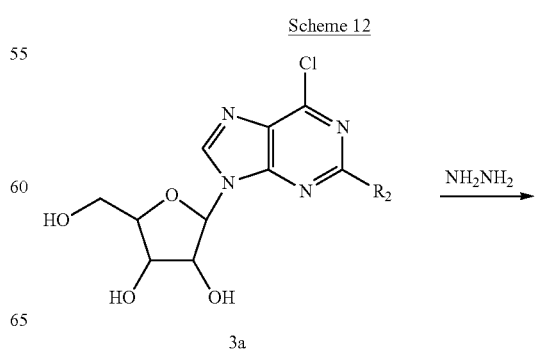

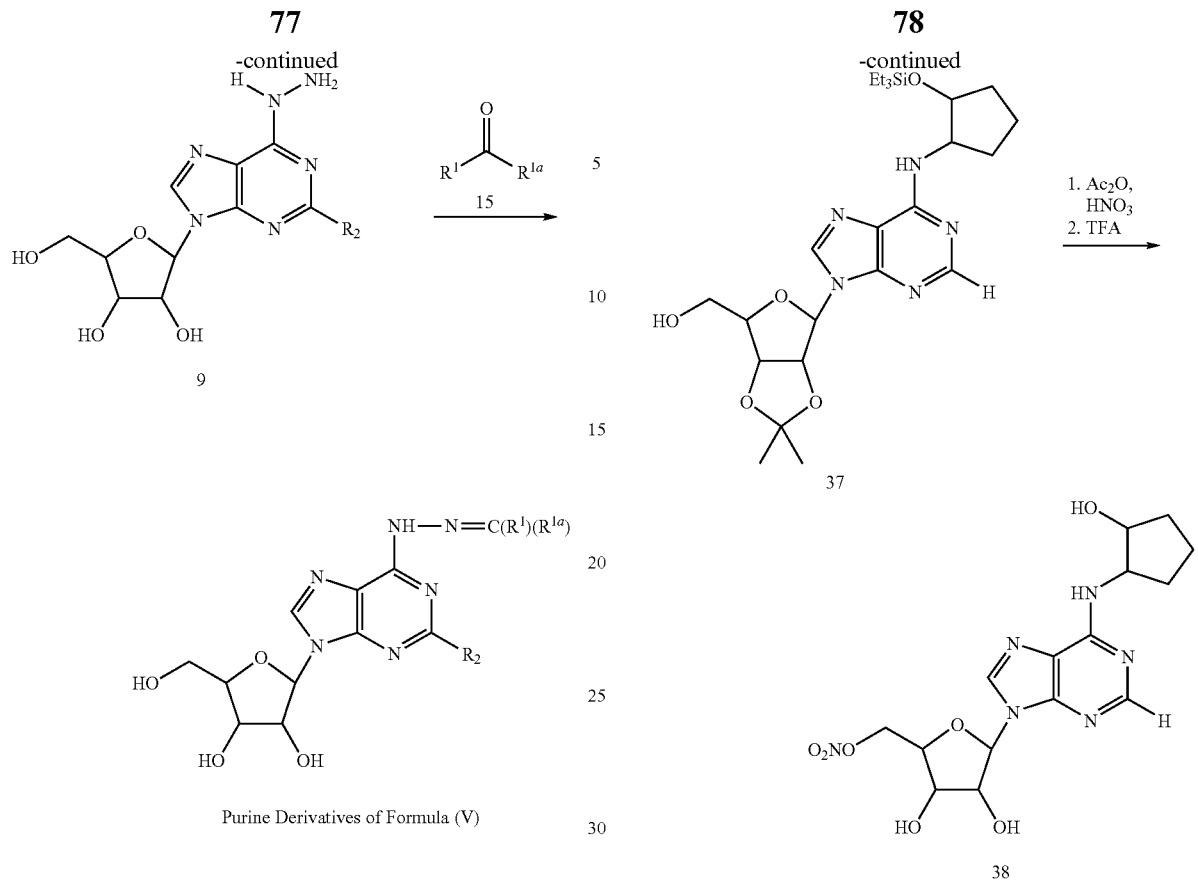

where $R^1$, $R^{1a}$ and $R^2$ are defined above herein for the Purine Derivatives of Formula (V).

The 6-chloroadenosine derivatives of Formula 3a can be converted to their 6-hydrazine derivatives of Formula 9 upon reacting with hydrazine. Compounds of Formula 9 can then be treated with a carbonyl compound of formula 15 to provide the Purine Derivatives of Formula (V).

Methodology useful for making the Purine Derivatives of Formula (Ih), wherein $R^1$ is cyclopent-1-ol-2-yl is outlined in Scheme 13.

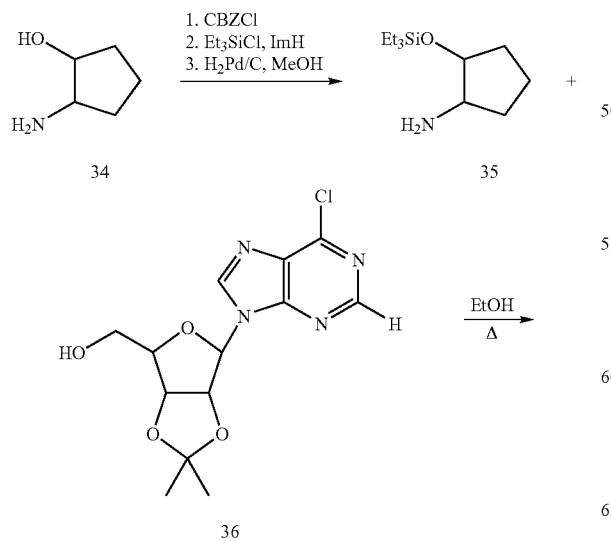

2-Aminocyclopentanol (34) is reacted with carbobenzoyloxy chloride (CBZCl) to protect the amino functionality as its carbobenzoyloxy derivative. The OH group of the carbobenzoyloxy derivative is then converted to its corresponding triethylsilyl ether using triethylsilyl chloride in the presence of imidazole. The carbobenzoyloxy protecting group is then removed via catalytic hydrogenation to provide amine compound 35. Compound 35 is coupled with compound 36 in refluxing ethanol to provide compound 37, which is subsequently nitrated using acetic anhydride/nitric acid and then reacted with trifluroacetic acid to remove the acetonide group and provide compound 38.

Methodology useful for making the Purine Derivatives of Formula (Ih), wherein $R^1$ is cyclopent-1-ol-3-yl is outlined in Scheme 14.

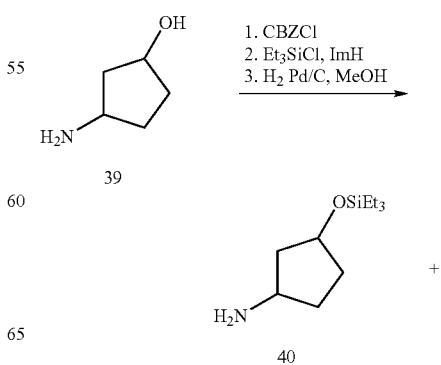

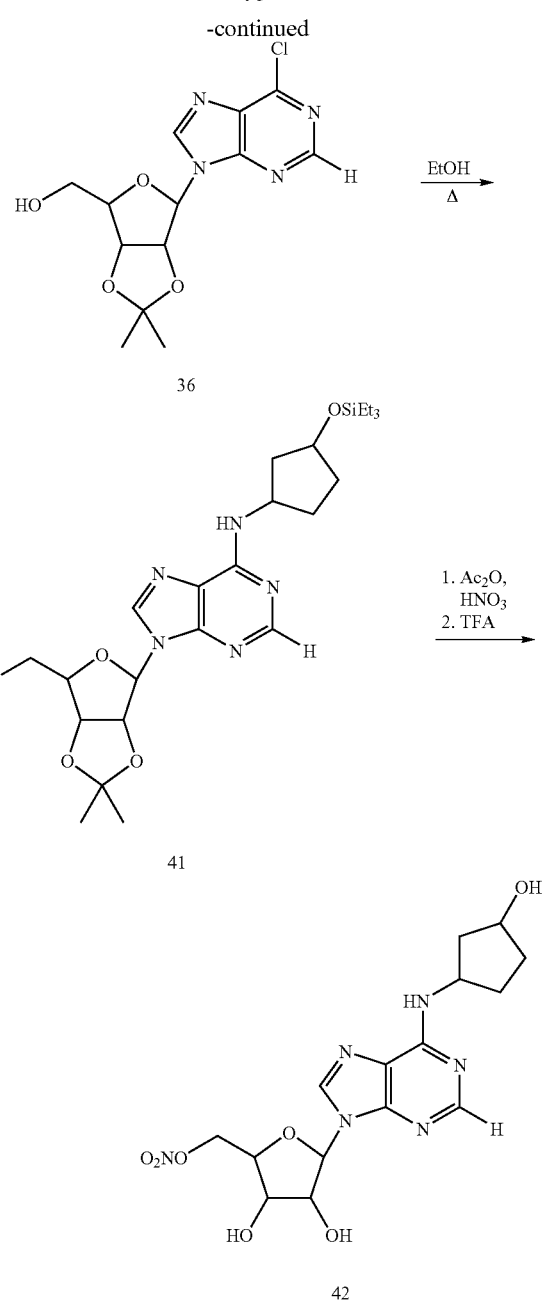

3-Aminocyclopentanol (39) is reacted with CBZCl to protect the amino functionality as its carbobenzoyloxy derivative. The OH group of the carbobenzoyloxy derivative is then converted to its corresponding triethylsilyl ether using triethylsilyl chloride in the presence of imidazole. The carbobenzoyloxy protecting group is then removed via catalytic hydrogenation to provide amine compound 40. Compound 40 is coupled with compound 36 in refluxing ethanol to provide compound 41, which is subsequently nitrated using acetic anhydride/nitric acid and then reacted with trifluoroacetic acid to remove the acetonide group and provide compound 42.

5.4 Therapeutic/Prophylactic Administration and Compositions of the Invention Due to their activity, the Purine Derivatives are advantageously useful in veterinary and human medicine. As described above, the Purine Derivatives are useful for: (i) treating or preventing a Condition in an animal in need thereof; (ii) reducing an animal's rate of metabolism; or (iii) protecting an animal's heart against myocardial damage during cardioplegia.

When administered to an animal, the Purine Derivatives can be administered as a component of a composition that comprises a physiologically acceptable carrier or vehicle. The present compositions, which comprise a Purine Derivative, can be administered orally. The Purine Derivatives can also be administered by any other convenient route, for example, by infusion or bolus injection, by absorption through epithelial or mucocutaneous linings (e.g., oral, rectal, or intestinal mucosa) and can be administered together with another biologically active agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result in the release of the Purine Derivatives into the bloodstream. The mode of administration can be left to the discretion of the practitioner.

In one embodiment, the Purine Derivatives are administered orally.

In another embodiment, the Purine Derivatives are administered intravenously.

In another embodiment, when the Purine Derivatives are used to reduce an animal's rate of metabolism, the Purine Derivatives can be administered by continuous intravenous infusion.

In other embodiments, it can be desirable to administer the Purine Derivatives locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Purine Derivatives into the central nervous system, circulatory system or gastrointestinal tract by any suitable route, including intraventricular, intrathecal injection, paraspinal injection, epidural injection, enema, and by injection adjacent to a peripheral nerve. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon or synthetic pulmonary surfactant. In certain embodiments, the Purine Derivatives can be formulated as a suppository, with traditional binders and excipients such as triglycerides.

In another embodiment the Purine Derivatives can be delivered in a vesicle, in particular a liposome (see Langer, *Science* 249:1527-1533 (1990) and Treat or prevent et al., *Liposomes in the Therapy of Infectious Disease and Cancer* 317-327 and 353-365 (1989)).

In yet another embodiment the Purine Derivatives can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment a controlled- or sustained-release system can be placed in proximity of a target of the Purine Derivatives, e.g., the spinal column, brain, colon, skin, heart, lung, or gastrointestinal tract, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to an animal. Water can be a particularly useful excipient when the Purine Derivative is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions. aerosols, sprays, suspensions, or any other form suitable for use. In one embodiment the composition is in the form of a capsule. Other examples of suitable physiologically acceptable excipients are described in *Remington's Pharmaceutical Sciences* 1447-1676 (Alfonso R. Gennaro eds., 19th ed. 1995), incorporated herein by reference.

In one embodiment the Purine Derivatives are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a Purine Derivative are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the Purine Derivatives can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. The compositions' components can be supplied either separately or mixed together in unit dosage form, for example, as a dry lyophilized powder or water-free concentrate in a hermetically sealed container such as an ampule or sachette indicating the quantity of Purine Derivative. Where the Purine Derivatives are to be administered by infusion, they can be dispensed, for example, with an infusion bottle containing sterile pharmaceutical grade water or saline. Where the Purine Derivatives are administered by injection, an ampule of sterile water for injection or saline can be provided so that the ingredients can be mixed prior to administration.

The Purine Derivatives can be administered by controlled-release or sustained-release means or by delivery devices that are well known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of a Purine Derivative to treat or prevent the Condition in a minimal amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Purine Derivative, and can thus reduce the occurrence of adverse side effects.

Controlled- or sustained-release compositions can initially release an amount of a Purine Derivative that promptly produces the desired therapeutic or prophylactic effect, and gradually and continually release other amounts of the Purine Derivative to maintain this level of therapeutic or prophylactic effect over an extended period of time. To maintain a constant level of the Purine Derivative in the body, the Purine Derivative can be released from the dosage form at a rate that will replace the amount of Purine Derivative being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Purine Derivative that is effective for treating or preventing a Condition, reducing an animal's rate of metabolism, or protecting an animal's heart against myocardial damage during cardioplegia, can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of a health-care practitioner. Suitable effective dosage amounts, however, range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner. The effective dosage amounts described herein refer to total amounts administered; that is, if more than one Purine Derivative is administered, the effective dosage amounts correspond to the total amount administered.

The amount of a Purine Derivative that is effective for treating or preventing a Condition, or protecting an animal's heart against myocardial damage during cardioplegia typically range from about 0.01 mg/kg to about 100 mg/kg of body weight per day, in one embodiment, from about 0.1 mg/kg to about 50 mg/kg body weight per day, and in another embodiment, from about 1 mg/kg to about 20 mg/kg of body weight per day.

The amount of a Purine Derivative that is effective for reducing an animal's rate of metabolism typically range from about 1 µg/kg to about 10 mg/kg, in one embodiment, from about 0.1 mg/kg to about 5 mg/kg body weight per day, and in another embodiment, from about 1 mg/kg to about 2.5 mg/kg of body weight per day.

When a Purine Derivative is a component of a solution that is useful for maintaining the viability of an organ ex vivo, the concentration of the Purine Derivative in the solution that is effective for maintaining the viability of the organ is between about 1 nM to about 1 mM.

The Purine Derivatives can be assayed in vitro or in vivo for the desired therapeutic or prophylactic activity prior to use in humans. Animal model systems can be used to demonstrate safety and efficacy.

The present methods for treating or preventing a Condition, reducing an animal's rate of metabolism, or protecting an animal's heart against myocardial damage during cardioplegia, can further comprise administering another therapeutic agent to the animal being administered a Purine Derivative. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. In one embodiment of the invention, where, another therapeutic agent is administered to an animal, the effective amount of the Purine Derivative is less than its effective amount would be where the other therapeutic agent is not administered. In this case, without being bound by theory, it is believed that the Purine Derivatives and the other therapeutic agent act synergistically.

In one embodiment the other therapeutic agent is an anti-inflammatory agent. Examples of useful anti-inflammatory agents include, but are not limited to, adrenocorticosteroids, such as cortisol, cortisone, fluorocortisone, prednisone, prednisolone, 6a-methylprednisolone, triamncinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

In another embodiment the other therapeutic agent is an anti-diabetic agent. Examples of useful anti-diabetic agents include, but are not limited to, glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformiin and phenformin; thiazolidinediones, such as pioglitazone, rosiglitazone, and troglitazone; and α-glucosidase inhibitors, such as acarbose and miglitol.

In a further embodiment the other therapeutic agent is an anti-cardiovascular-disease agent. Examples of useful anti-cardiovascular-disease agents include, but are not limited to, carnitine; thiamine; lidocaine; amiodarone; procainamide; mexiletine; bretylium tosylate; propanolol; sotalol; and muscarinic receptor antagonists, such as atropine, scopolamine, homatropine, tropicamide, pirenzipine, ipratropium, tiotropium, and tolterodine.

In another embodiment the other therapeutic agent is an analgesic agent. Examples of useful analgesic agents include, but are not limited to, buprenorphine, meperidine, morphine, codeine, propoyxphene, fentanyl, sufentanil, etorphine hydrochloride, hydrocodone, hydromorphone, nalbuphine, butorphanol, oxycodone, aspirin, ibuprofen, naproxen sodium, acetaminophen, xylazine, metedomidine, carprofen, naprosin, and pentazocine.

In a specific embodiment, the other therapeutic agent is buprenorphine.

In another embodiment, the other therapeutic agent is an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclirine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, or mixtures thereof.

A Purine Derivative and the other therapeutic agent can act additively or, in one embodiment, synergistically. In one embodiment, a Purine Derivative is administered concurrently with another therapeutic agent. In one embodiment, a composition comprising an effective amount of a Purine Derivative and an effective amount of another therapeutic agent can be administered. Alternatively, a composition comprising an effective amount of a Purine Derivative and a different composition comprising an effective amount of another therapeutic agent can be concurrently administered. In another embodiment, an effective amount of a Purine Derivative is administered prior or subsequent to administration of an effective amount of another therapeutic agent. In this embodiment, the Purine Derivative is administered while the other therapeutic agent exerts its therapeutic effect, or the other therapeutic agent is administered while the Purine Derivative exerts its preventative or therapeutic effect for treating or preventing a Condition, reducing an animal's rate of metabolism or protecting an animal's heart against myocardial damage during cardioplegia.

A composition of the invention can be prepared using a method comprising admixing a Purine Derivative and a physiologically acceptable carrier or excipient. Admixing can be accomplished using methods well known for admixing a compound (or salt) and a physiologically acceptable carrier or excipient.

5.6 Therapeutic or Prophylactic Uses of the Purine Derivatives

5.6.1 Treatment or Prevention of a Cardiovascular Disease

A cardiovascular disease can be treated or prevented by administration of an effective amount of a Purine Derivative.

Cardiovascular diseases that can be treated or prevented by administering an effective amount of a Purine Derivative include, but are not limited to, atherosclerosis, congestive heart failure, circulatory shock, cardiomyopathy, cardiac transplant, cardioplegia, and a cardiac arrhythmia.

In one embodiment, the cardiovascular disease is a cardiac arrhythmia, congestive heart failure, circulatory shock or cardiomyopathy.

In one embodiment, the cardiac arrhythmia is a tachycardia or an idiotopic arrhythmia.

In another embodiment, the methods for treating a cardiovascular disease are useful for converting a cardiac arrhythmia to a normal sinus rhythm.

In still another embodiment, the tachycardia is atrial fibrillation, supraventricular tachycardia, atrial flutter, paroxysmal supraventricular tachycardia, paroxysmal atrial tachycardia, sinus tachycardia, atrioventricular nodal reentry tachycardia, or tachycardia caused by Wolff-Parkinson-White Syndrome.

In a further embodiment, the methods for treating a tachycardia are useful for lowering the animal's ventricular rate to a rate of not less than about 40 beats per minute. In a specific embodiment, the methods are useful for lowering an animal's ventricular rate to a rate of from about 60 beats per minute to about 100 beats per minute.

5.6.2 Protecting an Animal's Heart Against Myocardial Damage During Cardioplegia In one embodiment, the invention provides methods for inducing cardioplegia comprising administering to an animal in need thereof an effective amount of a cardioplegia-inducing agent and a Purine Derivative. Cardioplegia-inducing agents useful in the present invention include, but are not limited to, potassium chloride, procaine, lidocaine, novocaine, bupivocaine, nicorandil, pinacidil, halothane, St. Thomas solution, Fremes solution, 2,3-butanedione monoxime, and esmolol.

In one embodiment, the cardioplegia-inducing agent is lidocaine.

In one embodiment, a cardioplegia-inducing agent and a Purine Derivative are present within the same composition. The present methods for inducing cardioplegia are useful for preventing or minimizing myocardial damage from occurring during cardioplegia.

In still another embodiment, the invention provides methods for protecting an animal's heart against myocardial damage during cardioplegia, the method comprising administering to an animal in need thereof an effective amount of:

(a) a cardioplegia-inducing agent; and
(b) a Purine Derivative.

In one embodiment, the cardioplegia-inducing agent is administered prior to the administration of the Purine Derivative.

In another embodiment, Purine Derivative is administered prior to the administration of the cardioplegia-inducing agent.

In a further embodiment, the cardioplegia-inducing agent and the Purine Derivative are administered concurrently.

In another embodiment, the cardioplegia-inducing agent and the Purine Derivative are administered such that the Purine Derivative exerts its prophylactic effect of protection against myocardial damage while the cardioplegia-inducing agent exerts its cardioplegic effect.

5.63 Treatment or Prevention of a Neurological Disorder

A neurological disorder can be treated or prevented by administration of an effective amount of a Purine Derivative.

Neurological disorders that can be treated or prevented by administering an effective amount of a Purine Derivative include, but are not limited to, a seizure disorder, such as epilepsy; pain, including acute postoperative pain, cancer pain, neuropathic pain, pain resulting from surgery, labor pain during childbirth, a psychogenic pain syndrome, and headache, including migraine headache and cluster headache; delirium and dementia, such as Lewy body dementia, Alzheimer's disease, Pick's disease, or a Creutzfeldt-Jakob disease; a sleep disorder, such as insomnia, hypersomnia, a sleep apnea syndrome, restless-leg syndrome, or a parasomnia; a cranial nerve disorder, such as Bell's palsy; a disorder of movement, such as tremor, dystonia, Tourette's Syndrome, myoclonus, Huntington's disease, cortico basal degeneration, chorea, a drug-induced movement disorder, progressive supranuclear palsy, Parkinson's disease, or a Parkinsonian Syndrome, such as multiple system atrophy, Wilson's disease or multi-infarct state; a demyelinating disease, such as multiple sclerosis or amyotrophic lateral sclerosis; a neuro-muscular disease, such as muscular dystrophy; a cerebrovascular disease, such as stroke; a neuroopthalmic disorder; and a psychiatric disorder, including but not limited to, somatoform disorders, such as hypochondriasis or body dysmorphic disorder; dissociation disorders, such as panic disorder, phobic disorders, or obsessive-compulsive disorders; mood disorders, such as depression or bipolar-disorders; personality disorders; psychosexual disorders; suicidal behavior; schizophrenia; brief psychotic disorder; and delusional disorder.

In one embodiment, the neurological disorder treated or prevented is epilepsy, pain, or stroke.

In one embodiment, the methods for treating pain further comprise the administration of an additional analgesic agent. In a specific embodiment, the additional analgesic agent is buprenorphine.

5.6.4 Treatment or Prevention of an Ischemic Condition

An ischemic condition can be treated or prevented by administration of an effective amount of a Purine Derivative.

Ischemic conditions that can be treated or prevented by administering an effective amount of a Purine Derivative include, but are not limited to, stable angina, unstable angina, myocardial ischemia, hepatic ischemia, mesenteric artery ischemia, intestinal ischemia, myocardial infarction, critical limb ischemia, chronic critical limb ischemia, erebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

5.6.5 Treatment or Prevention of a Reperfusion Injury

A reperfusion injury can be treated or prevented by administration of an effective amount of a Purine Derivative. Reperfusion injury can result following a naturally occurring episode, such as a myocardial infarction or stroke, or during a surgical procedure where blood flow in vessels is intentionally or unintentionally blocked.

Reperfusion injuries that can be treated or prevented by administering an effective amount of a Purine Derivative include, but are not limited to, intestinal reperfusion injury, myocardial reperfusion injury; and reperfusion injury resulting from cardiopulmonary bypass surgery, thoracoabrominal aneurysm repair surgery, carotid endaretectomy surgery, or hemorrhagic shock.

In one embodiment, the reperfusion injury results from cardiopulmonary bypass surgery, thoracoabrominal aneurysm repair surgery, carotid endarerectomy surgery or hemorrhagic shock.

5.6.6 Treatment or Prevention of Diabetes

Diabetes can be treated or prevented by administration of an effective amount of a Purine Derivative.

Types of diabetes that can be treated or prevented by administering an effective amount of a Purine Derivative include, but are not limited to, Type I diabetes (Insulin Dependent Diabetes Mellitus), Type II diabetes (Non-Insulin Dependent Diabetes Mellitus), gestational diabetes, insulinopathy, diabetes due to pancreatic disease, diabetes associated with another endocrine disease (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins.

In one embodiment, the diabetes is Type I diabetes mellitus.

In another embodiment, the diabetes is Type II diabetes mellitus.

5.6.7 Methods for Reducing an Animal's Rate of Metabolism

In one embodiment, the invention provides methods for reducing an animal's rate of metabolism comprising administering to an animal in need thereof an amount of a Purine Derivative that is effective to slow the animal's rate of metabolism.

Reducing an animal's rate of metabolism is useful for slowing an animal's heart rate during heart surgery; protecting an animal's tissue from damage during surgery, particular heart or brain surgery; reducing intracranial hypertension caused by brain injury in an animal; or inducing hibernation in an animal.

Accordingly, the present invention encompasses methods for slowing an animal's heart rate during heart surgery; protecting an animal's tissue from damage during surgery, particular heart or brain surgery; reducing intracranial hypertension caused by brain injury in an animal; or inducing hibernation in an animal, the methods comprising administering an effective amount of a Purine Derivative to an animal in need thereof.

Reducing an animal's rate of metabolism is also useful for reducing an animal's rate of oxygen consumption. Accordingly, the present invention provides methods for reducing the rate of an animal's oxygen consumption, the method comprising administering to an animal in need thereof an amount of a Purine Derivative that is effective to reduce the animal's rate of oxygen consumption. An animal's oxygen supply might be compromised due to: (i) a medical procedure, such as heart surgery, brain surgery, organ transplantation, mechanical occlusion of the vascular supply, or vascular stenosis; (ii) a disorder or medical condition such as ischemia, a respiratory disorder, respiratory failure, a pulmonary disorder, anemia, anaphylactic shock, hemmorhagic shock, dehydration, compartment syndrome, intravascular thrombus, septic shock, cystic fibrosis, lung cancer, stroke, a burn, or internal bleeding; (iii) an injury such as drowning, a crush injury to one or more limbs, choking, or suffocation; (iv) a compromised airway due to asthma, a tumor, a lung injury or a tracheal injury; (v) an external compression of one or more blood vessels; or (vi) an intrinsic obstruction of one or more blood vessels. Reducing an animal's rate of oxygen consumption is useful for treating or preventing tissue damage or stroke, resulting from an inadequate supply of oxygen to a cell, a tissue, an organ or an organ system.

In one embodiment, an animal's rate of oxygen consumption is reduced to increase emergency recitation in an injured animal.

In another embodiment, an animal's rate of oxygen consumption is reduced prior to and during heart surgery. In a specific embodiment, the animal is a human child undergoing pediatric heart surgery.

In another embodiment, a animal's rate of oxygen consumption is reduced to treat respiratory failure in an animal.

In one embodiment, an animal's rate of oxygen consumption is reduced to aid tissue metabolism in an animal whose respiration and ventilation is facilitated by a ventilator. In a specific embodiment, the animal whose respiration and ventilation is facilitated by a ventilator is a geriatric human. In another specific embodiment, the animal whose respiration and ventilation is facilitated by a ventilator is a premature human infant.

In one embodiment, an organ can be stored ex vivo in a composition comprising an effective amount of a Purine Derivative. The composition is useful for preserving an organ's viability after being removed from a donor and before the organ is transplanted in a recipient. In one embodiment, the donor and recipient are the same.

In another embodiment, an effective amount of a Purine Derivative can be administered to an animal awaiting organ transplantation to reduce the animal's rate of oxygen consumption prior to or during organ transplantation.

Reducing an animal's rate of metabolism is also useful for reducing an animal's core body temperature. Accordingly, the present invention provides methods for reducing an animal's core body temperature, the method comprising administering to an animal in need thereof an amount of a Purine Derivative that is effective to reduce the animal's core body temperature.

In one embodiment, the animal's core body temperature is reduced to a temperature from about 4° C. to about 34° C. In certain embodiments, the animal's core body temperature is reduced to about 34° C., to about 30° C., to about 25° C., to about 20° C., to about 15° C., to about 10° C., or to about 4° C.

In a specific embodiment, an animal's core body temperature is reduced to induce therapeutic hypothermia.

5.6.8 Treatment or Prevention of Obesity

Obesity can be treated or prevented by administration of an effective amount of a Purine Derivative.

Types of obesity that can be treated or prevented by administering an effective amount of a Purine Derivative include, but are not limited to, android obesity, gynoid obesity, abdominal obesity, age-related obesity, diet-induced obesity, fat-induced obesity, hypothalamic obesity, morbid obesity, multigenic obesity, and visceral obesity.

In one embodiment, the obesity is android obesity.

5.6.9 Treatment or Prevention of a Wasting Disease

In one embodiment, the invention provides methods for treating or preventing a wasting disease, comprising administering to an animal in need thereof an amount of a a Purine Derivative that is effective to treat or prevent the wasting disease.

Types of wasting diseases that can be treated or prevented by administering an effective amount of a Purine Derivative include, but are not limited to chronic wasting disease, cancer wasting syndrome, and AIDS wasting syndrome.

6. EXAMPLES

Materials: [³H]NECA was obtained from Du Pont NEN, Dreieich, Germany. Other unlabeled adenosine receptor agonists and antogonists can be obtained from RBI, Natick, Mass. The 96-well microplate filtration system (MultiScreen MAFC) was obtained from Millipore, Eschbom, Germany. Penicillin (100 U/mL), streptomycin (100 μg/mL), L-glutamine and G418 were obtained from Gibco-Life Technologies, Eggenstein, Germany. Other materials can be obtained as described in Klotz et al., *J. Biol. Chem.*, 260: 14659-14664, 1985; Lohse et al., *Naunyn-Schmiedeberg's Arch. Pharmacol.*, 336:204-210, 1987; and Klotz et al., *Naunyn-Schmiedeberg's Arch. Pharmacol.*, 357:1-9, 1998.

General Methods Proton nuclear magnetic resonance (NMR) spectra were obtained from Varian 300 MHz spectrophotometer and chemical shifts are reported in parts per million. Compounds were characterized on the basis of NMR and Mass spectral (MS) data. 6-Chloroadenosine and 2',3',5'-triacetoxy-2,6-dichloroadenosine were purchased from TRC, Ontario, Canada. 2',3'-Isopropylideneadenosine and 2-chloroadenosine were purchased from ACROS Organic, USA.

6.1 Example 1

Synthesis of Compound 16

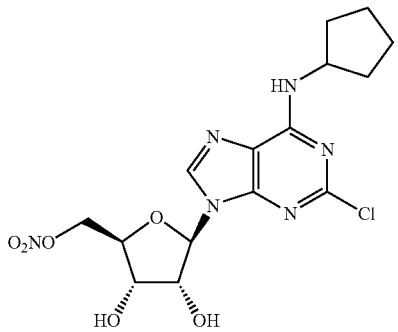

2-Chloro-$N^6$-cyclopentyladenosine-2',3',5'-triacetoxy-2,6-dichloroadenosine (1.5 g) and cyclopentylamine (8 eq.) were diluted with ethanol (50 eq.) and the resulting solution was heated at reflux for about 15 hours, then cooled to room temperature and concentrated in vacuo to provide a crude residue which was diluted with a mixture of ethyl acetate and water and transferred to a separatory funnel. The organic layer was separated, dried over sodium sulfate and concentrated in vacuo to provide a crude residue which was purified using flash column chromatography on silica gel (8% MeOH—dichloromethane as eluent) to provide 2-chloro-$N^6$-cyclopentyladenosine (0.948 g). MS m/z 370.32 [M+H]$^+$.

2',3'-Isopropylidene-2-chloro-$N^6$-cyclopentyladenosine: 2-chloro-$N^6$-cyclopentyladenosine (900 mg, as prepared in the previous step) and 2,2-dimethoxypropane (10 eq.) were diluted with acetone (15 mL) and to the resulting solution was added D-camphorsulphonic acid (1 eq) and the resulting reaction was allowed to stir at room temperature for 2 hr. The resulting reaction mixture was concentrated in vacuo, diluted with a mixture of saturated aqueous NaHCO$_3$ and ethyl acetate, and transferred to a separatory funnel. The organic layer was separated, dried over sodium sulfate and concentrated in vacuo to provide a crude residue which was purified using flash column chromatography on silica gel (using 5% MeOH—dichloromethane as eluent) to provide 2',3'-Isopropylidene-2-chloro-$N^6$-cyclopentyladenosine (0.905 g). $^1$H NMR (CDCl$_3$, 300 MHz): δ 1.36 (s, 3H), 1.62 (s, 3H), 1.66-2.16 (m, 9H), 3.78 (d, J=12.9 Hz, 1H), 3.98 (d, J=12.9 Hz, 1H), 4.51 (bs, 1H), 4.55-4.60 (m, 1H), 5.09-5.17 (m, 2H), 5.81 (bs, 1H), 7.25 (s, 1H), 7.89 (s, 1H).

2',3'-Isopropylidene-2-chloro-$N^6$-cyclopentyladenosine-5'-nitrate: A solution of nitric acid (2.0 mL, 60%) was added slowly over a period of 30 minutes to acetic anhydride (16.0 mL) at −10 to 10° C. (using acetonitrile-CO$_2$ cooling bath) and the reaction mixture was allowed to stir at −10 to 10° C. for 10 minutes. The reaction mixture was then cooled to −30° C. and then a solution of 2',3'-Isopropylidene-2-chloro-$N^6$-cyclopentyladenosine (655 mg, 0.0016 mol, as prepared in the previous step) in acetic anhydride (8.0 mL) was added slowly. When addition was complete, the resulting reaction was allowed to warm to −5° C. and monitored using TLC (solvent 5% MeOH—CH$_2$Cl$_2$ or 70% EtOAc-hexane). When the reaction was complete, the reaction mixture was poured slowly into an ice cold mixture of saturated aqueous NaHCO₃ (300 equivalent in 75 mL water) and ethyl acetate (60 mL). The organic layer was separated and the aqueous layer was back extracted with ethyl acetate. The combined organic layers were washed with water, dried over sodium sulfate, and concentrated in vacuo to provide a crude residue. The crude residue was purified using flash column (5% methanol-dichloromethane as eluent) to provide 2',3'-Isopropylidene-2-chloro-$N^6$-cyclopentyladenosine-5'-nitrate (0.435 g). $^1$H NMR (CDCl₃, 300 MHz): δ 1.38 (s, 3H), 1.59 (s, 3H), 1.66-2.13 (m, 9H), 4.50-4.55 (m, 1H), 4.71-4.83 (m, 2H), 5.14-5.17 (m, 1H), 5.31 (d, J=5.7 Hz, 1H), 6.04 (s, 1H), 7.24 (s, 1H), 7.81 (s, 1H). MS m/z 455.44 [M+H]⁺.

Compound 16: 2',3'-Isopropylidene-2-chloro-$N^6$-cyclopentyladenosine-5'-nitrate (0.435 g, as prepared in the previous step) was diluted with TFA (20 mL) and water (5 mL) and the resulting solution was allowed to stir for 30 minutes. The resulting reaction mixture was concentrated in vacuo and the resulting residue was diluted with water (10 mL) and the resulting solution was concentrated in vacuo. The crude residue obtained was diluted with ethyl acetate, transferred to a separatory funnel, washed with saturated aqueous sodium bicarbonate, dried over sodium sulfate and concentrated in vacuo. The crude residue obtained was purified using flash column chromatography on silica gel (using 10% methanol-dichloromethane as eluent) to provide Compound 16 (0.250 g). $^1$H NMR (DMSO-d₆, 300 MHz): δ 1.52-1.95 (m, 9H), 4.13-4.24 (m, 2H), 4.55-4.58 (m, 1H), 4.73-4.85 (m, 2H), 5.50 (bs, 1H), 5.61 (bs, 1H), 5.84 (d, J=5.1 Hz, 1H), 8.33 (bs, 2H), MS m/z 414.85 [M+H]⁺.

6.2 Example 2

Synthesis of Compound 17

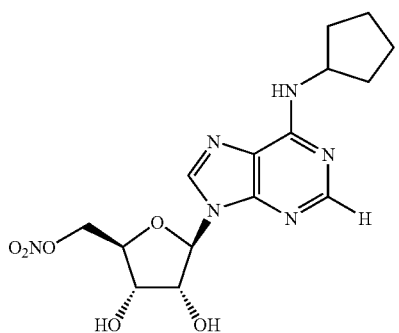

17

$N^6$-Cyclopentyladenosine: A solution of 6-chloroadenosine (43 g) and cyclopentylamine (5 eq.) in ethanol (50 eq.) was heated at reflux for 3 hours then cooled to room temperature. The resultant reaction mixture was concentrated in vacuo and the resultant residue was diluted with water (400 ml) and ethyl acetate (400 ml). The eoganic layer was separated and the aqueous layer was extracted into ethyl acetate (2×400 ml). The combined organic layers were washed with water (2×200 ml), dried over sodium sulfate, concentrated in vacuo and dried under vacuum to provide a solid which was suspended in MeOH (400 mL), filtered and dried to provide N6-cyclopentyladenosine (43.8 g).

2',3'-isopropylidene-$N^6$-cyclopentyladenosine: $N^6$-cyclopentyladenosine (43 g) was diluted with acetone (75 eq.) and to the resultant solution was added 2,2-dimethoxypropane (5 eq.), followed by D-camphorsulphonic acid (1 eq) and the resultant reaction was allowed to stir at room temperature for 3 hours. The resultant reaction mixture was concentrated in vacuo and the resultant residue was diluted with ethyl acetate, then neutralized to pH 7.0 using concentrated aqueous NaHCO₃. The organic layer was separated, dried over sodium sulfate, concentrated in vacuo and dried under vacuum to provide a solid which was suspended in hexane (250 mL), filtered, washed with hexane and dried under vacuum to provide 2',3'-isopropylidene-$N^6$-cyclopentyl adenosine (43 g).

2',3'-isopropylidene-$N^6$-cyclopentyladenosine-5'-nitrate: Acetic anhydride (22 eq) was slowly added to a stirred solution of nitric acid (5 eq., 63%) at −10° C. (acetonitrile-CO₂ bath used for cooling) over a period of 4 hours with the reaction temperature maintained at −5 to 5° C. during the addition. The resultant solution was cooled to −20° C. and a solution of 2',3'-isopropylidene-$N^6$-cyclopentyladenosine (18.250 gm, 0.048 mol) in acetic anhydride (37 mL, 8 eq.) was added slowly. The resultant reaction was allowed to stir at −15 to −5° C. for 1 hour and the resultant reaction mixture was slowly poured slowly into an ice-cold solution of aqueous NaHCO₃ (168 gm in 800 mL water) and ethyl acetate (350 mL) and the resultant solution was allowed to stir for 5 minutes. The organic layer was separated and the aqueous layer was extracted using ethyl acetate (350 mL). The combined organic layers were washed with water, and dried over sodium sulfate, concentrated in vacuo and purified using flash column chromatograpy on silica gel using 70% ethyl acetate-hexane as eluent to provide 2',3'-isopropylidene-$N^6$-cyclopentyladenosine-5'-nitrate (14.9 g).

Compound 17: 2',3'-isopropylidene-$N^6$-cyclopentyladenosine-5'-nitrate (4.8 g) was diluted with a mixture of TFA (20 mL) and water (5 mL) and the resultant reaction was allowed to stir for 30 minutes at room temperature. The resultant reaction mixture was concentrated in vacuo and the resultant residue was diluted with water (10 mL) and concentrated in vacuo. The resultant residue was diluted with ethyl acetate and washed with saturated aqueous sodium bicarbonate, and the organic layer was dried over sodium sulfate and concentrated in vacuo to provide a white solid residue which was dried under vacuum and then recrystallized from cold ethanol to provide Compound 17 (3.1 gm). $^1$H-NMR (DMSO-d₆): δ 1.49-1.58 (m, 4H), 1.66-1.72 (m, 2H), 1.89-1.94 (m, 2H), 4.12-4.17 (m, 1H), 4.28-4.33 (m, 1H), 4.48 (bs, 1H), 4.65-4.87 (m, 3H), 5.5 (d, J=5.1 Hz, 1H), 5.63 (d, J=5.7 Hz, 1H), 5.91 (d, J=5.1 Hz, 1H), 7.75 (d, J=7.5 Hz, 1H), 8.17 (bs, 1H), 8.30 (s, 1H); MS (ES⁺): m/z 381.35 (M+1); Anal. Calcd for $C_{15}H_{20}N_6O_6$: C, 47.37; H, 5.30; N, 22.10. Found: C, 47.49; H, 5.12; N, 21.96.

6.3 Example 3

Synthesis of Compound 18

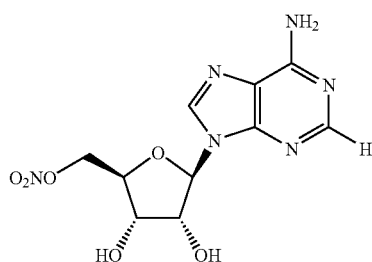

18

2',3'-Isopropylidene-adenosine: A solution of adenosine (43 g) and 2,2-dimethoxypropane (5 eq.) in acetone (75 eq.) was treated with D-camphorsulphonic acid (1 eq) at and the resulting reaction was allowed to stir for 3 hr. The reaction mixture was concentrated in vacuo and diluted with a mixture of saturated aqueous NaHCO$_3$ (250 mL) and ethyl acetate (250 mL). The resulting solution was transferred to a separatory funnel and the organic layer was separated, dried over sodium sulfate, and concentrated in vacuo to provide a solid residue. The solid residue was suspended in hexane, filtered, washed with hexane and dried to provide 2',3'-Isopropylidene-adenosine (43 g). $^1$H NMR (DMSO-d$_6$, 300 MHz): δ 4.12-4.17 (m, 1H), 4.22-4.26 (m, 1H), 4.59 (d, J=4.8 Hz, 1H), 4.74-4.85 (m, 2H), 5.49-5.52 (m, 1H), 5.51 (d, J=5.1 Hz, 1H), 5.84 (d, J=5.1 Hz, 1H), 7.85 (s, 2H), 8.33 (s, 1H). MS t/z 347.11 [M+H]$^+$.

2',3'-Isopropylidene-adenosine-5'-nitrate: A solution of nitric acid (19.8 mL, 60%) was added slowly over a period of 30 minutes to acetic anhydride (100 mL) at −10 to 10° C. (using acetonitrile-CO$_2$ cooling bath) and the reaction mixture was allowed to stir at −10 to 10° C. for 10 minutes. The reaction mixture was then cooled to −30° C. and then a solution of 2',3'-Isopropylidene-adenosine (5.945 g, as prepared in the previous step) in acetic anhydride (49.3 mL) was added slowly. When addition was complete, the resulting reaction was allowed to warm to −5° C. and monitored using TLC (solvent 5% MeOH—CH$_2$Cl$_2$ or 70% EtOAc-hexane). When the reaction was complete, the reaction mixture was poured slowly into an ice cold mixture of saturated aqueous NaHCO$_3$ (300 equivalent in 500 mL water) and ethyl acetate (250 mL). The organic layer was separated and the aqueous layer was back extracted with ethyl acetate. The combined organic layers were washed with water, dried over sodium sulfate, and concentrated in vacuo to provide a crude residue. The crude residue was purified using flash column (5% methanol-dichloromethane as eluent) to provide 2',3'-Isopropylidene-adenosine-5'-nitrate (4.850 g). $^1$H NMR (DMSO-d$_6$, 300 MHz): δ 1.31 (s, 3H), 1.52 (s, 3H), 1.53-1.96 (m, 9H), 4.41-4.43 (m, 1H), 4.68-4.74 (m, 1H), 4.80-4.86 (m, 1H), 5.14-5.16 (m, 1H), 5.41 (d, J=6 Hz, 1H), 6.23 (s, 1H), 7.80 (s, 1H), 8.21 (s, 1H), 8.29 (s, 1H). MS m/z 421.09 [M+H]$^+$.

Compound 18: 2',3'-Isopropylidene-adenosine-5'-nitrate (4.8 g, as prepared in the previous step) was diluted with 4:1 mixture of TFA (20 mL) and water (5 mL) and the resulting solution was allowed to stir at rt for 30 minutes. The resulting reaction mixture was concentrated in vacuo and the resulting residue was diluted with water (10 mL) and concentrated in vacuo to provide a residue which was diluted with ethyl acetate (20 mL). The resulting solution was washed with saturated aqueous sodium bicarbonate, dried over sodium sulfate and concentrated in vacuo to provide a white solid residue which was further dried in vacuo and then recrystallized from ethanol to provide Compound 18 (3.1 g). $^1$H NMR (DMSO-d$_6$, 300 MHz): δ 1.53-1.96 (m, 9H), 4.12-4.17 (m, 1H), 4.28-4.33 (m, 1H), 4.65-4.70 (m, 1H), 4.74-4.87 (m, 1H), 5.50 (d, J=5.1 Hz, 1H), 5.62 (d, J=5.7 Hz, 1H), 5.90 (d, J=5.1 Hz, 1H), 7.74 (d, J=7.5 Hz, 1H), 8.17 (s, 1H), 8.30 (s, 1H). MS m/z 381.04 [M+H]$^+$.

6.4 Example 4

Synthesis of Compound 19

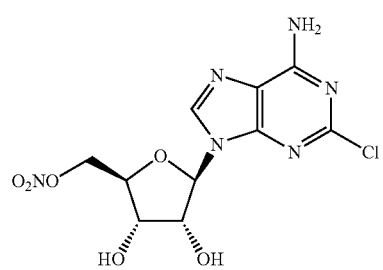

Using the method described in Example 3 and using commercially available 2-chloroadenosine in place of adenosine in step 1, Compound 19 was prepared.

6.5 Example 5

Synthesis of Compound 21

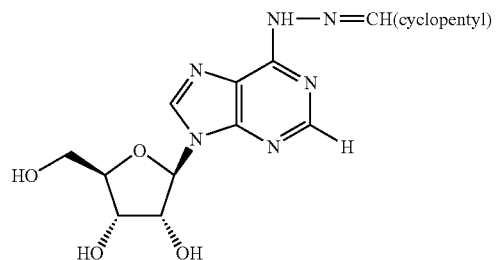

N$^6$-Hydrazinoadenosine: A mixture of 6-chloroadenosine (1 g, 3.5 mmol) and hydrazine monohydrate (5 mL) in MeOH (10 mL) was stirred at 50° C. for 1 hr. The reaction mixture was allowed to cool to room temperature and was then concentrated in vacuo to provide a crude residue which was suspended in MeOH and (10 mL) and stirred at room temperature. The solid product that separated out from the suspension was filtered, washed with MeOH and dried in vacuo to provide N$^6$-hydrazinoadenosine (970 mg) which was used without further purification.

Compound 21: A suspension of N$^6$-hydrazinoadenosine (50 mg, prepared as described in the previous step) and cyclopentanealdehyde (0.26 mmol) in methanol (5 mL) was heated at reflux for 15 minutes and the reaction mixture was cooled to room temperature, then concentrated in vacuo to provide a crude residue which was purified using silica gel flash chromatography (10% methanol/dichloromethane eluent) to provide compound 21 (52 mg). MS m/z 363.11 [M+H]+.

6.6 Example 6

Synthesis of Compound 22

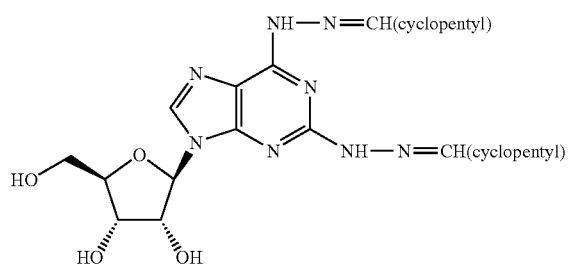

2,6-Dihydrazinoadenosine: A mixture of 2,6-chloro-2',3'5'-triacetyladenosine (0.150 gm, 0.33 mmol) and hydrazine monohydrate (2 mL) in MeOH (5 mL) was heated at reflux for about 8 hours. The reaction mixture was cooled to room temperature and concentrated in vacuo, and the resulting residue was suspended in MeOH (5 mL) and stirred at room temperature for 1 hour. The solid product which separated out from the suspension was filtered, washed with MeOH and dried in vacuo to provide 2,6-dihydrazinoadenosine (65 mg), which was used without further purification.

Compound 22: A mixture of 2,6-dihydrazinoadenosine (60 mg, prepared as described in the previous step) and cyclopentanaldehyde (0.1 mL) in methanol (5 mL) was heated at reflux for 15 minutes. The reaction mixture was then cooled to room temperature and concentrated in vacuo to provide a crude residue which was purified using silica gel flash chromatography (10% methanol/dichloromethane eluent) to provide compound 22 (48 mg). MS m/z 473.25 [M+H]+.

6.7 Example 7

Synthesis of Compound 23 (Sodium Salt)

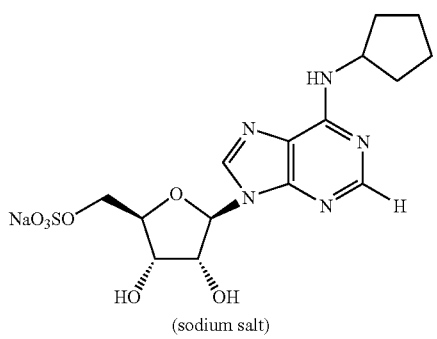

A mixture of 2',3'-isopropylidene-N6-cyclopentyladenosine (1 g, 0.0026 mol, prepared as set forth in Example 1) and sulfur trioxide-pyridine complex (0.0039 mol) in DMF (17 mL) was stirred at room temperature for about 18 hours. The DMF was removed in vacuo and the resulting residue was dried in vacuo. The dried residue was diluted with water (25 mL), neutralized to pH 7.0 using NaOH (1N) and concentrated in vacuo to provide a crude residue which was diluted with an solution of TFA (80% solution in water, 50 mL). The resulting solution was allowed to stir at 25° C. for 30 minutes and the reaction mixture was concentrated in vacuo to afford a crude residue which was diluted with water (10 mL) and concentrated in vacuo. The crude compound obtained was recrystallized from acetone—water to provide compound 23 (sodium salt) (805 mg). 1HMNR (DMSO-d6, 300 MHz): 1.53-1.96 (m, 9H), 3.78-4.10 (m, 4H), 4.43-4.54 (m, 2H), 5.90 (d, J=5.1 Hz, 1H), 8.23 (s, 1H), 8.46 (s, 1H). MS m/z 416.20 [M+H]+.

6.8 Example 8

Synthesis of Compound 24 (Sodium Salt)

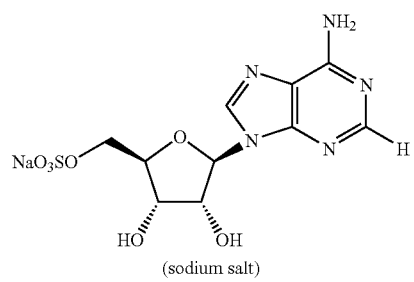

Using the method described in Example 8 and substituting 2',3'-isopropylidene-adenosine (prepared as set forth in Example 3) for 2',3'-isopropylidene-N6-cyclopentyladenosine, Compound 24 (sodium salt) was prepared. 1HMNR (DMSO-d6, 300 MHz): 3.83-3.99 (m, 2H), 4.10-4.14 (m, 2H), 4.50-4.54 (m, 1H), 5.94 (d, J=6 Hz, 1H), 8.5 (s, 1H), 8.73 (s, 1H), 9.50 (bs, 2H). MS m/z 348.05 [M+H]+.

6.9 Example 9

Cell Culture and Membrane Preparation

CHO cells stably transfected with human adenosine AI receptor were grown and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G418, 0.2 mg/mL; A2B, 0.5 mg/mL) at 37° C. in 5% CO2/95% air. Cells were then split 2 or 3 times weekly at a ratio of between 1:5 and 1:20.

Membranes for radioligand binding experiments were prepared from fresh or frozen cells as described in Klotz et al., Naunyn-Schmiedeberg's Arch. Pharmacol., 357:1-9 (1998). The cell suspension was then homogenized in ice-cold hypotonic buffer (5 mM Tris/HCl, 2 mM EDTA, pH 7.4) and the homogenate was spun for 10 minutes (4° C.) at 1,000 g. The membranes were then sedimented from the supernatant for 30 minutes at 100,000 g and resuspended in 50 mM Tris/HCl buffer pH 7.4 (for A3 adenosine receptors: 50 mM Tris/HCl, 10 mM MgCl2, 1 mM EDTA, pH 8.25), frozen in liquid nitrogen at a protein concentration of 1-3 mg/mL and stored at −80° C.

6.10 Example 10

Adenosine Receptor Binding Studies

The affinities of selected Purine Derivatives for the adenosine A1 receptor were determined by measuring the displacement of specific [$^3$H] 2-chloro-N$^6$-cyclopentyl adenosine binding in CHO cells stably transfected with human recombinant A$_1$ adenosine receptor expressed as Ki (nM).

Dissociation constants of unlabeled compounds (K$_i$-values) were determined in competition experiments in 96-well microplates using the A$_1$ selective agonist 2-chloro-N$^6$-[$^3$H] cyclopentyladenosine ([$^3$H]CCPA, 1 nM) for the characterization of A$_1$ receptor binding. Nonspecific binding was determined in the presence of 100 µM R-PIA and 1 mM theophylline, respectively. For details see Klotz et al., *Naunyn-Schmiedeberg's Arch. Pharmacol.*, 357:1-9, 1998. All binding data were calculated by non-linear curve fitting using the program SCTFIT (De Lean et al. *Mol. Pharm.* 1982, 21:5-16).

Results are presented in Table 1 below and show that Compounds 16, 17, 18, 19, 23 (sodium salt), and 25, illustrative Purine Derivatives, are selective for the adenosine A$_1$ receptor and accordingly, are useful for treating a Condition, slowing an animal's metabolic rate, or protecting an animal's heart against myocardial damage during cardioplegia.

TABLE 1

Affinities of illustrative Purine Derivatives for human A$_1$, A$_{2A}$ and A$_3$ adenosine receptors

| Compound | Ki(A$_1$)$^a$ (nM) | Ki(A$_{2A}$)$^b$ (nM) | Ki(A$_3$)$^c$ (nM) |
|---|---|---|---|
| CCPA | 0.83 (0.55-1.25) | 2,270 (1,950-2,660) | 42.3 (32.1-55.8) |
| 16 | 2.63 (2.04-3.38) | 4,190 (2,440-7,200) | 513 (367-715) |
| 17 | 0.97 (0.80-1.17) | 4,692 (2,300-9,560) | 704 (400-1,240) |
| 18 | 5.79 (4.73-7.10) | 951 (530-1,708) | 216 (132-350) |
| 19 | 7 (5.14-9.23) | 10,000 (5,790-15,760) | 900 (445-1,890) |
| 23 (sodium salt) | 4.05 (3.54-4.63) | 9,113 (5,510-15,100) | 1,020 (470-2,220) |
| 25 | 10.6 (6.77-16.70) | >100,000 | 2020 (837-4870) |

$^a$Displacement of specific [$^3$H]CCPA binding in CHO cells stably transfected with human recombinant A$_1$ adenosine receptor, expressed as Ki (nM).
$^b$Displacement of specific [$^3$H]NECA binding in CHO cells stably transfected with human recombinant A$_{2A}$ adenosine receptor, expressed as Ki (nM).
$^c$Displacement of specific [$^3$H]NECA binding in HEK cells stably transfected with human recombinant A$_3$ adenosine receptor, expressed as Ki (nM). All data are geometric means with 95% confidence intervals in parantheses.

6.11 Example 11

Effects of Compound 17 on Septic Shock

Male BALB/c mice (6-8 weeks of age) were used in studies investigating lipopolysaccharide-induced cytokine production and survival. For cytokine production the mice were treated with compound 17 (Oral administration of 0.03 mg/kg) orally by gavage 30 min before being subjected to lipopolysaccharide (1 mg/kg i.p.) for 90 minutes, after this period blood was taken and serum obtained for analysis. Serum was diluted 1:5 prior to being assayed for cytokines using species-specific ELISA kits (R & D Systems) for the chemokine MIP-1α and the cytokine TNF-α levels, which were expressed as pg/mL. For survival studies mice were treated with compound 17 (Oral administration of 0.03 mg/kg) starting 30 mins prior to the mice being subjected to lipopolysaccharide (55 mg/kg i.p.). The survival of the mice was followed over 72 h and expressed as a percentage of surviving mice at each time point. Oral administration of 0.03 mg/kg compound 17 delays lipopolysaccharide (60 mg/kg) induced mortality in conscious mice. N=12-14 per group.

Figure 1:
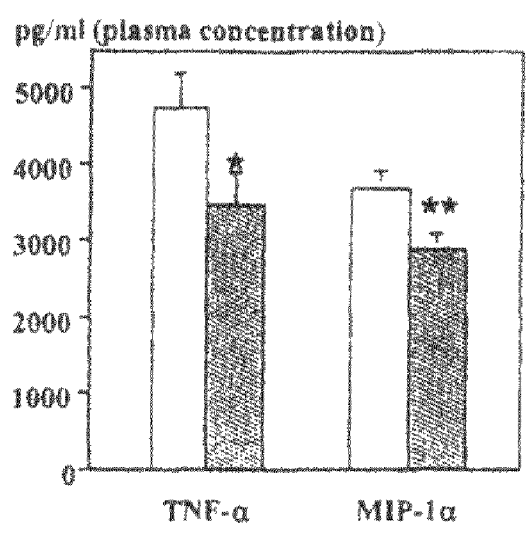

FIG. 1 shows that Compound 17, administered orally to BALB/c mice at a dose of 0.03 mg/kg, reduces lipopolysaccharide-induced plasma TNF-α and MIP-1α production in the BALB/c mouse model.

Figure 2:
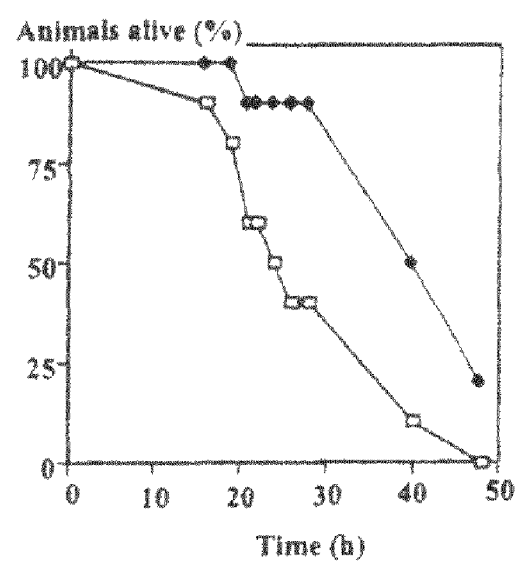
FIG. 2 shows the effect of Compound 17 in survival studies in male BALB/c mice, expressed as the percentage of surviving animals at 10-hour time intervals. Line -□- represents LPS, administered i.p. at a dose of 55 mg/kg, and line -♦- represents Compound 17, administered orally at a dose of 0.03 mg/kg, followed 30 minutes later by LPS, administered i.p. at a dose of 55 mg/kg.

FIG. 2 shows that Compound 17, administered orally to BALB/c mice at a dose of 0.03 mg/kg, reduces lipopolysaccharide-induced mortality in the BALB/c mouse model.

The above example shows that Compound 17, an illustrative Purine Derivative, reduces lipopolysaccharide-induced plasma levels of TNF-α and MIP-1α, and delays lipopolysaccharide-induced mortality in mice.

Accordingly, Compound 17 is useful for treating septic shock.

6.12 Example 12

Anti-Arrhythmia Effects of Compound 17

Heart Perfusion

Male Sprague-Dawley rats (having a body weight of 250 to 300 g) were heparinized using sodium heparin (1,000 U/kg i.p.), followed 10 minutes later by introduction of anesthesia via intraperitoneal administration of sodium pentobarbital (40 mg/kg). Once the animal was anesthetized, the thorax was opened, and the heart was rapidly removed and perfused through the ascending aorta using Krebs-Ringer buffer consisting of NaCl (118 mmol/liter), KCl (4.75 mmol/liter), KH$_2$PO$_4$ (1.18 mmol/liter), MgSO$_4$ (1.18 mmol/liter), CaCl$_2$ (2.5 mmol/liter), NaHCO$_3$ (25 mmol/liter), and glucose (11 mmol/liter). A mixture of 95% O$_2$ and 5% CO$_2$ at 37° C. was bubbled through the perfusate. The heart was initially perfused at a constant pressure of 70 mm Hg. About 10 min after the constant pressure perfusion, perfusion was switched to constant flow perfusion achieved using a microtube pump. The perfusion pressure was maintained at the same level of constant pressure perfusion by adjusting flow rate. Once the flow rate was determined, it was maintained throughout the experiment. The hearts were stimulated by rectangular pulses at a rate of 5 Hz and 2-millisecond duration and twice the diastolic threshold, delivered from a stimulus isolation unit (ADInstruments Ltd, Australia).

Effect of Compound 17 on Ischemia-Induced Arrhythmias

Rat hearts were perfused at constant pressure of 70 mmHg without pacing as described above. Bipolar epicardial electrocardiogram (ECG) was recorded by placing two electrodes on the surface of right appendage and apex. A stainless steel cannula was used as indifferent electrode. The ECG and heart rate were continuously monitored and data were recorded using a PowerLab data acquisition system (ADInstruments Ltd, Australia) in conjunction with a Macintosh computer, and analyzed using Chart.3 computer package. After a 20-minute equilibration period, regional ischemia was induced by ligation of the left anterior descending (LAD) coronary artery, and the ligature was released 30 minutes after occlusion. Compound 17 was applied interperfusate 10 minutes before LAD ligation and was present during LAD ligation. Compound 17 was tested in this model at 10, 30 and 100 pM concentrations. The incidences of ventricular tachycardia (VT) were almost same in control non-treated (12/12) and in treated hearts (20/22). Incidence of ventricular fibrillation (VF) was 58% (7/12) in non-treated hearts, and 9% (2/22) in treated hearts. The total duration of both VT and VF were significantly shortened by compound 17 at concentrations of 30 and 100 pM.

Figure 3:
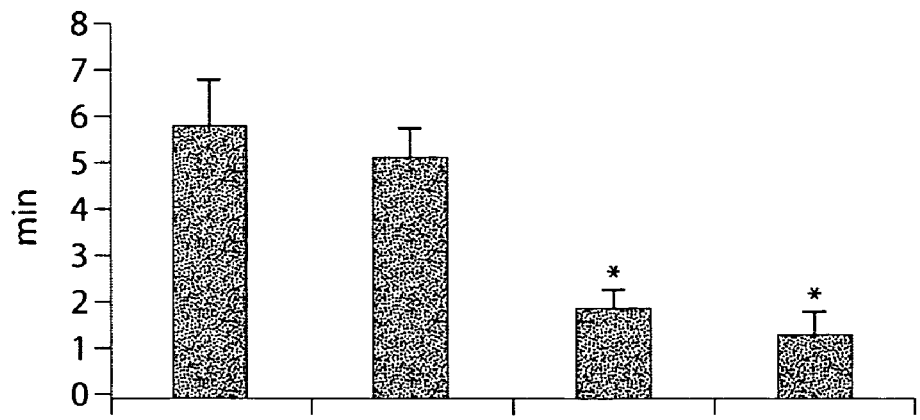
FIG. 3 shows the effects of Compound 17 on the duration of ischemia-induced arrhythmias in isolated perfused rat hearts. The bar graph from left to right, represents: a non-treated control group, Compound 17 administered at 10 pM, Compound 17 administered at 30 pM, and Compound 17 administered at 100 pM, respectively.

FIG. 3 shows that Compound 17 reduces the duration of ischemia-induced arrhythmias in isolated perfused rat hearts relative to a non-treated control group.

The above example shows that Compound 17, an illustrative Purine Derivative, reduces the incidence of ventricular fibrillation and accordingly, is useful for treating a cardiac arrhythmia.

6.13 Example 13

Effect of Compound 17 on Function Recovery after Global Ischemia/Reperfusion Effect of Compound 17 on Function Recovery after Ischemia/Reperfusion Rat hearts were initially perfused at a constant pressure of 70 mm Hg using the procedure described above in section 6.12.1. After a 20 minutes stabilization period, hearts were subjected to 30 minute no-flow ischemia followed by 40 minute reperfusion. In treated hearts, Compound 17 was infused for 10 minutes prior to induction of ischemia. Compound 17 significantly improved +dp/dt$_{max}$ after 30 minutes ischemia followed by 40 minutes of reperfusion at the concentration of 1 nM. Thus, the A1 agonist compound was not only effective in reducing fibrillations but was also effective in improving myocardial contractility (dp/dt) in a myocardial ischemia-reperfusion model in the perfused heart. This observation is in line with data indicating the cardioprotective effect of A1 agonism in various models of ischemia and reperfusion (e.g. Roscoe et al., 2000; Jacobson et al., 2000; Lee et al., 2003), and the cardioprotective effect of A1 agonists in vitro (Goldenberg et al., 2003) and in vivo (Baxter et al., 2001; Donato et al., 2003; Kopecky et al., 2003; Kehl et al., 2003; Arora et al., 2003; Regan et al., 2003; Yang et al., 2003). Effect of compound 12 (1 nM) on maximal rates of development of left ventricular pressure (+dP/dt$_{max}$) after 30 minutes of ischemia followed by 40 minutes of reperfusion. *P<0.05 when compared with the value of control.

FIG. 4 shows that Compound 17 is useful in exerting a cardioprotective effect following ischemia and reperfusion.

The above example shows that Compound 17, an illustrative Purine Derivative, is effective for reducing fibrillations and improving myocardial contractility following ischemia and reperfusion, and accordingly, is useful in treating an ischemic condition or a reperfusion injury.

6.14 Example 14

Synthesis of Compound 25

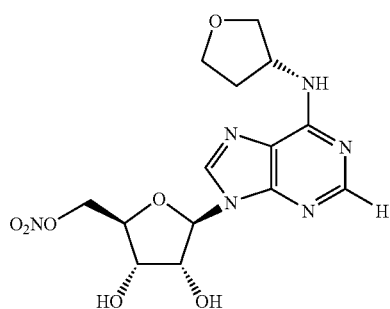

2',3'-Isopropylidene-N$^6$—(R)-(3-tetrahydrofuranyl) adenosine: 2',3'-isopropylidene-6-chloroadenosine (0.750 gm, 0.0023 mol) was diluted with ethanol (20 mL) and to the resultant solution was added R-(3-aminotetrahydrofuranylamine•MeSO$_3$H (0.630 gm, 0.0035 mol), followed by triethylamine (0.9 mL). The resultant reaction was heated at refluxed for 2 days, then cooled to room temperature and the resultant reaction mixture was concentrated in vacuo, diluted with water (25 mL) and ethyl acetate (25 mL), and transferred to a separatory funnel. The organic layer was separated, dried over sodium sulfate and concentrated in vacuo to provide a crude residue which was recrystallized from EtOAc-hexane to provide 2',3'-Isopropylidene-N$^6$—(R)-(3-tetrahydrofuranyl) adenosine (0.680 gm).

N$^6$—(R)-(3-Tetrahydrofuranyl) adenosine: Acetic anhydride (4.6 mL, 30 eq.) was slowly added over a period of about 20 minutes to a stirring solution of nitric acid (0.8 mL, 63% purchased from ACROS) which had been precooled to about −5° C. using an acetonitrile-CO$_2$ bath. The initial reaction is vigorous and addition should be done very carefully to avoid the increase in temperature. After addition of acetic anhydride is complete, the resultant solution was cooled to −20° C. and 2',3'-isopropylidene-N$^6$—R-(3-tetrahydrofuranyl)-adenosine (0.605, 0.0016 mol) was added. The resultant reaction was monitored using thin-layer chromatography (solvent 5% MeOH—CH$_2$Cl$_2$ or 70% EtOAc-hexane). When the reaction was complete, the reaction mixture was poured slowly into a cold solution of NaHCO$_3$ (100 mL) and the resultant solution was diluted with ethyl acetate (100 mL), allowed to stir for 5 minutes, then transferred to a separatory funnel. The organic layer was collected and the aqueous layer was extracted with ethyl acetate (50 mL). The combined organic layers were then washed with water, dried over sodium sulfate, and concentrated in vacuo to afford a crude residue. The crude residue was diluted with TFA (16 mL) and water (4 mL) and the resultant solution was allowed to stir at room temperature for 30 minutes, then concentrated in vacuo. The resultant residue was diluted with water and concentrated in vivo to afford a crude product which was purified using flash column chromatograpy on silica gel using 10% methanol-dichloromethane to provide Compound 25 (265 mg). $^1$H-NMR (DMSO-d$_6$): δ 1.97-2.10 (m, 1H), 2.12-2.20 (m, 1H), 3.57-3.61 (dd, J=4.8 and 4.5 Hz, 1H), 3.67-3.74 (dd, J=8.1 and 8.1 Hz, 1H), 3.81-3.92 (m, 2H), 4.12-4.17 (m, 1H), 4.30 (s, 1H), 4.67 9s, 1H), 4.74-4.87 (m, 3H), 5.48 9s, 1H), 5.61 (s, 1H), 5.91 (d, J=5.1 Hz, 1H), 7.99 (d, J=4.8 Hz, 1H), 8.20 (s, 1H), 8.34 (s, 1H); MS (ES$^+$): m/z 383.06 (M+1).

6.15 Example 15

Effect of Compound 17 on Pain

Male mice (body weight of 25-35 grams) were put in groups as follows: a first group which was intreperitoneally administered buprenorphine (0.3 mg/kg), a second group which was intreperitoneally administered buprenorphine (1 mg/kg), a third group which was intreperitoneally administered Compound 17 (3 mg/kg), a fourth group which was intreperitoneally co-administered Compound 17 (3 mg/kg) and buprenorphine (1.0 mg/kg), and a fifth group which was intreperitoneally co-administered Compound 17 (3 mg/kg) and buprenorphine (0.3 mg/kg). The analgesic effects in mice was measured using an IITC model 33 tail-flick analgesia meter (IITC Inc., Woodland Hills, Calif.) at 0 minutes (baseline control), 5 minutes, 15 minutes, 30 minutes and 60 minutes (in some cases also 90 and 120 minutes) post-treatment, compound or vehicle treatment. Average recoding value of two readings was used for each time point. A baseline for every mouse between 2-4 seconds of latency and a 10-second cut-off time was set for the maximum possible effect of analgesia (% MPE). % MPE was calculated using the following formula: % MPE=[(post-drug value−baseline)/(cut-off time−baseline)]×100.

FIG. 5 shows that Compound 17 is useful in exerting an analgesic effect in an animal.

The results show that Compound 17, an illustrative Purine Derivative, exerts a analgesic effect in an animal, and, accordingly, is useful for the treatment of pain.

6.16 Example 16

Effect of Compound 17 on Pain

Male mice (each having a body weight of 20-30 g) were subcutaneously administered 20 μl of a 1% formalin solution in formaldehyde (prepared by diluting a commercial 4% [w/v] stock formalin solution) into the dorsal region of their left hind paw. The mice were assigned to either a control group and administered vehicle, or to a treatment group and intraperitoneally administered Compound 17 (1.0 mg/kg). Both groups of animals were monitored for a reaction for 30 minutes post-treatment to determine how much time each animal spends licking the treated paw. The licking time in control group (vehicle pretreated animals) was then compared to the licking time in the treatment group in order to calculate the analgesic effect. The 30 minute reaction period was divided into two phases: an early phase which lasts from 0-5 minutes post-treatment, and a late phase which lasts from 10-30 minutes post-treatment.

FIG. 6 shows that Compound 17 is useful in exerting an analgesic effect in an animal.

The results indicate that Compound 17, an illustrative Purine Derivative, exhibits an analgesic effect during the late phase of the response and, accordingly, is useful for treating pain.

6.17 Example 17

Effect of Compound 17 on Pain

BALB/C mice (6-8 weeks of age) were intraperitoneally administered streptozotocin (40 mg/kg, once per day for 5 consecutive days) to induce diabetes (blood glucose levels were greater than 200 mg/mL). Three weeks after the first streptozotocin injection, the animals were intraperitoneally administered Compound 17 (1 mg/kg) into a rear paw and post-treatment allodynia was measured using an Electrovonfrey anesthesiometer (IITC Inc., Woodland Hills Calif. 91367). The analgesic activity of Compound 17 was measured at 0 minutes (control), 15 minutes, 30 minutes and 60 minutes time point after administration of Compound 17.

FIG. 7 shows that Compound 17 is useful in exerting an analgesic effect in a animal.

The results indicate that Compound 17, an illustrative Purine Derivative, produces a marked and lasting analgesic effect, and, accordingly, is useful for treating pain in an animal.

6.18 Example 18

Effect of Compound 17 on Pain

Male Wistar rats (each weighing between 200-250 g, kept under pathogen-free conditions at 24-25° C. and provided with standard rat chow and water ad libitum) were anaesthetized via intraperitoneal administration of pentobarbital (50 mg/kg) and placed in a stereotaxic frame. The atlanto-occipital membrane was exposed and a PE-10 catheter (7.5 cm) was inserted through an incision into the subarachnoidal space. The external end of the catheter was then fixed to the skull, the wound was closed, and the rats were allowed to recover for 7 days post-surgery. Animals without neurological deficits were placed in a plexiglass observation chamber on a metal mesh surface and mechanical thresholds of the plantar surface of the paw were determined using a Dynamic Plantar Aesthesiometer (Ugo Basile, Italy) as follows: Following acclimation, the touch stimulator unit was placed under the animal's paw such that the filament was positioned under the target area of the paw. The filament was then lifted such that it contacted the pad of the animal's paw and continually exerted an increasing upward force on the paw until the animal withdrew the paw. The paw withdrawal threshold was measured 5 times in this manner in turns and the mean of the 5 values was calculated. After control threshold measurements were complete, carrageenan (3%, 100 μl) was administered subcutaneously into a hindpaw, resulting in marked swelling and redness of the treated paw. Three hours after the carrageenan administration, the threshold values were measured again. The animals were then divided into a control group (administered vehicle intrathecally) and a treatment group (administered Compound 17 intrathecally at in a 10 μl injection volume). Threshold determinations were repeated as describe above at 15 minutes, 30 minutes, 60 minutes, 90 minutes and 120 minutes after the administration of vehicle or Compound 17.

FIG. 8 shows that Compound 17 exerts an analgesic effect in a animal.

Results show that Compound 17, an illustrative Purine Derivative, is effective for raising the pain threshold in a rat model of pain, and, accordingly, is useful for treating pain.

6.19 Example 19

Effect of Compound 17 on Pain

Male CD rats (each weighing from 220 g to 250 g) were prepared according to the procedure set forth in Z. Seltzer et al., *Pain*, 43:205-218 (1990). The rats were then anesthetized via intraperitoneal administration of sodium pentobarbital (50 mg/kg). A skin incision was made at the upper ⅓ and ⅔ left thigh area of each rat and the left sciatic nerve was exposed and freed from the surrounding connective tissue. An 8-0 nylon suture was then used to tightly ligate the left sciatic nerve of each rat so that the dorsal ⅓ to ½ of the nerve thickness was trapped in the ligature. The incision was closed using 4-0 sterile suture. Seven days post-surgery, the animals were put into four groups: a first group that was administered vehicle (control group); a second group that was administered Compound 17 at 0.1 mg/kg; a third group that was administered buprenorphine at 0.3 mg/kg; and a fourth group that was co-administered Compound 17 at 0.1 mg/kg and buprenorphine at 0.3 mg/kg. Animals in all four groups were assessed for allodynia immediately prior to treatment and at 10, 20, 30 and 60 minutes post-treatment using the Von Frey Hair test (G. M. Pitcher et al., *J Neurosci Methods*, 87:185-93 (1999)).

FIG. 9 shows that Compound 17, alone or in combination with buprenorphine, exerts an analgesic effect in a animal.

The results show that Compound 17, an illustrative Purine Derivative, exerts an analgesic effect in an animal, and, accordingly, is useful for treating pain.

6.20 Example 20

Effect of Compound 17 on Heart Rate

Adult male Wistar rats (each weighing from about 350 g to about 400 g) were anesthetized as in Example 19, then prepared for monitoring of blood pressure and heart rate. Compound 17 was then intravenously administered via the femoral vein at a dose of 1 ng/kg/minute, 10 ng/kg/minute, or 1000 ng/kg/minute (n=2 animals per dosage size) for a total administration period of 20 minutes.

The results show that a 10 ng/kg/minute dose of lowered heart rate from 440 beats per minute to 370 beats per minute and that the 1000 ng/kg/minute dose reduced heart rate from 440 beats per minute to 150 beats per minute. Thus, Compound 17, an illustrative Purine Derivative is exerts a heart rate lowering effect, and accordingly, a Purine Derivative is useful for lowering an animal's ventricular rate to a rate of not less than about 40 beats per minute.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety.

What is claimed is:

1. A method for treating a neurological disorder, a cardiovascular disease, an ischemic condition, diabetes, obesity, a wasting disease or a reperfusion injury, or a neurological disorder selected from the group consisting of pain, headache, a sleep disorder, a cranial nerve disorder, a neuromuscular disease, a cerebrovascular disease and a neuroopthalmic disorder, the method comprising administering to an animal in need thereof a compound of:

1) formula (Ia):

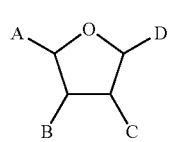

(Ia)

wherein
A is —CH$_2$OSO$_2$NH$_2$;
B and C are —OH;
D is

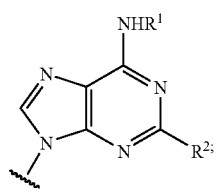

A and B are trans with respect to each other;
B and C are cis with respect to each other;
C and D are cis or trans with respect to each other;
R$^1$ is —C$_3$-C$_8$ monocyclic cycloalkyl, —C$_3$-C$_8$ monocyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —C$_8$-C$_{12}$ bicyclic cycloalkyl, or —C$_8$-C$_{12}$ bicyclic cycloalkenyl;

R$^2$ is -halo, —CN, —NHR$^8$, —OR$^8$, —SR$^8$, —NHC(O)OR$^8$, —NHC(O)R$^4$, —NHC(O)NHR$^8$, —NHNHC(O)R$^4$, —NHNHC(O)OR$^8$, —NHNHC(O)NHR$^8$, or —NH—N=C(R$^6$)R$^7$;
R$^4$ is —H, —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);
R$^7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), or —(CH$_2$)$_n$-(8- to 12-membered bicyclic heterocycle);
R$_8$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl; and
each n is independently an integer ranging from 1 to 5;

2) formula (Ib):

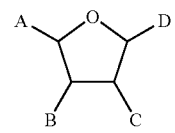

(Ib)

wherein
A is —CH$_2$ONO$_2$;
B and C are —OH;
D is

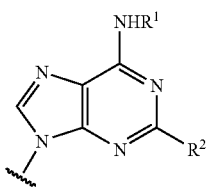

A and B are trans with respect to each other;
B and C are cis with respect to each other;
C and D are cis or trans with respect to each other;
R$^1$ is —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

R$^2$ is —CN, —NHR$^4$, —NHC(O)R$^4$, —NHC(O)OR$^4$, —NHC(O)NHR$^4$, —NHNHC(O)R$^4$, —NHNHC(O)OR$^4$, —NHNHC(O)NHR$^4$, or —NH—N=C(R$^6$)R$^7$;

R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkenyl), -phenylene-(CH$_2$)$_n$COOH, or -phenylene-(CH$_2$)$_n$COO—(C$_1$-C$_{10}$ alkyl);

R$^7$ is —H, —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkenyl) or —(CH$_2$)$_n$—(C$_8$-C$_{12}$ bicyclic cycloalkyl); and each n is independently an integer ranging from 1 to 5;

3) formula (Ic):

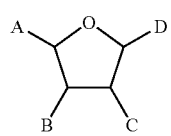

(Ic)

wherein
A is —CH$_2$NHR$^5$;
B and C are —OH;
D is

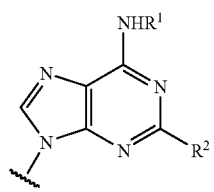

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl,
—(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

R$^2$ is —NHR$^4$, —OR$^4$, —SR$^4$, —NHC(O)R$^4$, —NHC(O)OR$^4$, —NHC(O)NHR$^4$, —NHNHC(O)R$^4$, —NHNHC(O)NHR$^4$, or —NHNHC(O)OR$^4$;

R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^5$ is —C(O)O(C$_1$-C$_{10}$ alkyl), —C(O)NH(C$_1$-C$_{10}$ alkyl), —C(O)N(C$_1$-C$_{10}$ alkyl)$_2$, —C(O)NH-aryl, —CH(NH$_2$)NH$_2$ or —CH(NH$_2$)NH(C$_1$-C$_{10}$ alkyl);
and
each n is independently an integer ranging from 1 to 5;

4) formula (Id):

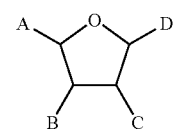

(Id)

wherein
A is —R$^3$;
B and C are —OH;
D is

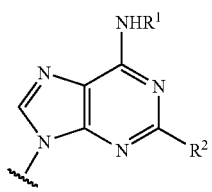

A and B are trans with respect to each other;
B and C are cis with respect to each other;
C and D are cis or trans with respect to each other;
R$^1$ is —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

R$^2$ is —H, -halo, —CN, —NHR$^4$, —OR$^4$, —SR$^4$, —NHC(O)R$^4$, —NHC(O)OR$^4$, —NHC(O)NHR$^4$, —NHNHC(O)R$^4$, —NHNHC(O)NHR$^4$, —NHNHC(O)OR$^4$ or —NH—N=C(R$^6$)R$^7$;

R$^3$ is —CH$_2$ONO or —CH$_2$OSO$_3$H;

R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);

R$^7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), or —(CH$_2$)$_n$-(8- to 12-membered bicyclic heterocycle); and each n is independently an integer ranging from 1 to 5;

5) formula (Ie):

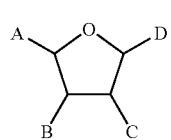

(Ie)

wherein

A is —CH$_2$R$^3$;

B and C are —OH;

D is

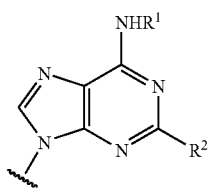

A and B are trans with respect to each other;

B and C are cis with respect to each other;

C and D are cis or trans with respect to each other;

R$^1$ is -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

R$^2$ is -halo, —CN, —NHC(O)R$^4$, —NHR$^4$, —OR$^4$, —SR$^4$, —NHC(O)OR$^4$, —NHC(O)NHR$^4$, —NHNHC(O)R$^4$, —NHNHC(O)OR$^4$, —NHNHC(O)NHR$^4$, or —NH—N=C(R$^6$)R$^7$;

R$^3$ is —OSO$_2$NH(C$_1$-C$_{10}$ alkyl), —OSO$_2$N(C$_1$-C$_{10}$ alkyl)$_2$, or —OSO$_2$NH-aryl;

R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);

R$_7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$-(3- to 7-membered monocyclic heterocycle), or —(CH$_2$)$_n$-(8- to 12-membered bicyclic heterocycle); and each n is independently an integer ranging from 1 to 5;

6) formula (If):

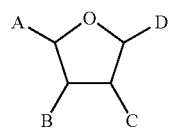

(If)

wherein

A is —CH$_2$ONO$_2$;

B and C are —OH;

D is

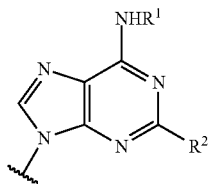

A and B are trans with respect to each other;

B and C are cis with respect to each other;

C and D are cis or trans with respect to each other;

R$^1$ is —C$_3$-C$_8$ monocyclic cycloalkyl; and

R$^2$ is —H or -halo;

7) formula (Ig):

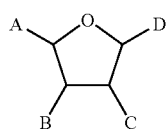

(Ig)

wherein
A is —CH$_2$ONO$_2$;
B and C are —OH;
D is

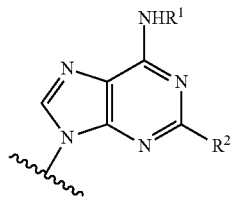

A and B are trans with respect to each other;
B and C are cis with respect to each other;
C and D are cis or trans with respect to each other; and
R$^1$ is -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl),
R$^2$ is —H or -halo;
or a pharmaceutically acceptable salt thereof in an amount effective to treat the neurological disorder, such that said neurological disorder, cardiovascular disease, ischemic condition, diabetes, obesity, wasting disease or reperfusion injury is treated.

2. A method for protecting an animal's heart against myocardial damage during cardioplegia, the method comprising administering to an animal in need thereof a cardioplegia-inducing agent and an effective amount of a compound of:
1) formula (Ia):

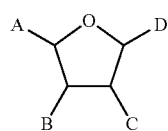

(Ia)

wherein
A is —CH$_2$OSO$_2$NH$_2$;
B and C are —OH;
D is

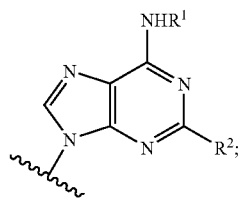

A and B are trans with respect to each other;
B and C are cis with respect to each other;
C and D are cis or trans with respect to each other;
R$^1$ is —C$_3$-C$_8$ monocyclic cycloalkyl, —C$_3$-C$_8$ monocyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —C$_8$-C$_{12}$ bicyclic cycloalkyl, or —C$_8$-C$_{12}$ bicyclic cycloalkenyl;

R$^2$ is -halo, —CN, —NHR$^8$, —OR$^8$, —SR$^8$, —NHC(O)OR$^8$, —NHC(O)R$^4$, —NHC(O)NHR$^8$, —NHNHC(O)R$^4$, —NHNHC(O)OR$^8$, —NHNHC(O)NHR$^8$, or —NH—N=C(R$^6$)R$^7$;

R$^4$ is —H, —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)—COOH, or -phenylene-(CH$_2$)$_n$COO—(C$_1$-C$_{10}$ alkyl);

R$^7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$), —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), or —(CH$_2$)$_n$-(8- to 12-membered bicyclic heterocycle);

R$_8$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$), —(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl; and each n is independently an integer ranging from 1 to 5;
2) formula (Ib):

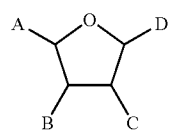

(Ib)

wherein
A is —CH$_2$ONO$_2$;
B and C are —OH;
D is

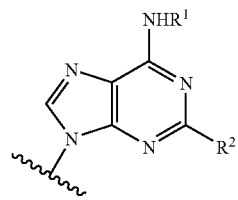

A and B are trans with respect to each other;
B and C are cis with respect to each other;
C and D are cis or trans with respect to each other;

R¹ is —C₁-C₁₀ alkyl, -aryl, -3- to 7-membered monocyclic heterocycle, -8- to 12-membered bicyclic heterocycle, —C₃-C₈ monocyclic cycloalkyl, —C₃-C₈ monocyclic cycloalkenyl, —C₈-C₁₂ bicyclic cycloalkyl, —C₈-C₁₂ bicyclic cycloalkenyl, —(CH₂)ₙ —(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkyl), —(CH₂)ₙ—(C₈-C₁₂ bicyclic cycloalkenyl), or —(CH₂)ₙ-aryl;

R² is —CN, —NHR⁴, —NHC(O)R⁴, —NHC(O)OR⁴, —NHC(O)NHR⁴, —NHNHC(O)R⁴, —NHNHC(O)OR⁴, —NHNHC(O)NHR⁴, or —NH—N=C(R⁶)R⁷;

R⁴ is —C₁-C₁₅ alkyl, -aryl, —(CH₂)ₙ-aryl, —(CH₂)ₙ-(3- to 7-membered monocyclic heterocycle), —(CH₂)ₙ-(8- to 12-membered bicyclic heterocycle), —(CH₂)ₙ—(C₃-C₈ monocyclic cycloalkyl), —(CH₂)ₙ —(C₃-C₈ monocyclic cycloalkenyl), —(CH₂)ₙ—(C₈-C₁₂ bicyclic cycloalkyl), —(CH₂)ₙ —(C₈-C₁₂ bicyclic cycloalkenyl), —C≡C—(C₁-C₁₀ alkyl) or —C≡C-aryl;

R⁶ is —C₁-C₁₀ alkyl, -aryl, —(CH₂)ₙ-aryl, —(CH₂)ₙ-(3- to 7-membered monocyclic heterocycle), —(CH₂)ₙ-(8- to 12-membered bicyclic heterocycle), —(CH₂)ₙ—(C₃-C₈ monocyclic cycloalkyl), —(CH₂)ₙ —(C₃-C₈ monocyclic cycloalkenyl), —(CH₂)ₙ—(C₈-C₁₂ bicyclic cycloalkyl), —(CH₂)ₙ —(C₈-C₁₂ bicyclic cycloalkenyl), —(CH₂), —(C₃-C₈ monocyclic cycloalkenyl), -phenylene-(CH₂)ₙCOOH, or -phenylene-(CH₂)ₙCOO—(C₁-C₁₀ alkyl);

R⁷ is —H, —C₁-C₁₀ alkyl, -aryl, —(CH₂)ₙ-aryl, —(CH₂)ₙ-(3- to 7-membered monocyclic heterocycle), —(CH₂)ₙ-(8- to 12-membered bicyclic heterocycle), —(CH₂)ₙ—(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkenyl) or —(CH₂)ₙ—(C₈-C₁₂ bicyclic cycloalkyl); and each n is independently an integer ranging from 1 to 5;

3) formula (Ic):

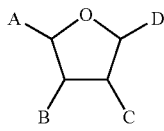

(Ic)

wherein
A is —CH₂NHR⁵;
B and C are —OH;
D is

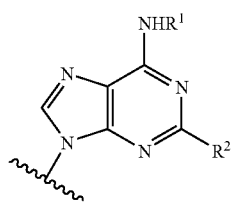

A and B are trans with respect to each other;
B and C are cis with respect to each other;
C and D are cis or trans with respect to each other;
R¹ is —H, —C₁-C₁₀ alkyl, -aryl, -3- to 7-membered monocyclic heterocycle, -8- to 12-membered bicyclic heterocycle, —C₃-C₈ monocyclic cycloalkyl, —C₃-C₈ monocyclic cycloalkenyl, —C₈-C₁₂ bicyclic cycloalkyl, —C₈-C₁₂ bicyclic cycloalkenyl, —(CH₂)ₙ —(C₃-C₈ monocyclic cycloalkyl), —(CH₂)ₙ —(C₃-C₈ monocyclic cycloalkenyl), —(CH₂)ₙ—(C₈-C₁₂ bicyclic cycloalkyl), —(CH₂)ₙ —(C₈-C₁₂ bicyclic cycloalkenyl), or —(CH₂)ₙ-aryl;

R² is —NHR⁴, —OR⁴, —SR⁴, —NHC(O)R⁴, —NHC(O)OR⁴, —NHC(O)NHR⁴, —NHNHC(O)R⁴, —NHNHC(O)NHR⁴, or —NHNHC(O)OR⁴;

R⁴ is —C₁-C₁₅ alkyl, -aryl, —(CH₂)ₙ-aryl, —(CH₂)ₙ-(3- to 7-membered monocyclic heterocycle), —(CH₂)ₙ-(8- to 12-membered bicyclic heterocycle), —(CH₂)ₙ—(C₃-C₈ monocyclic cycloalkyl), —(CH₂)ₙ —(C₃-C₈ monocyclic cycloalkenyl), —(CH₂)ₙ—(C₈-C₁₂ bicyclic cycloalkyl), —(CH₂)ₙ —(C₈-C₁₂ bicyclic cycloalkenyl), —C≡C—(C₁-C₁₀ alkyl) or —C≡C-aryl;

R⁵ is —C(O)O(C₁-C₁₀ alkyl), —C(O)NH(C₁-C₁₀ alkyl), —C(O)N(C₁-C₁₀ alkyl)₂, —C(O)NH-aryl, —CH(NH₂)NH₂ or —CH(NH₂)NH(C₁-C₁₀ alkyl); and each n is independently an integer ranging from 1 to 5;

4) formula (Id):

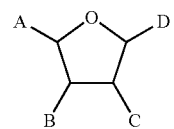

(Id)

wherein
A is —R³;
B and C are —OH;
D is

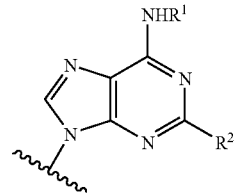

A and B are trans with respect to each other;
B and C are cis with respect to each other;
C and D are cis or trans with respect to each other;
R¹ is —C₁-C₁₀ alkyl, -aryl, -3- to 7-membered monocyclic heterocycle, -8- to 12-membered bicyclic heterocycle, —C₃-C₈ monocyclic cycloalkyl, —C₃-C₈ monocyclic cycloalkenyl, —C₈-C₁₂ bicyclic cycloalkyl, —C₈-C₁₂ bicyclic cycloalkenyl, —(CH₂)ₙ —(C₃-C₈ monocyclic cycloalkyl), —(CH₂)ₙ —(C₃-C₈ monocyclic cycloalkenyl), —(CH₂)ₙ—(C₈-C₁₂ bicyclic cycloalkyl), —(CH₂)ₙ —(C₈-C₁₂ bicyclic cycloalkenyl), or —(CH₂)ₙ-aryl;

R² is —H, -halo, —CN, —NHR⁴, —OR⁴, —SR⁴, —NHC(O)R⁴, —NHC(O)OR⁴, —NHC(O)NHR⁴, —NHNHC(O)R⁴, —NHNHC(O)NHR⁴, —NHNHC(O)OR⁴ or —NH—N=C(R⁶)R⁷;

R³ is —CH₂ONO or —CH₂OSO₃H;

R⁴ is —C₁-C₁₅ alkyl, -aryl, —(CH₂)ₙ-aryl, —(CH₂)ₙ-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$ —(C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);

R$^7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$ (C$_8$-C$_{12}$ bicyclic cycloalkenyl), —(CH$_2$)$_n$-(3- to 7-membered monocyclic heterocycle), or —(CH$_2$)$_n$-(8- to 12-membered bicyclic heterocycle); and each n is independently an integer ranging from 1 to 5;

5) formula (Ie):

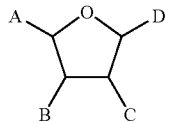

(Ie)

wherein
A is —CH$_2$R$^3$;
B and C are —OH;
D is

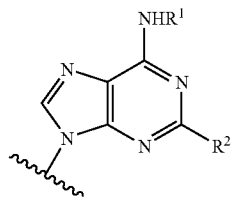

A and B are trans with respect to each other;
B and C are cis with respect to each other;
C and D are cis or trans with respect to each other;
R$^1$ is -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;
R$^2$ is -halo, —CN, —NHC(O)R$^4$, —NHR$^4$, —OR$^4$, —SR$^4$, —NHC(O)OR$^4$, —NHC(O)NHR$^4$, —NHNHC(O)R$^4$, —NHNHC(O)OR$^4$, —NHNHC(O)NHR$^4$, or —NH—N=C(R$^6$)R$^7$;
R$^3$ is —OSO$_2$NH(C$_1$-C$_{10}$ alkyl), —OSO$_2$N(C$_1$-C$_{10}$ alkyl)$_2$, or —OSO$_2$NH-aryl;
R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$ (C$_8$-C$_{12}$ bicyclic cycloalkenyl), —C≡C—(C$_1$-C$_{10}$ alkyl) or —C≡C-aryl;

R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);

R$_7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$-(3- to 7-membered monocyclic heterocycle), or —(CH$_2$)$_n$-(8- to 12-membered bicyclic heterocycle); and each n is independently an integer ranging from 1 to 5;

6) formula (If):

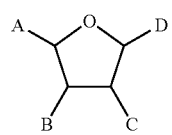

(If)

wherein
A is —CH$_2$ONO$_2$;
B and C are —OH;
D is

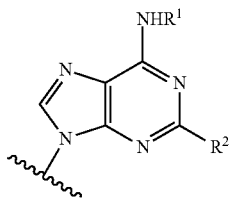

A and B are trans with respect to each other;
B and C are cis with respect to each other;
C and D are cis or trans with respect to each other;
R$^1$ is —C$_1$-C$_8$ monocyclic cycloalkyl; and
R$^2$ is —H or -halo;

7) formula (Ig):

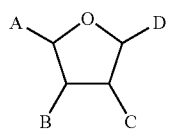

(Ig)

wherein
A is —CH$_2$ONO$_2$;
B and C are —OH;
D is

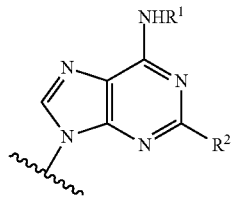

A and B are trans with respect to each other;
B and C are cis with respect to each other;
C and D are cis or trans with respect to each other; and
R$^1$ is —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl),
R$^2$ is —H or -halo;

8) formula (II):

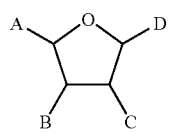

(II)

wherein
A is —CH$_2$OH;
B and C are —OH;
D is

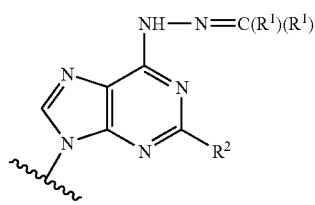

A and B are trans with respect to each other;
B and C are cis with respect to each other;
C and D are cis or trans with respect to each other;
each R$^1$ is independently —H, —C$_1$-C$_{10}$ alkyl, —(CH$_2$)$_m$-(3- to 7-membered monocyclic heterocycle), —(CH$_2$)$_m$-(8- to 12-membered bicyclic heterocycle), —(CH$_2$)$_m$—(C$_8$-C$_{12}$ bicyclic cycloalkyl), —(CH$_2$)$_m$—(C$_8$-C$_{12}$ bicyclic cycloalkenyl), or —(CH$_2$)$_m$-aryl, or both R$^1$ groups together with the carbon atom to which they are attached form a —C$_3$-C$_8$ monocyclic cycloalkyl, a —C$_3$-C$_8$ monocyclic cycloalkenyl, a —C$_8$-C$_{12}$ bicyclic cycloalkyl, or a —C$_8$-C$_{12}$ bicyclic cycloalkenyl;
R$^2$ is —OR$^4$, —SR$^4$, —NHNHC(O)R$^3$, —NHNHC(O)NHR$^3$, —NHNHC(O)OR$^7$, or —NH—N=C(R$^5$)R$^6$;

R$^3$ is —H, —C$^1$-C$^{10}$ alkyl, —(CH$^2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, —O—(CH$_2$)$_n$—(C$_8$-C$_{12}$ bicyclic cycloalkyl), —O—(CH$_2$)$_n$—(C$_3$-C$_8$ monocyclic cycloalkyl), O—(CH$_2$)$_n$—(C$_3$-C$_8$ monocyclic cycloalkenyl), —C≡C—(C$_1$-C$_{10}$ alkyl) or —C≡C-aryl;

R$^4$ is —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$-aryl, or —C≡C-aryl;

R$^5$ and R$^6$ are each independently —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, -phenylene-(CH$_2$)$_n$COOH, or -phenylene-(CH$_2$)$_n$COO—(C$_1$-C$_{10}$ alkyl), or R$^5$ and R$^6$ together with the carbon atom to which they are attached form a C$_3$-C$_8$ monocyclic cycloalkyl or a C$_8$-C$_{12}$ bicyclic cycloalkyl;

R$^7$ is —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, —C≡C—(C$_1$-C$_{10}$ alkyl) or —C≡C-aryl;

m is an integer ranging from 0 to 3; and
each n is independently an integer ranging from 0 to 5;

9) formula (III):

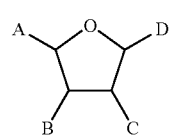

(III)

wherein
A is —CH$_2$R$^3$;
B and C are —OH;
D is

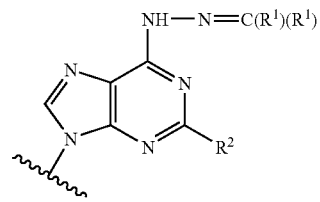

A and B are trans with respect to each other;
B and C are cis with respect to each other;
C and D are cis or trans with respect to each other;

each $R^1$ is independently —$C_1$-$C_{10}$ alkyl, —$(CH_2)_m$-(3- to 7-membered monocyclic heterocycle), —$(CH_2)_m$-(8- to 12-membered bicyclic heterocycle), —$(CH_2)_m$—($C_3$-$C_8$ monocyclic cycloalkyl), —$(CH_2)_m$—($C_3$-$C_8$ monocyclic cycloalkenyl), —$(CH_2)_m$—($C_8$-$C_{12}$ bicyclic cycloalkyl), —$(CH_2)_n$—($C_8$-$C_{12}$ bicyclic cycloalkenyl), or —$(CH_2)_m$-aryl, or two $R^1$ groups, together with the carbon atom to which they are attached, form a —$C_3$-$C_8$ monocyclic cycloalkyl, a —$C_3$-$C_8$ monocyclic cycloalkenyl, a —$C_8$-$C_{12}$ bicyclic cycloalkyl, or a —$C_8$-$C_{12}$ bicyclic cycloalkenyl;

$R^2$ is —H, —CN, -halo, —$N(R^4)_2$, —$OR^4$, —$SR^4$, —$NHC(O)R^4$, —$NHC(O)OR^4$, —$NHC(O)NHR^4$, —$NHNHC(O)R^4$, —$NHNHC(O)NHR^4$, —$NHNHC(O)OR^4$, or —NH—N=$C(R^6)R^7$;

$R^3$ is —$ONO_2$, —ONO, —$OSO_3H$, —$OSO_2NH_2$, —$OSO_2NH(C_1$-$C_{10}$ alkyl), —$OSO_2N(C_1$-$C_{10}$ alkyl)$_2$, —$OSO_2NH$-aryl or —$N(R^5)_2$;

each $R^4$ is independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, —$C(O)O(C_1$-$C_{10}$ alkyl), —$C(O)NH(C_1$-$C_{10}$ alkyl), —$C(O)N(C_1$-$C_{10}$ alkyl)$_2$, —$C(O)NH$-aryl, —$C(O)N(C_1$-$C_{10}$ alkyl)$_2$, —$CH(NH_2)NH_2$ or —$CH(NH_2)NH(C_1$-$C_{10}$ alkyl);

each $R^5$ is independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;

$R^6$ and $R^7$ are each independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, -phenylene-$(CH_2)_n$COOH, or -phenylene-$(CH_2)_n$COO—$(C_1$-$C_{10}$ alkyl), or $R^6$ and $R^7$, together with the carbon atom to which they are attached, form a —$C_3$-$C_8$ monocyclic cycloalkyl, —$C_3$-$C_8$ monocyclic cycloalkenyl, or a $C_8$-$C_{12}$ bicyclic cycloalkenyl;

m is an integer ranging from 0 to 3; and each n is independently an integer ranging from 0 to 5;

10) formula (IV):

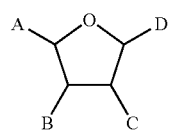

(IV)

wherein

A is —$CH_2OH$;

B and C are —OH;

D is

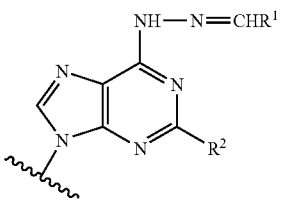

A and B are trans with respect to each other;

B and C are cis with respect to each other;

C and D are cis or trans with respect to each other;

$R^1$ is —$C_3$-$C_8$ monocyclic cycloalkyl or —$C_3$-$C_8$ monocyclic cycloalkenyl;

$R^2$ is —H, -halo, —CN, —$OR^3$, —$SR^3$, —$N(R^3)_2$, —$NHNHC(O)R^3$, —$NHNHC(O)NHR^3$, —$NHNHC(O)OR^3$, or —NH—N=$C(R^4)R^5$;

each $R^3$ is independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, —C≡C—($C_1$-$C_{10}$ alkyl) or —C≡C-aryl;

$R^4$ and $R^5$ are each independently —H, —$C_1$-$C_{10}$ alkyl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-aryl, -phenylene-$(CH_2)_n$COOH, or -phenylene-$(CH_2)_n$COO$(C_1$-$C_{10}$ alkyl), or $R^4$ and $R^5$, together with the carbon atom to which they are attached, form a $C_3$-$C_8$ monocyclic cycloalkyl, a $C_3$-$C_8$ monocyclic cycloalkenyl, a —$C_8$-$C_{12}$ bicyclic cycloalkyl, or a —$C_8$-$C_{12}$ bicyclic cycloalkenyl; and each n is independently an integer ranging from 0 to 5;

11) formula (V):

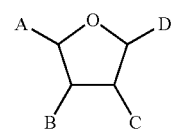

(V)

wherein
A is —CH$_2$OH;
B and C are —OH;
D is

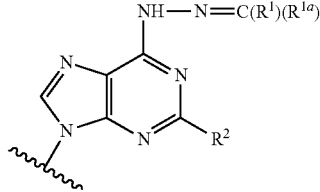

A and B are trans with respect to each other;
B and C are cis with respect to each other;
C and D are cis or trans with respect to each other;
R$^1$ is —C$_1$-C$_{10}$ alkyl, —(CH$_2$)$_m$-(3- to 7-membered monocyclic heterocycle), —(CH$_2$)$_m$-(8- to 12-membered bicyclic heterocycle), —(CH$_2$)$_m$—(C$_8$-C$_{12}$ bicyclic cycloalkyl), —(CH$_2$)$_n$—(C$_8$-C$_{12}$ bicyclic cycloalkenyl), —(CH$_2$)$_m$—(C$_3$-C$_8$ monocyclic cycloalkyl), —(CH$_2$)$_m$—(C$_3$-C$_8$ monocyclic cycloalkenyl) or —(CH$_2$)$_m$-aryl, or R$^1$ and R$^{1a}$ together with the carbon atom to which they are attached form a —C$_3$-C$_8$ monocyclic cycloalkyl, a —C$_3$-C$_8$ monocyclic cycloalkenyl, a —C$_8$-C$_{12}$ bicyclic cycloalkyl, or a —C$_8$-C$_{12}$ bicyclic cycloalkenyl;
R$^{1a}$ is —C$_3$-C$_8$ monocyclic cycloalkyl or —C$_3$-C$_8$ monocyclic cycloalkenyl;
R$^2$ is —OR$^4$, —SR$^4$, —NHNHC(O)R$^3$, —NHNHC(O)NHR$^3$, —NHNHC(O)OR$^3$, or —NH—N=C(R$^5$)R$^6$;
R$^3$ is —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, —C≡C—(C$_1$-C$_{10}$ alkyl) or —C≡C-aryl;
R$^4$ is —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$-aryl, —C≡C—(C$_1$-C$_{10}$ alkyl) or —C≡C-aryl;
R$^5$ and R$^6$ are each independently —H, —C$_1$-C$_{10}$ alkyl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-aryl, -phenylene-(CH$_2$)$_n$COOH, or -phenylene-(CH$_2$)$_n$COO—(C$_1$-C$_{10}$ alkyl), or R$^5$ and R$^6$ together with the carbon atom to which they are attached form a C$_3$-C$_8$ monocyclic cycloalkyl, a C$_3$-C$_8$ monocyclic cycloalkenyl, a —C$_8$-C$_{12}$ bicyclic cycloalkyl, or a —C$_8$-C$_{12}$ bicyclic cycloalkenyl;
m is an integer ranging from 0 to 3; and
each n is independently an integer ranging from 0 to 5;
or pharmaceutically acceptable salt of the compound of claim 1, such that said animal's heart is protected against myocardial damage during cardioplegia.

3. A method for reducing an animal's rate of metabolism or rate of oxygen consumption, the method comprising administering to an animal in need thereof a compound of:
1) formula (Ia):

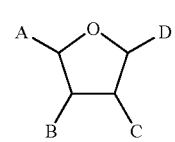

(Ia)

wherein
A is —CH$_2$OSO$_2$NH$_2$;
B and C are —OH;
D is

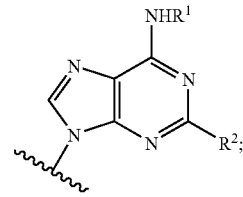

A and B are trans with respect to each other;
B and C are cis with respect to each other;
C and D are cis or trans with respect to each other;
R$^1$ is —C$_3$-C$_8$ monocyclic cycloalkyl, —C$_3$-C$_8$ monocyclic cycloalkenyl, —(CH$_2$)$_n$—(C$_3$-C$_8$ monocyclic cycloalkyl), —(CH$_2$)$_n$—(C$_3$-C$_8$ monocyclic cycloalkenyl), —C$_8$-C$_{12}$ bicyclic cycloalkyl, or —C$_8$-C$_{12}$ bicyclic cycloalkenyl;
R$^2$ is -halo, —CN, —NHR$^8$, —OR$^8$, —SR$^8$, —NHC(O)OR$^8$, —NHC(O)R$^4$, —NHC(O)NHR$^8$, —NHNHC(O)R$^4$, —NHNHC(O)OR$^8$, —NHNHC(O)NHR$^8$, or —NH—N=C(R$^6$)R$^7$;
R$^4$ is —H, —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^6$ is —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$-(3- to 7-membered monocyclic heterocycle), —(CH$_2$)$_n$-(8- to 12-membered bicyclic heterocycle), -phenylene-(CH$_2$)$_n$COOH, or -phenylene-(CH$_2$)$_n$COO—(C$_1$-C$_{10}$ alkyl);
R$^7$ is —H, —C$_1$-C$_{10}$ alkyl, -aryl, —(CH$_2$)$_n$-aryl, —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$ —(C$_8$-C$_{12}$ bicyclic cycloalkenyl), —(CH$_2$)$_n$-(3- to 7-membered monocyclic heterocycle), or —(CH$_2$)$_n$-(8- to 12-membered bicyclic heterocycle);
R$_8$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl; and each n is independently an integer ranging from 1 to 5;
2) formula (Ib):

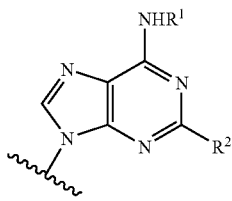

(Ib)

wherein
A is —CH$_2$ONO$_2$;
B and C are —OH;
D is

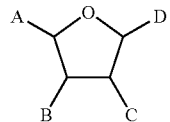

A and B are trans with respect to each other;
B and C are cis with respect to each other;
C and D are cis or trans with respect to each other;
R$^1$ is —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$ —(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;
R$^2$ is —CN, —NHR$^4$, —NHC(O)R$^4$, —NHC(O)OR$^4$, —NHC(O)NHR$^4$, —NHNHC(O)R$^4$, —NHNHC(O)OR$^4$, —NHNHC(O)NHR$^4$, or —NH—N=C(R$^6$)R$^7$;
R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^6$ is —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkenyl), -phenylene-(CH$_2$)$_n$COOH, or -phenylene-(CH$_2$)$_n$COO—(C$_1$-C$_{10}$ alkyl);
R$^7$ is —H, —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkenyl) or —(CH$_2$)$_n$—(C$_8$-C$_{12}$ bicyclic cycloalkyl); and each n is independently an integer ranging from 1 to 5;
3) formula (Ic):

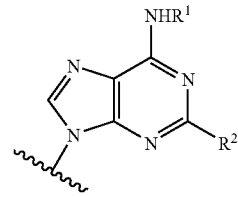

(Ic)

wherein
A is —CH$_2$NHR$^5$;
B and C are —OH;
D is

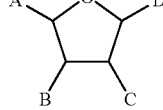

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$ —(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;
R$^2$ is —NHR$^4$, —OR$^4$, —SR$^4$, —NHC(O)R$^4$, —NHC(O)OR$^4$, —NHC(O)NHR$^4$, —NHNHC(O)R$^4$, —NHNHC(O)NHR$^4$, or —NHNHC(O)OR$^4$;
R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$ —(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^5$ is —C(O)O(C$_1$-C$_{10}$ alkyl), —C(O)NH(C$_1$-C$_{10}$ alkyl), —C(O)N(C$_1$-C$_{10}$ alkyl)$_2$, —C(O)NH-aryl, —CH(NH$_2$)NH$_2$ or —CH(NH$_2$)NH(C$_1$-C$_{10}$ alkyl); and each n is independently an integer ranging from 1 to 5;
4) formula (Id):

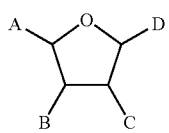

(Id)

wherein
A is —R³;
B and C are —OH;
D is

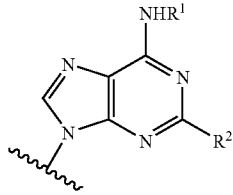

A and B are trans with respect to each other;
B and C are cis with respect to each other;
C and D are cis or trans with respect to each other;
R¹ is —$C_1$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
R² is —H, -halo, —CN, —NHR⁴, —OR⁴, —SR⁴, —NHC(O)R⁴, —NHC(O)OR⁴, —NHC(O)NHR⁴, —NHNHC(O)R⁴, —NHNHC(O)NHR⁴, —NHNHC(O)OR⁴ or —NH—N=C(R⁶)R⁷;
R³ is —$CH_2$ONO or —$CH_2$O$SO_3$H;
R⁴ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;
R⁶ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), —$(CH_2)_n$-(8- to 12-membered bicyclic heterocycle), -phenylene-$(CH_2)_n$COOH, or -phenylene-$(CH_2)_n$COO—($C_1$-$C_{10}$ alkyl);
R⁷ is —H, —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), or —$(CH_2)_n$-(8- to 12-membered bicyclic heterocycle); and
each n is independently an integer ranging from 1 to 5;
5) formula (Ie):

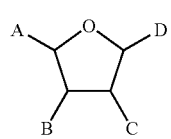

(Ie)

wherein
A is —$CH_2$R³;
B and C are —OH;
D is

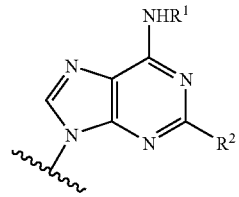

A and B are trans with respect to each other;
B and C are cis with respect to each other;
C and D are cis or trans with respect to each other;
R¹ is -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
R² is -halo, —CN, —NHC(O)R⁴, —NHR⁴, —OR⁴, —SR⁴, —NHC(O)OR⁴, —NHC(O)NHR⁴, —NHNHC(O)R⁴, —NHNHC(O)OR⁴, —NHNHC(O)NHR⁴, or —NH—N=C(R⁶)R⁷;
R³ is —O$SO_2$NH($C_1$-$C_{10}$ alkyl), —O$SO_2$N($C_1$-$C_{10}$ alkyl)₂, or —O$SO_2$NH-aryl;
R⁴ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;
R⁶ is —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$-(3- to 7-membered monocyclic heterocycle), —$(CH_2)_n$-(8- to 12-membered bicyclic heterocycle), -phenylene-$(CH_2)_n$COOH, or -phenylene-$(CH_2)_n$COO—($C_1$-$C_{10}$ alkyl);
R₇ is —H, —$C_1$-$C_{10}$ alkyl, -aryl, —$(CH_2)_n$-aryl, —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$-(3- to 7-membered monocyclic heterocycle), or —$(CH_2)_n$-(8- to 12-membered bicyclic heterocycle); and
each n is independently an integer ranging from 1 to 5;
6) formula (If):

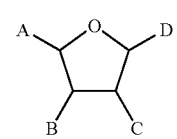

(If)

wherein
A is —CH$_2$ONO$_2$;
B and C are —OH;
D is

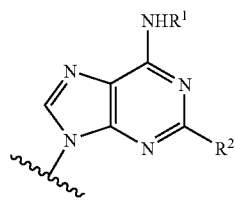

A and B are trans with respect to each other;
B and C are cis with respect to each other;
C and D are cis or trans with respect to each other;
R$^1$ is —C$_3$-C$_8$ monocyclic cycloalkyl; and
R$^2$ is —H or -halo;
7) formula (Ig):

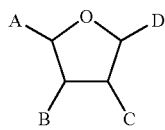

(Ig)

wherein
A is —CH$_2$ONO$_2$;
B and C are —OH;
D is

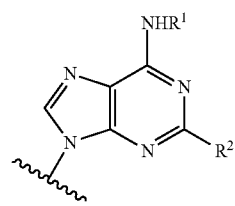

A and B are trans with respect to each other;
B and C are cis with respect to each other;
C and D are cis or trans with respect to each other; and
R$^1$ is -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl, —(CH$_2$)$_n$—(C$_3$-C$_8$ monocyclic cycloalkyl), —(CH$_2$)$_n$(C$_3$-C$_8$ monocyclic cycloalkenyl), —(CH$_2$)$_n$—(C$_8$-C$_{12}$ bicyclic cycloalkyl),
R$^2$ is —H or -halo;
or pharmaceutically acceptable salt thereof in an amount effective to reduce the animal's rate of metabolism, such that said animal's rate of metabolism or rate of oxygen consumption is reduced.

4. A method for treating tachycardia, the method comprising administering to an animal in need thereof an effective amount of a compound of formula (If):

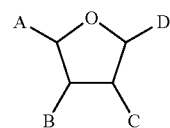

(If)

wherein
A is —CH$_2$ONO$_2$;
B and C are —OH;
D is

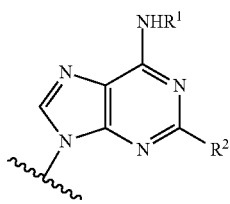

A and B are trans with respect to each other;
B and C are cis with respect to each other;
C and D are cis or trans with respect to each other;
R$^1$ is —C$_3$-C$_8$ monocyclic cycloalkyl; and
R$^2$ is —H or -halo;
or a pharmaceutically acceptable salt thereof, such that said tachycardia is treated.

5. The method of claim 4, wherein said tachycardia is atrial fibrillation or a supraventricular tachycardia.

6. The method of claim 5, wherein the treating includes lowering the animal's ventricular rate to a rate of from about 60 beats per minute to about 100 beats per minute.

7. The method of claim 5, wherein the treating includes lowering the animal's ventricular rate to a rate of not less than about 40 beats per minute.

8. The method of claim 5, wherein the compound has the formula:

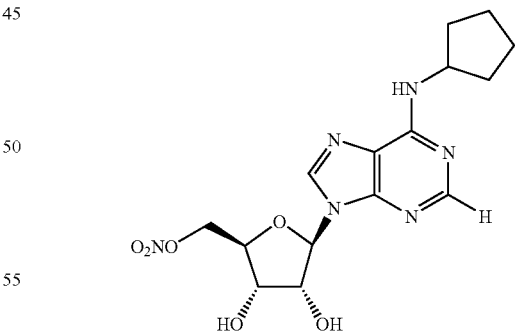

or a pharmaceutically acceptable salt thereof.

9. The method of claim 8, wherein the tachycardia is atrial fibrillation or a supraventricular tachycardia.

10. The method of claim 8, wherein the treating includes lowering the animal's ventricular rate to a rate of from about 60 beats per minute to about 100 beats per minute.

11. The method of claim 8, wherein the treating includes lowering the animal's ventricular rate to a rate of not less than about 40 beats per minute.

12. A method for converting a cardiac arrhythmia to a normal sinus rhythm, the method comprising administering to an animal in need thereof an effective amount of a compound of formula (If):

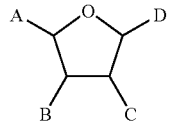
(If)

wherein

A is —CH$_2$ONO$_2$;

B and C are —OH;

D is

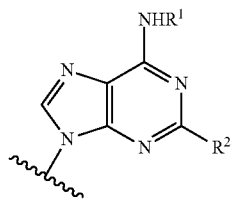

A and B are trans with respect to each other;

B and C are cis with respect to each other;

C and D are cis or trans with respect to each other;

R$^1$ is —C$_3$-C$_8$ monocyclic cycloalkyl; and

R$^2$ is —H or -halo;

or a pharmaceutically acceptable salt thereof, such that said cardiac arrhythmia is converted to a normal sinus rhythm.

13. The method of claim 12, wherein said compound has the formula:

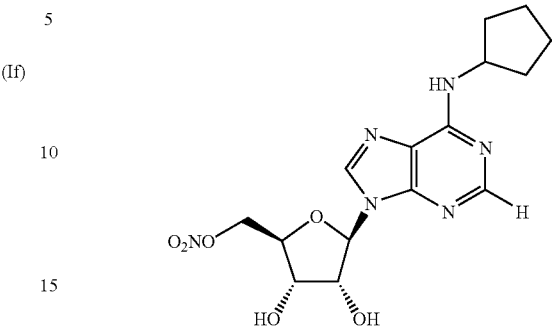

or a pharmaceutically acceptable salt thereof.

14. The method of claim 1, wherein said cardiovascular disease is atherosclerosis, congestive heart failure, circulatory shock, cardiomyopathy, cardiac transplant, cardioplegia, or a cardiac arrhythmia.

15. The method of claim 1, wherein said ischemic condition is stable angina, unstable angina, myocardial ischemia, hepatic ischemia, mesenteric artery ischemia, intestinal ischemia, myocardial infarction, critical limb ischemia, chronic critical limb ischemia, erebral ischemia, acute cardiac ischemia, or an ischemic disease of the central nervous system.

16. The method of claim 1, wherein said reperfusion injury is a intestinal reperfusion injury, myocardial reperfusion injury; or reperfusion injury resulting from cardiopulmonary bypass surgery, thoracoabrominal aneurysm repair surgery, carotid endaretectomy surgery, or hemorrhagic shock.

17. The method of claim 1, wherein said diabetes is Type I diabetes, Type II diabetes, gestational diabetes, insulinopathy, diabetes due to pancreatic disease, diabetes associated with another endocrine disease, Type A insulin resistance syndrome, Type B insulin resistance syndrome, lipatrophic diabetes, or diabetes induced by β-cell toxins.

18. The method of claim 1, wherein said wasting disease is chronic wasting disease, cancer wasting syndrome, or AIDS wasting syndrome.

\* \* \* \* \*